(12) United States Patent
Caldwell et al.

(10) Patent No.: US 11,738,010 B2
(45) Date of Patent: *Aug. 29, 2023

(54) OXAZOLIDINONES AS TARO INHIBITORS

(71) Applicant: MERCK SHARP & DOHME CORP., Rahway, NJ (US)

(72) Inventors: John P. Caldwell, Ringwood, NJ (US); Reynalda De Jesus, East Brunswick, NJ (US); Fa-Xiang Ding, Staten Island, NY (US); Charles J. Gill, Beachwood, NJ (US); Ginny Dai Ho, Murray Hill, NJ (US); Sookhee N. Ha, Warren, NJ (US); Sandra J. Koseoglu, Fanwood, NJ (US); Marc A. Labroli, West Point, PA (US); Sang Ho Lee, Berkeley Heights, NJ (US); Christina Madsen-Duggan, Scotch Plains, NJ (US); Mihir Mandal, Westfield, NJ (US); Terry Roemer, Cranford, NJ (US); Jing Su, Scotch Plains, NJ (US); Christopher Michael Tan, Scotch Plains, NJ (US); Zheng Tan, Westfield, NJ (US); Haifeng Tang, Metuchen, NJ (US); Hao Wang, Scotch Plains, NJ (US); Christine Yang, New Brunswick, NJ (US); Shu-Wei Yang, Edison, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/385,258

(22) Filed: Jul. 26, 2021

(65) Prior Publication Data
US 2021/0346364 A1 Nov. 11, 2021

Related U.S. Application Data

(63) Continuation of application No. 16/061,519, filed as application No. PCT/US2016/066284 on Dec. 13, 2016, now Pat. No. 11,141,410.
(Continued)

(51) Int. Cl.
*A61K 31/4439* (2006.01)
*A61P 31/04* (2006.01)
(Continued)

(52) U.S. Cl.
CPC ........ *A61K 31/4439* (2013.01); *A61K 31/407* (2013.01); *A61K 31/421* (2013.01); *A61K 31/422* (2013.01); *A61K 31/427* (2013.01); *A61K 31/431* (2013.01); *A61K 31/438* (2013.01); *A61K 31/4375* (2013.01); *A61K 31/4709* (2013.01); *A61K 31/5377* (2013.01); *A61K 31/5383* (2013.01); *A61P 31/04* (2018.01); *C07D 263/26* (2013.01); *C07D 413/04* (2013.01); *C07D 413/06* (2013.01); *C07D 413/12* (2013.01);
(Continued)

(58) Field of Classification Search
CPC .. A61K 31/407; A61K 31/421; A61K 31/422; A61K 31/427; A61K 31/431; A61K 31/4375; A61K 31/438; A61K 31/4439; A61K 31/4709; A61K 31/5377; A61K 31/5383; A61P 25/06; A61P 31/04; C07D 213/06; C07D 213/12; C07D 213/14; C07D 263/26; C07D 413/04; C07D 413/06; C07D 413/12; C07D 413/14; C07D 417/12; C07D 471/04; C07D 491/048; C07D 495/04; C07D 498/04; C07D 513/04
See application file for complete search history.

(56) References Cited

U.S. PATENT DOCUMENTS 3,754,000 A 8/1973 Fauran et al.
4,186,129 A 1/1980 Huth et al.
(Continued)

FOREIGN PATENT DOCUMENTS

EP 1277743 A1 1/2003
EP 1435353 A1 7/2004
(Continued)

OTHER PUBLICATIONS

International Search Report and Written Opinion for PCT/US2016/066284 dated Jun. 22, 2017.
(Continued)

*Primary Examiner* — Umamaheswari Ramachandran
(74) *Attorney, Agent, or Firm* — Meagher Emanuel Laks Goldberg & Liao, LLP

(57) ABSTRACT

Novel compounds of the structural formula I, and the pharmaceutically acceptable salts thereof, are inhibitors of TarO and may be useful in the prevention, treatment and suppression of diseases mediated by TarO, such as bacterial infections, including gram negative bacterial infections and gram positive bacterial infections such as MRSA and MRSE, alone or in combination with a β-lactam antibiotic.

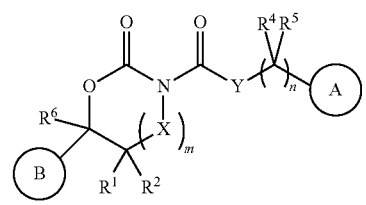

14 Claims, No Drawings

Related U.S. Application Data

(60) Provisional application No. 62/268,141, filed on Dec. 16, 2015.

(51) Int. Cl.

| | |
|---|---|
| *A61K 31/407* | (2006.01) |
| *A61K 31/421* | (2006.01) |
| *A61K 31/422* | (2006.01) |
| *A61K 31/427* | (2006.01) |
| *A61K 31/431* | (2006.01) |
| *A61K 31/4375* | (2006.01) |
| *A61K 31/438* | (2006.01) |
| *A61K 31/4709* | (2006.01) |
| *A61K 31/5377* | (2006.01) |
| *A61K 31/5383* | (2006.01) |
| *C07D 263/26* | (2006.01) |
| *C07D 413/04* | (2006.01) |
| *C07D 413/06* | (2006.01) |
| *C07D 413/12* | (2006.01) |
| *C07D 413/14* | (2006.01) |
| *C07D 417/12* | (2006.01) |
| *C07D 471/04* | (2006.01) |
| *C07D 491/048* | (2006.01) |
| *C07D 495/04* | (2006.01) |
| *C07D 498/04* | (2006.01) |

(52) U.S. Cl.
CPC ......... *C07D 413/14* (2013.01); *C07D 417/12* (2013.01); *C07D 471/04* (2013.01); *C07D 491/048* (2013.01); *C07D 495/04* (2013.01); *C07D 498/04* (2013.01)

(56) References Cited

U.S. PATENT DOCUMENTS

| | | | |
|---|---|---|---|
| 6,025,376 | A | 2/2000 | Laurent et al. |
| 2003/0199479 | A1 | 10/2003 | Takagi et al. |
| 2004/0214232 | A1 | 10/2004 | Burke et al. |

FOREIGN PATENT DOCUMENTS

| | | |
|---|---|---|
| JP | S6058968 A | 4/1985 |
| WO | 2009/151561 A2 | 12/2009 |
| WO | 2013148269 A1 | 10/2013 |

OTHER PUBLICATIONS

Lee et al. "TarO-specific inhibitors of wall teichoic acid biosynthesis restore beta-lactam efficacy 1-2, 19-21 against methicillin-resistant staphylococci" Science translational medicine. Mar. 9, 2016 (Mar. 9, 2016), vol. 8, p. 1-14.
Cohen, "Epidemiology of Drug Resistance: Implications for a Post-Antimicrobial Era", Science, vol. 257, p. 1051-1055, Aug. 21, 1992.
Neu, "The Crisis in Antibiotic Resistance", Science, vol. 257, pp. 1064-1073, Aug. 21, 1992.
Beck, W.D., et al., "Additional DNA in Methicillin-Resistant *Staphylococcus aureus* and Molecular Cloning of mec-Specific DNA", J. Bacteriol., vol. 165, No. 2, pp. 373-378 (1986).
Hartman, B.J., and Tomasz, "Low-Affinity Penicillin-Binding Protein Associated with 3-Lactam Resistance in *Staphylococcus aureus*" J. Bacteriol., vol. 158, No. 2, pp. 513-516 (1984).
Weidenmaier, C. and Peschel, A., "Teichoic acids and related cell-wall glycopolymers in Gram-positive physiology and host interactions", Nature, vol. 6, pp. 278-287, Apr. 2008.
Foster, Timothy J. "Immune Evasion by Staphylococci", Nature Review Microbiology, vol. 3, pp. 948-958, Dec. 2005.
Campbell, J. et al., "Synthetic Lethal Compound Combinations Reveal a Fundamental Connection between Wall Teichoic Acid and Peptidoglycan Biosyntheses in *Staphylococcus aureus*", ACS Chemical Biology, vol. 6, No. 1, pp. 106-116, 2011.
Sewell, E. W.C., and Brown, E.D., "Taking aim at wall teichoic acid synthesis: new biology and new leads for antibiotics", J. Antibiotics (2014) 67, 43-51.
Pasquina, Lincoln W.; et al., "Teichoic acid biosynthesis as an antibiotic target", Current Opinion in Microbiology (2013), 16, 531-537.
Farha, et al., "Inhibition of WTA Synthesis Blocks the Cooperative Action of PBPs and Sensitizes MRSA to β-Lactams", ACS Chemical Biology (2013), 8, 226-233.
Suzuki et al., "In Vitro Antimicrobial Activity of Wall Teichoic Acid Biosynthesis Inhibitors against *Staphylococcus aureus* Isolates", Antimicrobial Agents and Chemotherapy, vol. 55, No. 2, pp. 767-774, Feb. 2011.
Swoboda, Jonathan G.; et al., "Wall Teichoic Acid Function, Biosynthesis, and Inhibition", ChemBioChem, vol. 11, No. 1, pp. 35-45, Jan. 4, 2010.
Farha et al., "Designing analogs of ticlopidine, a wall teichoic acid inhibitor, to avoid formation of its oxidative metabolites", Bioorganic & Medicinal Chemistry Letters, vol. 24, No. 3, pp. 905-910; 2014.
Wang et al., "Discovery of Wall Teichoic Acid Inhibitors as Potential Anti-MRSA β- Lactam Combination Agents", Chemistry & Biology (Oxford, United Kingdom) vol. 20(2), pp. 272-284; Feb. 21, 2013.
Lee, K. et al., "Development of improved inhibitors of wall teichoic acid biosynthesis with potent activity against *Staphylococcus aureus*", Bioorganic & Medicinal Chemistry Letters, vol. 20(5), pp. 1767-1770; (2010).
Payne et al., "Comparative Activities of Clavulanic Acid, Sulbactam, and Tazobactam against Clinically Important β-Lactamases", Antimicrobial Agents and Chemotherapy, vol. 38, No. 4, pp. 767-772, Apr. 1994.
Hanaki et al., "TOC-39, a Novel Parenteral Broad-Spectrum Cephalosporin with Excellent Activity against Methicillin-Resistant *Staphylococcus aureus*", Antimicrobial Agents and Chemotherapy, vol. 39, No. 5, pp. 1120-1126, May 1995.
Extended European search report issued in corresponding EP 16876469.4 dated Apr. 12, 2019.
Hoover et al. "Towards the development of oxadiazinanones as chiral auxiliaries: synthesis and application of N'3-haloacetyloxadiazinanones". Tetrahedron Asymmetry. vol. 17. No. 12. Jul. 31, 2006 (Jul. 31, 2006), pp. 1831-1841. XP024961992.
Casper D. M. et al.: "Toward the Development of a Structurally Novel Class of Chiral Auxiliaries: Diastereoselective Aldol Reactions of a (1R.2S)-Ephedrine-Based 3, 4, 5, 6-Tetrahydro-2H-1,3,4-oxadiazin-2-one", Organic Letters. vol. 4, No. 21, Sep. 17, 2002 (Sep. 17, 2002), pp. 3739-3742, XP002790111.
Casper D. M. et al.: "Conformational Studies of N3-Substituted [1,3,4]-0xadiazinan-2-ones", Journal of Organic Chemistry, vol. 67, Nov. 19, 2002 (Nov. 19, 2002), pp. 8871-8876, XP002790112.
Lee W. et al.: "A light-inactivated antibiotic", Journal of Medicinal Chemistry, vol. 43, Dec. 16, 1999 (Dec. 16, 1999), pp. 128-132, XP002790113.
Blass B E et al: "A facile KF/A1 "20" 3 mediated method for the synthesis of substituted oxazolidinones", Tetrahedron Letters, vol. 40, No. 36, Sep. 3, 1999 (Sep. 3, 1999), pp. 6545-6547, XP004173955.
Pirkle W H et al: "Improved Chiral Derivatizing Agents for the Chromatographic Resolution of Racemic Primary Amines", Journal of Organic Chemistry, vol. 48, No. 15, Jan. 1, 1983 (Jan. 1, 1983), pp. 2520-2527, XP002022795.
Hein J. E. et al.: "Stereoselective conjugate radical additions: Application of a fluorous oxazolidinone chiral auxiliary for efficient tin removal", Organic Letters, vol. 7, No. 13, May 25, 2005 (May 25, 2005), pp. 2755-2758, XP002790114.
Lee K et al: "Development of improved inhibitors of wall teichoic acid biosynthesis with potent activity against *Staphylococcus aureus*", Bioorganic & Medicinal Chemistry Letters, vol. 20, No. 5, Mar. 1, 2010 (Mar. 1, 2010), pp. 1767-1770, XP026911352.
Examination Report for corresponding European Application No. 16876469.4, dated Mar. 18, 2021.
Sandberg et al., :Antimicrobial Agents and Chemotherapy, 2010, p. 2391-2400, 2010.

OXAZOLIDINONES AS TARO INHIBITORS

BACKGROUND OF THE INVENTION

Bacterial antibiotic resistance has become one of the most serious threats to modern health care. Cohen, *Science* 1992, 257: 1051-1055 discloses that infections caused by resistant bacteria frequently result in longer hospital stays, higher mortality and increased cost of treatment. Neu, *Science* 1992, 257: 1064-1073 discloses that the need for new antibiotics will continue to escalate because bacteria have a remarkable ability to develop resistance to new agents rendering them quickly ineffective. There have been various efforts to elucidate the mechanisms responsible for bacterial resistance, Coulton et al., *Progress in Medicinal Chemistry* 1994, 31: 297-349 teaches that the widespread use of penicillins and cephalosporins has resulted in the emergence of β-lactamases, a family of bacterial enzymes that catalyze the hydrolysis of the β-lactam ring common to numerous presently used antibiotics. More recently, Dudley, *Pharmacotherapy* 1995, 15: 9S-14S has disclosed that resistance mediated by β-lactamases is a critical aspect at the core of the development of bacterial antibiotic resistance.

Methicillin-resistant *Staphylococcus aureus* (MRSA) and *Staphylococcus epidermidis* (MRSE) have dramatically erroded the efficacy of β-lactam antibiotics. MRSA is emerging as a major cause of bloodstream infections in healthy individuals. In the 2013 Center for Disease Control and Prevention (CDC) Threat Level Report MRSA was designated as the second leading cause of mortality by drug-resistant bacterial pathogen in the US.

The most common mechanism of bacterial resistance to β-lactams involves inactivation by β-lactamases, and a successful strategy to overcome inactivation by combining a β-lactam and a β-lacatmase inhibitor has been used clinically for Gram negative infections (Walsh, C. T. (2003) Antibiotics: Actions, Origins, Resistance, ASM Press, Washington, D.C.). However, Gram positive MRSA strains develop resistance through a different mechanism: the acquisition of a β-lactam resistant peptidoglycan transpeptidase (TP) PBP2A (Beck, W. D., et al., J. Bacteriol. 165, 373-378 (1986); Hartman, B. J., and Tomasz, A. J. Bacteriol. 158, 513-516 (1984)).

The cell wall is the target of many widely used antibiotics, including β-lactams and glycopeptides. Wall teichoic acid (WTA) is an anionic glycophosphate polymer found as a major and integral component of most Gram-positive cell walls (Weidenmaier, C. and Peschel, A., Nature, April 2008, Vol. 6, 278-287; Swoboda, J. G. et al, ACS Chem. Biol. 4, 875-83 (2009); Lee, S. H. et al. Chemistry & Biology 18, 1379-89 (2011)). Although non-essential for *S. aureus* and *B. subtilis* at least under laboratory conditions, WTA has been shown to play a critical role in enabling Gram positive bacteria to adhere to an infected host cells (Weidenmaier, C. and Peschel, A., Nature, April 2008, Vol. 6, 278-287); In addition, WTA plays key roles in cell growth, division, peptidoglycan synthesis and β-lactam resistance in methicillin resistant *Staphylococcus aureus* (MRSA) (Sewell, E. W. C., and Brown, E.d., J. Antibiotics (2014) 67, 43-51; Pasquina, L. W., et al., Current Opinion in Microbiology 2013, 16: 531-537).

*S. aureus* has been known to evade host innate and adaptive immune defense system even though antibodies generated against *S. aureus* antigens are present in humans (Foster, Timothy J. Nature Review Microbiology 2005, 3, 948-958). Recently, WTA, as part of the *S. aureus* cell wall, was implicated in preventing epitope recognition and osponization by antibodies in the host (Spiegel, David A. et al. ACS Chemical Biology, Oct. 26, 2015 Just Accepted Manuscript). Therefore, WTA inhibitors can potentially sensitize pathogens to clearance by the host adaptive immune system. This approach can also be potentially useful for patients who have been previously administered *S. aureus* vaccine for the prevention of MRSA infections.

A recent study has shown that blocking the expression of wall teichoic acids (WTA) by inhibiting TarO, the first enzyme in the wall techoic acid biosyntheis in *S. aureus*, sensitizes methicillin-resistant *S. aureus* (MRSA) strains to β-lactams, even though β-lactam resistant transpeptidase is expressed (Campbell, J. Et al., ACS Chemical Biology, Vol. 6, No. 1, pp. 106-116, 2011). The study further showed that WTA expression is required for methicillin resistance to MRSA, and that preventing WTA biosynthesis by blocking TarO sensitizes MRSA strains to β-lactams due to the combined inactivation of the native penicillin binding proteins (PBP) and TarO. Further, the study showed that treatment of a TarO mutant of MW2, a MRSA strain exhibiting moderate reistance to β-lactams, showed an 8-fold increase in sensitivity to β-lactam antibiotics, including methicillin, imipenem, ceftazidime and cephradine, relative to the parent strain.

Finally, it has been suggested that Ticlopidine, an antiplatelet drug, may show low level activity against TarO and is only synergistic with the β-lactam antibiotic, cefuroxime, and restores the efficacy of cefuroxime in a community acquired MRSA strain USA300 (Sewell, E. W. C., and Brown, E. D., J. Antibiotics (2014) 67, 43-51). Based on these findings, the combination of a TarO inhibitor with a β-lactam antibiotic may be useful for treating MRSA infections, particularly in β-lactam resistant MRSA and MRSE strains.

Due to the decrease in efficacy of β-lactam antibiotics, such as dicloxacillin, cefuroxime and cefepime in treating dangerous bacterial pathogens, there is a need for the development of antibiotic combination agents to preserve the efficacy of β-lactams. The compounds of the present invention are novel TarO inhibitors which may be effective, alone or in combination with a β-lactam antibiotic, in preventing and treating bacterial infections. The compounds of the present invention, alone or in combination with a β-lactam antibiotic, may also be effective in enhancing bacterial clearance by the immune system.

Wall teichoic acids and their relevance to antibiotic resistance are disclosed in: Sewell, Edward W. C., and Brown, E. D., Journal of Antibiotics (2014), 67(1), 43-51; Pasquina, Lincoln W.; et al., Current Opinion in Microbiology (2013), 16(5), 531-537; Brown, E. D., et al., ACS Chemical Biology (2013), 8(1), 226-233; Gilmore, M. S., et al., Antimicrobial Agents and Chemotherapy (2011), 55(2), 767-774; and Swoboda, Jonathan G.; et al., ChemBioChem (2010), 11(1), 35-45.

WTA inhibitors are disclosed in Brown, E. D. et al., Bioorganic & Medicinal Chemistry Letters (2014), 24(3), 905-910; Liang, Lianzhu; et al., Chemistry & Biology (Oxford, United Kingdom) (2013), 20(2), 272-284; Walker, S. et al., Bioorganic & Medicinal Chemistry Letters (2010), 20(5), 1767-1770; and WO2013148269.

SUMMARY OF THE INVENTION

The present invention relates to novel compounds of structural formula I:

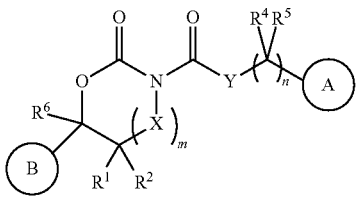

and pharmaceutically acceptable salts thereof. The compounds of structural formula I, and embodiments thereof, are inhibitors of TarO and may be useful in the prevention, treatment, and suppression of diseases, disorders and conditions mediated by inhibition of TarO, such as bacterial infections. The compounds of the present invention, and pharmaceutically acceptable salts thereof, are also useful in combination with β-lactam antibiotics, such as imipenem and dicloxacillin, for the treatment of bacterial infections, particularly antibiotic resistant bacterial infections such as methicillin-resistant *Staphylococcus aureus* (MRSA) infections.

The present invention also relates to pharmaceutical compositions comprising the compounds of the present invention, or pharmaceutically acceptable salts thereof, and a pharmaceutically acceptable carrier. The present invention also relates to methods for the treatment, control or prevention of disorders, diseases, and conditions that may be responsive to inhibition of TarO in a subject in need thereof by administering the compounds of the present invention, or pharmaceutically acceptable salts thereof, and pharmaceutical compositions of the present invention. The present invention also relates to the use of compounds of the present invention, or pharmaceutically acceptable salts thereof, for manufacture of a medicament useful in treating diseases, disorders and conditions that may be responsive to the inhibition of TarO. The present invention is also concerned with treatment of these diseases, disorders and conditions by administering the compounds of the present invention, or pharmaceutically acceptable salts thereof, in combination with a therapeutically effective amount of another agent that may be useful to treat the disease, disorder and condition. The invention is further concerned with processes for preparing the compounds of the present invention, or pharmaceutically acceptable salts thereof.

DETAILED DESCRIPTION OF THE INVENTION

The present invention is concerned with novel compounds of structural Formula I:

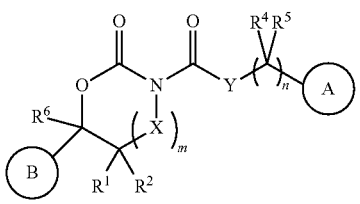

or a pharmaceutically acceptable salt thereof; wherein

A is selected from the group consisting of:
(1) aryl,
(2) heteroaryl,
(3) —O-aryl, and
(4) —O-heteroaryl,
wherein aryl and heteroaryl are unsubstituted or substituted with 1-5 substituents selected from $R^a$;
B is selected from the group consisting of:
(1) aryl, and
(2) heteroaryl,
wherein aryl and heteroaryl are unsubstituted or substituted with 1-4 substituents selected from $R^b$;
X is selected from the group consisting of:
(1) $NR^7$,
(2) —$CR^8R^9$, and
(3) —O—;
Y is selected from the group consisting of:
(1) $NR^3$,
(2) —$CR^{10}R^{11}$, and
(3) —$C(R^{12})$=$C(R^{13})$—;
$R^1$ is selected from the group consisting of:
(1) hydrogen,
(2) halogen,
(3) —$C_{1-6}$alkyl, and
(4) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;
$R^2$ is selected from the group consisting of:
(1) hydrogen,
(2) halogen,
(3) —$C_{1-6}$alkyl, and
(4) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl, or $R^1$ and $R^2$ together with the carbon atom they are attached to form a $C_{3-6}$cycloalkyl ring, wherein the cycloalkyl ring is unsubstituted or substituted with 1-2 substituents selected from: halogen, —$C_{1-6}$alkyl, and —$OC_{1-6}$alkyl;
$R^3$ is selected from the group consisting of:
(1) hydrogen,
(2) OH, and
(3) —$C_{1-6}$alkyl,
wherein alkyl is unsubstituted or substituted with one to five substituents selected from —$C_{1-6}$alkyl;
each $R^4$ is independently selected from the group consisting of:
(1) hydrogen,
(2) halogen,
(3) —$C_{1-6}$alkyl, and
(4) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;
each $R^5$ is independently selected from the group consisting of:
(1) hydrogen,
(2) halogen,
(3) —$C_{1-6}$alkyl, and
(4) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;

$R^6$ is selected from the group consisting of:
(1) hydrogen,
(2) halogen,
(3) —$C_{1-6}$alkyl,
(4) —$C_{2-6}$alkenyl, and
(5) —$(CH_2)_p$—OH,
wherein $CH_2$, alkyl and alkenyl are unsubstituted or substituted with 1-2 substituents selected from: halogen, —$C_{1-6}$alkyl, and —$OC_{1-6}$alkyl;
$R^7$ is selected from the group consisting of:
(1) hydrogen,
(2) halogen,
(3) —$C_{1-6}$alkyl,
(4) —$C_{2-6}$alkenyl, and
(5) —$(CH_2)_p$—OH,
wherein $CH_2$, alkyl and alkenyl are unsubstituted or substituted with 1-2 substituents selected from: halogen, —$C_{1-6}$alkyl, and —$OC_{1-6}$alkyl;
$R^8$ is selected from the group consisting of:
(1) hydrogen,
(2) halogen,
(3) —$C_{1-6}$alkyl, and
(4) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;
$R^9$ is selected from the group consisting of:
(1) hydrogen,
(2) halogen,
(3) —$C_{1-6}$alkyl, and
(4) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;
$R^{10}$ is selected from the group consisting of:
(1) hydrogen,
(2) halogen,
(3) —$C_{1-6}$alkyl, and
(4) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;
$R^{11}$ is selected from the group consisting of:
(1) hydrogen,
(2) halogen,
(3) —$C_{1-6}$alkyl, and
(4) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;
$R^{12}$ is selected from the group consisting of:
(1) hydrogen,
(2) halogen,
(3) —$C_{1-6}$alkyl, and
(4) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;
$R^{13}$ is selected from the group consisting of:
(1) hydrogen,
(2) halogen,
(3) —$C_{1-6}$alkyl, and
(4) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;

each $R^a$ is independently selected from the group consisting of:
(1) halogen,
(2) —$C_{1-6}$alkyl,
(3) —$OC_{1-6}$alkyl,
(4) —$OC_{2-6}$alkenyl,
(5) —OH,
(6) oxo,
(7) —CN,
(8) —$NO_2$,
(9) —$NR^cR^d$,
(10) —$CH_2NR^cR^d$,
(11) —$SO_2C_{1-6}$alkyl,
(12) —$C_{3-6}$cycloalkyl,
(13) —$C_{2-6}$cycloheteroalkyl,
(14) aryl, and
(15) heteroaryl,
wherein —$CH_2$, alkyl, alkenyl, cycloalkyl, cycloheteroalkyl, aryl and heteroaryl are unsubstituted or substituted with 1-4 substituents selected from: halogen, —$C_{1-6}$alkyl, —$OC_{1-6}$alkyl, and —$CO_2C_{1-6}$alkyl;
each $R^b$ is independently selected from the group consisting of:
(1) halogen,
(2) —$C_{1-6}$alkyl,
(3) —$C_{2-6}$alkenyl,
(4) —$OC_{1-6}$alkyl,
(5) —$OC_{2-6}$alkenyl,
(6) —OH,
(7) oxo,
(8) —CN,
(9) —$NO_2$,
(10) —$NR^cR^d$,
(11) —$SO_2C_{1-6}$alkyl,
(12) —$C_{3-6}$cycloalkyl,
(13) —$C_{2-6}$cycloheteroalkyl,
(14) aryl, and
(15) heteroaryl,
wherein alkyl, alkenyl, cycloalkyl, cycloheteroalkyl, aryl and heteroaryl are unsubstituted or substituted with 1-4 substituents selected from: halogen, —$C_{1-6}$alkyl, —$OC_{1-6}$alkyl, and —$CO_2C_{1-6}$alkyl;
each $R^c$ is independently selected from the group consisting of:
(1) hydrogen,
(2) $C_{1-6}$alkyl,
(3) $C_{2-6}$alkenyl,
(4) $C_{1-6}$alkyl-OH,
(5) $C_{3-6}$cycloalkyl,
(6) C(O)$C_{1-6}$alkyl, and
(7) $SO_2C_{1-6}$alkyl,
wherein alkyl, alkenyl and cycloalkyl are unsubstituted or substituted with one to three substituents selected from halogen, —$C_{1-6}$alkyl, —$OC_{1-6}$alkyl, and —$CO_2C_{1-6}$alkyl;
each $R^d$ is independently selected from the group consisting of:
(1) hydrogen,
(2) $C_{1-6}$alkyl,
(3) $C_{2-6}$alkenyl,
(4) $C_{1-6}$alkyl-OH,
(5) $C_{3-6}$cycloalkyl,
(6) C(O)$C_{1-6}$alkyl, and
(7) $SO_2C_{1-6}$alkyl,
wherein alkyl, alkenyl and cycloalkyl are unsubstituted or substituted with one to three substituents selected from halogen, —$C_{1-6}$alkyl, —$OC_{1-6}$alkyl, and —$CO_2C_{1-6}$alkyl, or $R^c$ and $R^d$ together with the nitrogen atom they are attached to form a $C_{4-8}$cycloheteroalkyl ring, wherein the $C_{4-8}$cycloheteroalkyl ring is unsubstituted or substituted with 1-4 substituents selected from halogen, oxo, —$C_{1-6}$alkyl, —$OC_{1-6}$alkyl, and —$CO_2C_{1-6}$alkyl;

m is 0 or 1;
n is 0, 1, 2 or 3; and
p is 0, 1, 2, 3, 4, 5 or 6.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, A is selected from the group consisting of: aryl, heteroaryl, —O-aryl, and —O-heteroaryl, wherein aryl and heteroaryl are unsubstituted or substituted with 1-5 substituents selected from $R^a$.

In another embodiment of the present invention, A is selected from the group consisting of: aryl, heteroaryl, and —O-aryl, wherein aryl and heteroaryl are unsubstituted or substituted with 1-5 substituents selected from $R^a$. In another embodiment of the present invention, A is selected from the group consisting of: phenyl, naphthalene, tetrahydronaphthalene, isoquinoline, pyrazolo[1,5-a]pyridine, naphthyridine, quinoxaline, dihydrobenzodioxin, indole, indazole, thieno[3,2-c]pyridine, furo[2,3-c]pyridine, thiazole, quinoline, pyridine, pyrazole, quinazoline, dihydroisoindole, dihydrocyclopentan[b]pyridine, imidazo[2,1-b][1,3]thiazole, dihydropyrido[3,2-b][1,4]oxazine, benzothiophene, —O-phenyl, —O-naphthalene, isoindoline-1-one, 2H-benzo[b][1,4]oxazin-3(4H)-one, and benzo[d]oxazol-2(3H)-one, wherein A is unsubstituted or substituted with 1-5 substituents selected from $R^a$.

In another embodiment of the present invention, A is selected from the group consisting of: phenyl, naphthalene, tetrahydronaphthalene, isoquinoline, pyrazolo[1,5-a]pyridine, naphthyridine, quinoxaline, dihydrobenzodioxin, indole, indazole, thieno[3,2-c]pyridine, furo[2,3-c]pyridine, thiazole, quinoline, pyridine, pyrazole, quinazoline, dihydroisoindole, dihydrocyclopentan[b]pyridine, imidazo[2,1-b][1,3]thiazole, dihydropyrido[3,2-b][1,4]oxazine, benzothiophene, —O-phenyl, and —O-naphthalene, wherein A is unsubstituted or substituted with 1-5 substituents selected from $R^a$.

In another embodiment of the present invention, A is selected from the group consisting of: aryl, and heteroaryl, wherein aryl and heteroaryl are unsubstituted or substituted with 1-5 substituents selected from $R^a$. In another embodiment of the present invention, A is selected from the group consisting of: phenyl, naphthalene, tetrahydronaphthalene, isoquinoline, pyrazolopyridine, naphthyridine, quinoxaline, dihydrobenzodioxin, indole, indazole, thieno[3,2-c]pyridine, furopyridine, thiazole, quinoline, pyridine, pyrazole, quinazoline, dihydroisoindole, dihydrocyclopentan[b]pyridine, imidazothiazole, dihydropyrido oxazine, and benzothiophene, wherein A is unsubstituted or substituted with 1-5 substituents selected from $R^a$. In another embodiment of the present invention, A is selected from the group consisting of: phenyl, naphthalene, tetrahydronaphthalene, isoquinoline, pyrazolo[1,5-a]pyridine, naphthyridine, quinoxaline, dihydrobenzodioxin, indole, indazole, thieno[3,2-c]pyridine, furo[2,3-c]pyridine, thiazole, quinoline, pyridine, pyrazole, quinazoline, dihydroisoindole, dihydrocyclopentan[b]pyridine, imidazo[2,1-b][1,3]thiazole, dihydropyrido[3,2-b][1,4]oxazine, and benzothiophene, wherein A is unsubstituted or substituted with 1-5 substituents selected from $R^a$. In another embodiment of the present invention, A is selected from the group consisting of: phenyl, naphthalene, isoquinoline, pyrazolo[1,5-a]pyridine, naphthyridine, quinazoline, and benzothiophene, wherein A is unsubstituted or substituted with 1-5 substituents selected from $R^a$.

In another embodiment of the present invention, A is selected from the group consisting of: phenyl, naphthalene, isoquinoline, pyrazolopyridine, naphthyridine, quinazoline, and benzothiophene, wherein A is unsubstituted or substituted with 1-5 substituents selected from $R^a$. In another embodiment of the present invention, A is selected from the group consisting of: phenyl, naphthalene, isoquinoline, pyrazolo[1,5-a]pyridine, 1,6-naphthyridine, quinazoline, and benzothiophene wherein A is unsubstituted or substituted with 1-5 substituents selected from $R^a$.

In another embodiment of the present invention, A is selected from the group consisting of: isoquinoline, and naphthyridine, wherein A is unsubstituted or substituted with 1-5 substituents selected from $R^a$. In another embodiment of the present invention, A is selected from the group consisting of: isoquinoline and 1,6-naphthyridine, wherein A is unsubstituted or substituted with 1-5 substituents selected from $R^a$.

In another embodiment of the present invention, A is aryl, wherein aryl is unsubstituted or substituted with 1-5 substituents selected from $R^a$. In another embodiment of the present invention, A is selected from the group consisting of: phenyl, naphthalene, and tetralin, wherein phenyl, naphthalene and tetralin are unsubstituted or substituted with 1-5 substituents selected from $R^a$. In another embodiment of the present invention, A is selected from the group consisting of: phenyl, and naphthalene, wherein phenyl and naphthalene are unsubstituted or substituted with 1-5 substituents selected from $R^a$. In another embodiment of the present invention, A is phenyl, wherein phenyl is unsubstituted or substituted with 1-5 substituents selected from $R^a$. In another embodiment of the present invention, A is naphthalene, wherein naphthalene is unsubstituted or substituted with 1-5 substituents selected from $R^a$. In another embodiment of the present invention, A is tetralin, wherein tetralin is unsubstituted or substituted with 1-5 substituents selected from $R^a$.

In another embodiment of the present invention, A is heteroaryl, wherein heteroaryl is unsubstituted or substituted with 1-5 substituents selected from $R^a$.

In another embodiment of the present invention, A is selected from the group consisting of: isoquinoline, pyrazolo[1,5-a]pyridine, 1,6-naphthyridine, quinoxaline, 2,3-dihydro-1,4-benzodioxine or benzodioxane, indole, thieno[3,2-c]pyridine, furo[2,3-c]pyridine, thiazole, quinoline, pyridine, pyrazole, quinazoline, 2,3-dihydroisoindole, 6,7-dihydro-5H-cyclopentan[b]pyridine, imidazo[2,1-b][1,3]thiazole, 2,3-dihydropyrido[3,2-b][1,4]oxazine, benzothiophene, isoindoline-1-one, 2H-benzo[b][1,4]oxazin-3(4H)-one, and benzo[d]oxazol-2(3H)-one, wherein A is unsubstituted or substituted with 1-5 substituents selected from $R^a$.

In another embodiment of the present invention, A is selected from the group consisting of: isoquinoline, pyrazolo[1,5-a]pyridine, 1,6-naphthyridine, quinoxaline, 2,3-dihydro-1,4-benzodioxine or benzodioxane, indole, thieno[3,2-c]pyridine, furo[2,3-c]pyridine, thiazole, quinoline, pyridine, pyrazole, quinazoline, 2,3-dihydroisoindole, 6,7-dihydro-5H-cyclopentan[b]pyridine, imidazo[2,1-b][1,3]thiazole, 2,3-dihydropyrido[3,2-b][1,4]oxazine, and benzothiophene, wherein A is unsubstituted or substituted with 1-5 substituents selected from $R^a$.

In another embodiment of the present invention, A is selected from the group consisting of: isoquinoline, pyrazolo[1,5-a]pyridine, 1,6-naphthyridine, quinazoline, and benzothiophene, wherein A is unsubstituted or substituted with 1-5 substituents selected from $R^a$. In another embodiment of the present invention, A is selected from the group consisting of: isoquinoline, and 1,6-naphthyridine, wherein A is unsubstituted or substituted with 1-5 substituents selected from $R^a$. In another embodiment of the present invention, A is isoquinoline, wherein A is unsubstituted or substituted with 1-5 substituents selected from $R^a$. In another embodiment of the present invention, A is pyrazolo[1,5-a]pyridine, wherein A is unsubstituted or substituted with 1-5 substituents selected from $R^a$. In another embodiment of the present invention, A is 1,6-naphthyridine, wherein A is unsubstituted or substituted with 1-5 substituents selected from $R^a$. In another embodiment of the present invention, A is quinazoline, wherein A is unsubstituted or substituted with 1-5 substituents selected from $R^a$. In another embodiment of the present invention, A is benzothiophene, wherein A is unsubstituted or substituted with 1-5 substituents selected from $R^a$.

In another embodiment of the present invention, B is selected from the group consisting of: aryl, and heteroaryl, wherein aryl and heteroaryl are unsubstituted or substituted with 1-4 substituents selected from $R^b$.

In another embodiment of the present invention, B is selected from the group consisting of: phenyl, pyridine, and pyrimidine, wherein phenyl, pyridine and pyrimidine are unsubstituted or substituted with 1-4 substituents selected from $R^b$.

In another embodiment of the present invention, B is selected from the group consisting of: phenyl, and pyridine, wherein phenyl and pyridine are unsubstituted or substituted with 1-4 substituents selected from $R^b$. In another embodiment of the present invention, B is phenyl, wherein phenyl is unsubstituted or substituted with 1-4 substituents selected from $R^b$. In another embodiment of the present invention, B is pyridine, wherein pyridine is unsubstituted or substituted with 1-4 substituents selected from $R^b$.

In another embodiment of the present invention, X is selected from the group consisting of: $NR^7$, $—CR^8R^9$, and —O—. In another embodiment of the present invention, X is selected from the group consisting of: $NR^7$, and $—CR^8R^9$. In another embodiment of the present invention, X is selected from the group consisting of: $NR^7$. In another embodiment of the present invention, X is selected from the group consisting of: $—CR^8R^9$.

In another embodiment of the present invention, Y is selected from the group consisting of: $NR^3$, $—CR^{10}R^{11}$, and $—C(R^{12})=C(R^{13})—$. In another embodiment of the present invention, Y is selected from the group consisting of: $NR^3$ and $—CR^{10}R^{11}$. In another embodiment of the present invention, Y is $NR^3$. In another embodiment of the present invention, Y is $—CR^{10}R^{11}$. In another embodiment of the present invention, Y is $—C(R^{12})=C(R^{13})—$.

In another embodiment of the present invention, $R^1$ is selected from the group consisting of: hydrogen, halogen, $—C_{1-6}$alkyl, and $—(CH_2)_p—OH$, wherein $CH_2$ and alkyl are unsubstituted or substituted with 1-2 substituents selected from: halogen, $—C_{1-6}$alkyl, and $—OC_{1-6}$alkyl.

In another embodiment of the present invention, $R^1$ is selected from the group consisting of: hydrogen, $—C_{1-6}$alkyl, and $—(CH_2)_p—OH$, wherein $CH_2$ and alkyl are unsubstituted or substituted with 1-2 substituents selected from: halogen, $—C_{1-6}$alkyl, and $—OC_{1-6}$alkyl. In another embodiment of the present invention, $R^1$ is selected from the group consisting of: hydrogen, $—C_{1-6}$alkyl, and $—(CH_2)_p—OH$. In another embodiment of the present invention, $R^1$ is selected from the group consisting of: hydrogen, $—CH_3$, $—CH_2CH_3$, $—CH_2OH$, and $—(CH_2)_2OH$, wherein $CH_2$ and alkyl are unsubstituted or substituted with 1-2 substituents selected from: halogen, $—C_{1-6}$alkyl, and $—OC_{1-6}$alkyl. In another embodiment of the present invention, $R^1$ is selected from the group consisting of: hydrogen, $—CH_3$, $—CH_2CH_3$, $—CH_2OH$, and $—(CH_2)_2OH$.

In another embodiment of the present invention, $R^1$ is selected from the group consisting of: hydrogen, and $—C_{1-6}$alkyl, wherein alkyl is unsubstituted or substituted with 1-2 substituents selected from: halogen, $—C_{1-6}$alkyl, and $—OC_{1-6}$alkyl.

In another embodiment of the present invention, $R^1$ is selected from the group consisting of: hydrogen, $—CH_3$, and $—CH_2CH_3$. In another embodiment of the present invention, $R^1$ is selected from the group consisting of: hydrogen, and $—CH_3$.

In another embodiment of the present invention, $R^2$ is selected from the group consisting of: hydrogen, halogen, $—C_{1-6}$alkyl, and $—(CH_2)_p—OH$, wherein $CH_2$ and alkyl are unsubstituted or substituted with 1-2 substituents selected from: halogen, $—C_{1-6}$alkyl, and $—OC_{1-6}$alkyl, or $R^1$ and $R^2$ together with the carbon atom they are attached to form a $C_{3-6}$cycloalkyl ring, wherein the cycloalkyl ring is unsubstituted or substituted with 1-2 substituents selected from: halogen, $—C_{1-6}$alkyl, and $—OC_{1-6}$alkyl.

In another embodiment of the present invention, $R^2$ is selected from the group consisting of: hydrogen, $—C_{1-6}$alkyl, and $—(CH_2)_p—OH$, wherein $CH_2$ and alkyl are unsubstituted or substituted with 1-2 substituents selected from: halogen, $—C_{1-6}$alkyl, and $—OC_{1-6}$alkyl, or $R^1$ and $R^2$ together with the carbon atom they are attached to form a $C_{3-6}$cycloalkyl ring, wherein the cycloalkyl ring is unsubstituted or substituted with 1-2 substituents selected from: halogen, $—C_{1-6}$alkyl, and $—OC_{1-6}$alkyl.

In another embodiment of the present invention, $R^2$ is selected from the group consisting of: hydrogen, $—C_{1-6}$alkyl, and $—(CH_2)_p—OH$, wherein $CH_2$ and alkyl are unsubstituted or substituted with 1-2 substituents selected from: halogen, $—C_{1-6}$alkyl, and $—OC_{1-6}$alkyl, or $R^1$ and $R^2$ together with the carbon atom they are attached to form a cyclopropyl ring, wherein the cyclopropyl ring is unsubstituted or substituted with 1-2 substituents selected from: halogen, $—C_{1-6}$alkyl, and $—OC_{1-6}$alkyl. In another embodiment of the present invention, $R^2$ is selected from the group consisting of: hydrogen, $—CH_3$, $—CH_2CH_3$, $—CH_2OH$, and $—(CH_2)_2OH$, or $R^1$ and $R^2$ together with the carbon atom they are attached to form a cyclopropyl ring, wherein the cyclopropyl ring is unsubstituted or substituted with 1-2 substituents selected from: halogen, $—C_{1-6}$alkyl, and $—OC_{1-6}$alkyl.

In another embodiment of the present invention, $R^2$ is selected from the group consisting of: hydrogen, $—C_{1-6}$alkyl, and $—(CH_2)_p—OH$, wherein $CH_2$ and alkyl are unsubstituted or substituted with 1-2 substituents selected from: halogen, $—C_{1-6}$alkyl, and $—OC_{1-6}$alkyl. In another embodiment of the present invention, $R^2$ is selected from the group consisting of: hydrogen, $—CH_3$, $—CH_2CH_3$, $—CH_2OH$, and $—(CH_2)_2OH$. In another embodiment of the present invention, $R^2$ is selected from the group consisting of: hydrogen, $—CH_3$, and $—CH_2OH$.

In another embodiment of the present invention, $R^1$ and $R^2$ are each independently selected from the group consisting of: hydrogen, $—C_{1-6}$alkyl, and $—(CH_2)_p—OH$, provided that one of $R^1$ and $R^2$ is selected from $—C_{1-6}$alkyl and $—(CH_2)_p—OH$. In another embodiment of the present invention, $R^1$ and $R^2$ are each independently selected from the group consisting of: hydrogen, $—CH_3$, $—CH_2CH_3$, —CH$_2$OH, and —(CH$_2$)$_2$OH, provided that one of R$^1$ and R$^2$ is selected from —CH$_3$, —CH$_2$CH$_3$, —CH$_2$OH, and —(CH$_2$)$_2$OH. In another embodiment of the present invention, R$^1$ and R$^2$ are each independently selected from the group consisting of: hydrogen, and —C$_{1-6}$alkyl, provided that one of R$^1$ and R$^2$ is selected from —C$_{1-6}$alkyl.

In another embodiment of the present invention, R$^1$ is hydrogen, and R$^2$ is —C$_{1-6}$alkyl. In another embodiment of the present invention, R$^1$ is hydrogen, and R$^2$ is —CH$_3$. In another embodiment of the present invention, R$^1$ is hydrogen and R$^2$ is hydrogen or —C$_{1-6}$alkyl. In another embodiment of the present invention, R$^1$ is hydrogen and R$^2$ is hydrogen or —CH$_3$.

In another embodiment of the present invention, R$^2$ is hydrogen, and R$^1$ is —C$_{1-6}$alkyl. In another embodiment of the present invention, R$^2$ is hydrogen, and R$^1$ is —CH$_3$. In another embodiment of the present invention, R$^2$ is hydrogen and R$^1$ is hydrogen or —C$_{1-6}$alkyl. In another embodiment of the present invention, R$^2$ is hydrogen and R$^1$ is hydrogen or —CH$_3$.

In another embodiment of the present invention, R$^3$ is selected from the group consisting of: hydrogen, OH, and —C$_{1-6}$alkyl, wherein alkyl is unsubstituted or substituted with one to five substituents selected from —C$_{1-6}$alkyl.

In another embodiment of the present invention, R$^3$ is selected from the group consisting of: hydrogen, and —C$_{1-6}$ alkyl, wherein alkyl is unsubstituted or substituted with one to five substituents selected from —C$_{1-6}$alkyl. In another embodiment of the present invention, R$^3$ is selected from the group consisting of: hydrogen, OH, and —C$_{1-6}$alkyl.

In another embodiment of the present invention, R$^3$ is selected from the group consisting of: hydrogen, and OH. In another embodiment of the present invention, R$^3$ is —C$_{1-6}$ alkyl. In another embodiment of the present invention, R$^3$ is OH. In another embodiment of the present invention, R$^3$ is hydrogen.

In another embodiment of the present invention, each R$^4$ is independently selected from the group consisting of: hydrogen, halogen, —C$_{1-6}$alkyl, and —(CH$_2$)$_p$—OH, wherein CH$_2$ and alkyl are unsubstituted or substituted with 1-2 substituents selected from: halogen, —C$_{1-6}$alkyl, and —OC$_{1-6}$alkyl. In another embodiment of the present invention, each R$^4$ is independently selected from the group consisting of: hydrogen, —C$_{1-6}$alkyl, and —(CH$_2$)$_p$—OH, wherein CH$_2$ and alkyl are unsubstituted or substituted with 1-2 substituents selected from: halogen, —C$_{1-6}$alkyl, and —OC$_{1-6}$alkyl. In another embodiment of the present invention, each R$^4$ is independently selected from the group consisting of: hydrogen, halogen, and —C$_{1-6}$alkyl, wherein alkyl are unsubstituted or substituted with 1-2 substituents selected from: halogen, —C$_{1-6}$alkyl, and —OC$_{1-6}$alkyl.

In another embodiment of the present invention, each R$^4$ is independently selected from the group consisting of: hydrogen, halogen, and —C$_{1-6}$alkyl. In another embodiment of the present invention, each R$^4$ is independently selected from the group consisting of: hydrogen, and —C$_{1-6}$alkyl. In another embodiment of the present invention, each R$^4$ is —C$_{1-6}$alkyl. In another embodiment of the present invention, each R$^4$ is hydrogen.

In another embodiment of the present invention, each R$^5$ is independently selected from the group consisting of: hydrogen, halogen, —C$_{1-6}$alkyl, and —(CH$_2$)$_p$—OH, wherein CH$_2$ and alkyl are unsubstituted or substituted with 1-2 substituents selected from: halogen, —C$_{1-6}$alkyl, and —OC$_{1-6}$alkyl. In another embodiment of the present invention, each R$^5$ is independently selected from the group consisting of: hydrogen, —C$_{1-6}$alkyl, and —(CH$_2$)$_p$—OH, wherein CH$_2$ and alkyl are unsubstituted or substituted with 1-2 substituents selected from: halogen, —C$_{1-6}$alkyl, and —OC$_{1-6}$alkyl.

In another embodiment of the present invention, each R$^5$ is independently selected from the group consisting of: hydrogen, halogen, and —C$_{1-6}$alkyl, wherein alkyl are unsubstituted or substituted with 1-2 substituents selected from: halogen, —C$_{1-6}$alkyl, and —OC$_{1-6}$alkyl.

In another embodiment of the present invention, each R$^5$ is independently selected from the group consisting of: hydrogen, halogen, and —C$_{1-6}$alkyl. In another embodiment of the present invention, each R$^5$ is independently selected from the group consisting of: hydrogen, and —C$_{1-6}$alkyl. In another embodiment of the present invention, each R$^5$ is —C$_{1-6}$alkyl. In another embodiment of the present invention, each R$^5$ is hydrogen.

In another embodiment, R$^6$ is selected from the group consisting of: hydrogen, halogen, —C$_{1-6}$alkyl, —C$_{2-6}$alkenyl, and —(CH$_2$)$_p$—OH, wherein CH$_2$ and alkyl and alkenyl are unsubstituted or substituted with 1-2 substituents selected from: halogen, —C$_{1-6}$alkyl, and —OC$_{1-6}$alkyl. In another embodiment of the present invention, R$^6$ is selected from the group consisting of: hydrogen, halogen, —C$_{1-6}$ alkyl, and —C$_{2-6}$alkenyl, wherein alkyl and alkenyl are unsubstituted or substituted with 1-2 substituents selected from: halogen, —C$_{1-6}$alkyl, and —OC$_{1-6}$alkyl. In another embodiment of the present invention, R$^6$ is selected from the group consisting of: hydrogen, halogen, and —C$_{1-6}$alkyl, wherein alkyl are unsubstituted or substituted with 1-2 substituents selected from: halogen, —C$_{1-6}$alkyl, and —OC$_{1-6}$alkyl.

In another embodiment of the present invention, R$^6$ is selected from the group consisting of: hydrogen, halogen, and —C$_{1-6}$alkyl. In another embodiment of the present invention, R$^6$ is selected from the group consisting of: hydrogen, and —C$_{1-6}$alkyl. In another embodiment of the present invention, R$^6$ is —C$_{1-6}$alkyl. In another embodiment of the present invention, R$^6$ is hydrogen.

In another embodiment of the present invention, R$^7$ is selected from the group consisting of: hydrogen, halogen, —C$_{1-6}$alkyl, —C$_{2-6}$alkenyl, and —(CH$_2$)$_p$—OH, wherein CH$_2$, alkyl and alkenyl are unsubstituted or substituted with 1-2 substituents selected from: halogen, —C$_{1-6}$alkyl, and —OC$_{1-6}$alkyl.

In another embodiment of the present invention, R$^7$ is selected from the group consisting of: hydrogen, —C$_{1-6}$alkyl, and —C$_{2-6}$alkenyl, wherein alkyl and alkenyl are unsubstituted or substituted with 1-2 substituents selected from: halogen, —C$_{1-6}$alkyl, and —OC$_{1-6}$alkyl. In another embodiment of the present invention, R$^7$ is selected from the group consisting of: hydrogen, and —C$_{2-6}$alkenyl, wherein alkenyl is unsubstituted or substituted with 1-2 substituents selected from: halogen, —C$_{1-6}$alkyl, and —OC$_{1-6}$alkyl. In a class of this embodiment of the present invention, R$^7$ is selected from the group consisting of: hydrogen and —CH$_2$CH=CH$_2$. In another embodiment of the present invention, R$^7$ is selected from the group consisting of: —C$_{2-6}$alkenyl. In a class of this embodiment of the present invention, R$^7$ is —CH$_2$CH=CH$_2$. In another embodiment of the present invention, R$^7$ is hydrogen.

In another embodiment of the present invention, R$^8$ is selected from the group consisting of: hydrogen, halogen, —C$_{1-6}$alkyl, and —(CH$_2$)$_p$—OH, wherein CH$_2$ and alkyl are unsubstituted or substituted with 1-2 substituents selected from: halogen, —C$_{1-6}$alkyl, and —OC$_{1-6}$alkyl. In another embodiment of the present invention, R$^8$ is selected from the group consisting of: hydrogen, and —C$_{1-6}$alkyl, wherein alkyl are unsubstituted or substituted with 1-2 substituents selected from: halogen, —$C_{1-6}$alkyl, and —$OC_{1-6}$alkyl. In another embodiment of the present invention, $R^8$ is selected from the group consisting of: —$C_{1-6}$alkyl, wherein alkyl are unsubstituted or substituted with 1-2 substituents selected from: halogen, —$C_{1-6}$alkyl, and —$OC_{1-6}$alkyl. In another embodiment of the present invention, $R^8$ is selected from the group consisting of: —$C_{1-6}$alkyl. In another embodiment of the present invention, each $R^8$ is hydrogen.

In another embodiment of the present invention, $R^9$ is selected from the group consisting of: hydrogen, halogen, —$C_{1-6}$alkyl, and —$(CH_2)_p$—OH, wherein $CH_2$ and alkyl are unsubstituted or substituted with 1-2 substituents selected from: halogen, —$C_{1-6}$alkyl, and —$OC_{1-6}$alkyl. In another embodiment of the present invention, $R^9$ is selected from the group consisting of: hydrogen, and —$C_{1-6}$alkyl, wherein alkyl are unsubstituted or substituted with 1-2 substituents selected from: halogen, —$C_{1-6}$alkyl, and —$OC_{1-6}$alkyl. In another embodiment of the present invention, $R^9$ is selected from the group consisting of: —$C_{1-6}$alkyl, wherein alkyl are unsubstituted or substituted with 1-2 substituents selected from: halogen, —$C_{1-6}$alkyl, and —$OC_{1-6}$alkyl. In another embodiment of the present invention, $R^9$ is selected from the group consisting of: —$C_{1-6}$alkyl. In another embodiment of the present invention, each $R^9$ is hydrogen.

In another embodiment of the present invention, $R^{10}$ is selected from the group consisting of: hydrogen, halogen, —$C_{1-6}$alkyl, and —$(CH_2)_p$—OH, wherein $CH_2$ and alkyl are unsubstituted or substituted with 1-2 substituents selected from: halogen, —$C_{1-6}$alkyl, and —$OC_{1-6}$alkyl. In another embodiment of the present invention, $R^{10}$ is selected from the group consisting of: hydrogen, and —$C_{1-6}$alkyl, wherein alkyl are unsubstituted or substituted with 1-2 substituents selected from: halogen, —$C_{1-6}$alkyl, and —$OC_{1-6}$alkyl. In another embodiment of the present invention, $R^{10}$ is selected from the group consisting of: —$C_{1-6}$alkyl, wherein alkyl are unsubstituted or substituted with 1-2 substituents selected from: halogen, —$C_{1-6}$alkyl, and —$OC_{1-6}$alkyl. In another embodiment of the present invention, $R^{10}$ is selected from the group consisting of: —$C_{1-6}$alkyl. In another embodiment of the present invention, each $R^{10}$ is hydrogen.

In another embodiment of the present invention, $R^{11}$ is selected from the group consisting of: hydrogen, halogen, —$C_{1-6}$alkyl, and —$(CH_2)_p$—OH, wherein $CH_2$ and alkyl are unsubstituted or substituted with 1-2 substituents selected from: halogen, —$C_{1-6}$alkyl, and —$OC_{1-6}$alkyl. In another embodiment of the present invention, $R^{11}$ is selected from the group consisting of: hydrogen, and —$C_{1-6}$alkyl, wherein alkyl are unsubstituted or substituted with 1-2 substituents selected from: halogen, —$C_{1-6}$alkyl, and —$OC_{1-6}$alkyl. In another embodiment of the present invention, $R^{11}$ is selected from the group consisting of: —$C_{1-6}$alkyl, wherein alkyl are unsubstituted or substituted with 1-2 substituents selected from: halogen, —$C_{1-6}$alkyl, and —$OC_{1-6}$alkyl. In another embodiment of the present invention, $R^{11}$ is selected from the group consisting of: —$C_{1-6}$alkyl. In another embodiment of the present invention, each $R^{11}$ is hydrogen.

In another embodiment of the present invention, $R^{12}$ is selected from the group consisting of: hydrogen, halogen, —$C_{1-6}$alkyl, and —$(CH_2)_p$—OH, wherein $CH_2$ and alkyl are unsubstituted or substituted with 1-2 substituents selected from: halogen, —$C_{1-6}$alkyl, and —$OC_{1-6}$alkyl. In another embodiment of the present invention, $R^{12}$ is selected from the group consisting of: hydrogen, and —$C_{1-6}$alkyl, wherein alkyl are unsubstituted or substituted with 1-2 substituents selected from: halogen, —$C_{1-6}$alkyl, and —$OC_{1-6}$alkyl. In another embodiment of the present invention, $R^{12}$ is selected from the group consisting of: —$C_{1-6}$alkyl, wherein alkyl are unsubstituted or substituted with 1-2 substituents selected from: halogen, —$C_{1-6}$alkyl, and —$OC_{1-6}$alkyl. In another embodiment of the present invention, $R^{12}$ is selected from the group consisting of: —$C_{1-6}$alkyl. In another embodiment of the present invention, each $R^{12}$ is hydrogen.

In another embodiment of the present invention, $R^{13}$ is selected from the group consisting of: hydrogen, halogen, —$C_{1-6}$alkyl, and —$(CH_2)_p$—OH, wherein $CH_2$ and alkyl are unsubstituted or substituted with 1-2 substituents selected from: halogen, —$C_{1-6}$alkyl, and —$OC_{1-6}$alkyl. In another embodiment of the present invention, $R^{13}$ is selected from the group consisting of: hydrogen, and —$C_{1-6}$alkyl, wherein alkyl are unsubstituted or substituted with 1-2 substituents selected from: halogen, —$C_{1-6}$alkyl, and —$OC_{1-6}$alkyl. In another embodiment of the present invention, $R^{13}$ is selected from the group consisting of: —$C_{1-6}$alkyl, wherein alkyl are unsubstituted or substituted with 1-2 substituents selected from: halogen, —$C_{1-6}$alkyl, and —$OC_{1-6}$alkyl. In another embodiment of the present invention, $R^{13}$ is selected from the group consisting of: —$C_{1-6}$alkyl. In another embodiment of the present invention, each $R^{13}$ is hydrogen.

In another embodiment of the present invention, each $R^a$ is independently selected from the group consisting of: halogen, —$C_{1-6}$alkyl, —$OC_{1-6}$alkyl, —$OC_{2-6}$alkenyl, —OH, oxo, —CN, —$NO_2$, —$NR^cR^d$, —$CH_2NR^cR^d$, —$SO_2C_{1-6}$alkyl, —$C_{3-6}$cycloalkyl, —$C_{2-6}$cycloheteroalkyl, aryl, and heteroaryl, wherein —$CH_2$, alkyl, alkenyl, cycloalkyl, cycloheteroalkyl, aryl and heteroaryl are unsubstituted or substituted with 1-4 substituents selected from: halogen, —$C_{1-6}$alkyl, —$OC_{1-6}$alkyl, and —$CO_2C_{1-6}$alkyl. In another embodiment of the present invention, each $R^a$ is independently selected from the group consisting of: halogen, —$C_{1-6}$ alkyl, —$OC_{1-6}$alkyl, —$OC_{2-6}$alkenyl, —OH, oxo, —CN, —$NO_2$, —$NR^cR^d$, —$CH_2NR^cR^d$, —$SO_2C_{1-6}$alkyl, —$C_{3-6}$cycloalkyl, —$C_{2-6}$cycloheteroalkyl, aryl, and heteroaryl, wherein $CH_2$, alkyl, alkenyl, cycloalkyl, cycloheteroalkyl, aryl and heteroaryl are unsubstituted or substituted with 1-4 substituents selected from: halogen.

In another embodiment of the present invention, each $R^a$ is independently selected from the group consisting of: halogen, —$C_{1-6}$alkyl, —$OC_{1-6}$alkyl, oxo, —$NO_2$, —$NR^cR^d$, —$CH_2NR^cR^d$, —$SO_2C_{1-6}$alkyl, —$C_{2-6}$cycloheteroalkyl, and heteroaryl, wherein —$CH_2$, alkyl, cycloheteroalkyl and heteroaryl are unsubstituted or substituted with 1-4 substituents selected from: halogen, —$C_{1-6}$alkyl, —$OC_{1-6}$alkyl, and —$CO_2C_{1-6}$alkyl. In another embodiment of the present invention, each $R^a$ is independently selected from the group consisting of: halogen, —$C_{1-6}$alkyl, —$OC_{1-6}$alkyl, oxo, —$NO_2$, —$NR^cR^d$, —$CH_2NR^cR^d$, —$SO_2C_{1-6}$alkyl, —$C_{2-6}$ cycloheteroalkyl, and heteroaryl, wherein —$CH_2$, alkyl, cycloheteroalkyl and heteroaryl are unsubstituted or substituted with 1-4 substituents selected from: halogen. In another embodiment of the present invention, each $R^a$ is independently selected from the group consisting of: halogen, —$C_{1-6}$alkyl, —$OC_{1-6}$alkyl, oxo, —$NO_2$, —$NR^cR^d$, —$CH_2NR^cR^d$, —$SO_2C_{1-6}$alkyl, —$C_{2-6}$cycloheteroalkyl, and heteroaryl, wherein —$CH_2$, alkyl, cycloheteroalkyl, and heteroaryl are unsubstituted or substituted with 1-4 substituents selected from: F. In another embodiment of the present invention, each $R^a$ is independently selected from the group consisting of: F, Br, Cl, —$CH_3$, —$CF_3$, —$CH(CH_3)_2$, —$OCH_3$, —$OCH_2CH_3$, —$OCHF_2$, oxo, —$NO_2$, —$N(CH_3)_2$, —$CH_2N(CH_3)_2$, —$SO_2CH_3$, morpholine, and pyrrole.

In another embodiment of the present invention, each $R^a$ is independently selected from the group consisting of:

—$C_{1-6}$alkyl, —$OC_{1-6}$alkyl, oxo, and —$NO_2$, wherein alkyl is unsubstituted or substituted with 1-4 substituents selected from: halogen, —$C_{1-6}$alkyl, —$OC_{1-6}$alkyl, and —$CO_2C_{1-6}$ alkyl. In another embodiment of the present invention, each $R^a$ is independently selected from the group consisting of: —$C_{1-6}$alkyl, —$OC_{1-6}$alkyl, oxo, and —$NO_2$, wherein alkyl is unsubstituted or substituted with 1-4 substituents selected from halogen. In another embodiment of the present invention, each $R^a$ is independently selected from the group consisting of: —$C_{1-6}$alkyl, —$OC_{1-6}$alkyl, oxo, and —$NO_2$, wherein alkyl is unsubstituted or substituted with 1-4 substituents selected from F. In another embodiment of the present invention, each $R^a$ is independently selected from the group consisting of: —$CH_3$, —$CF_3$, —$CH(CH_3)_2$, —$OCH_3$, —$OCH_2CH_3$, —$OCHF_2$, oxo, and —$NO_2$.

In another embodiment of the present invention, each $R^a$ is independently selected from the group consisting of: —$CF_3$, —$OCH_3$, oxo, and —$NO_2$.

In another embodiment of the present invention, each $R^b$ is independently selected from the group consisting of: halogen, —$C_{1-6}$alkyl, —$C_{2-6}$alkenyl, —$OC_{1-6}$alkyl, —$OC_{2-6}$ alkenyl, —OH, oxo, —CN, —$NO_2$, —$NR^cR^d$, —$SO_2C_{1-6}$alkyl, —$C_{3-6}$cycloalkyl, —$C_{2-6}$cycloheteroalkyl, aryl, and heteroaryl, wherein alkyl, alkenyl, cycloalkyl, cycloheteroalkyl, aryl and heteroaryl are unsubstituted or substituted with 1-4 substituents selected from: halogen, —$C_{1-6}$alkyl, —$OC_{1-6}$alkyl, and —$CO_2C_{1-6}$alkyl. In another embodiment of the present invention, each $R^b$ is independently selected from the group consisting of: halogen, —$C_{1-6}$ alkyl, —$C_{2-6}$alkenyl, —$OC_{1-6}$alkyl, —$OC_{2-6}$alkenyl, —OH, oxo, —CN, —$NO_2$, —$NR^cR^d$, —$SO_2C_{1-6}$alkyl, —$C_{3-6}$cycloalkyl, —$C_{2-6}$cycloheteroalkyl, aryl, and heteroaryl, wherein alkyl, alkenyl, cycloalkyl, cycloheteroalkyl, aryl and heteroaryl are unsubstituted or substituted with 1-4 substituents selected from: halogen.

In another embodiment of the present invention, each $R^b$ is independently selected from the group consisting of: halogen, —$C_{1-6}$alkyl, —$OC_{1-6}$alkyl, —$OC_{2-6}$alkenyl, —$NR^cR^d$, —$C_{3-6}$cycloalkyl, and —$C_{2-6}$cycloheteroalkyl, wherein alkyl, alkenyl, cycloalkyl, and cycloheteroalkyl are unsubstituted or substituted with 1-4 substituents selected from: halogen, —$C_{1-6}$alkyl, —$OC_{1-6}$alkyl, and —$CO_2C_{1-6}$ alkyl. In another embodiment of the present invention, each $R^b$ is independently selected from the group consisting of: halogen, —$C_{1-6}$alkyl, —$OC_{1-6}$alkyl, —$OC_{2-6}$alkenyl, —$NR^cR^d$, —$C_{3-6}$cycloalkyl, and —$C_{2-6}$cycloheteroalkyl, wherein alkyl, alkenyl, cycloalkyl, and cycloheteroalkyl are unsubstituted or substituted with 1-4 substituents selected from: F. In another embodiment of the present invention, each $R^b$ is independently selected from the group consisting of: F, Br, Cl, —$CH_3$, —$CF_3$, —$CHF_2$, —$C(CH_3)F_2$, —$OCH_3$, —$OCH_2CH_3$, —$OCF_3$, —$OCF_2CH_3$, —$OCH_2CH=CH_2$, —$N(CH_3)_2$, cyclopropyl, and pyrrolidine.

In another embodiment of the present invention, each $R^b$ is independently selected from the group consisting of: halogen, —$C_{1-6}$alkyl, —$OC_{1-6}$alkyl, and —$OC_{2-6}$alkenyl, wherein alkyl, and alkenyl are unsubstituted or substituted with 1-4 substituents selected from: halogen, —$C_{1-6}$alkyl, —$OC_{1-6}$alkyl, and —$CO_2C_{1-6}$alkyl. In another embodiment of the present invention, each $R^b$ is independently selected from the group consisting of: halogen, —$C_{1-6}$alkyl, —$OC_{1-6}$ alkyl, and —$OC_{2-6}$alkenyl, wherein alkyl, and alkenyl are unsubstituted or substituted with 1-4 substituents selected from: F. In another embodiment of the present invention, each $R^b$ is independently selected from the group consisting of: F, Br, Cl, —$CH_3$, —$CF_3$, —$CHF_2$, —$OCH_3$, —$OCH_2CH_3$, —$OCF_3$, —$OCF_2CH_3$, and —$OCH_2CH=CH_2$. In another embodiment of the present invention, each $R^b$ is independently selected from the group consisting of: F, Cl, —$CF_3$, —$OCH_3$, —$OCH_2CH_3$, —$OCF_3$, and —$OCH_2CH=CH_2$.

In another embodiment of the present invention, each $R^b$ is independently selected from the group consisting of: —$C_{1-6}$alkyl, and —$OC_{1-6}$alkyl, wherein alkyl is unsubstituted or substituted with 1-4 substituents selected from: halogen. In another embodiment of the present invention, each $R^b$ is independently selected from the group consisting of: —$C_{1-6}$alkyl, and —$OC_{1-6}$alkyl, wherein alkyl is unsubstituted or substituted with 1-4 substituents selected from: F. In another embodiment of the present invention, each $R^b$ is independently selected from the group consisting of: —$CH_3$, —$CF_3$, —$CHF_2$, —$OCH_3$, —$OCH_2CH_3$, —$OCF_3$, and —$OCF_2CH_3$. In another embodiment of the present invention, each $R^b$ is independently selected from the group consisting of: —$CF_3$, —$OCH_3$, —$OCH_2CH_3$, and —$OCF_3$. In another embodiment of the present invention, each $R^b$ is independently selected from the group consisting of: —$CF_3$, and —$OCH_3$.

In another embodiment of the present invention, each $R^c$ is independently selected from the group consisting of: hydrogen, —$C_{1-6}$alkyl, —$C_{2-6}$alkenyl, —$C_{1-6}$alkyl-OH, —$C_{3-6}$cycloalkyl, —$C(O)C_{1-6}$alkyl, and $SO_2C_{1-6}$alkyl, wherein alkyl, alkenyl and cycloalkyl are unsubstituted or substituted with one to three substituents selected from halogen, —$C_{1-6}$alkyl, —$OC_{1-6}$alkyl, and —$CO_2C_{1-6}$alkyl. In another embodiment of the present invention, each $R^c$ is independently selected from the group consisting of: hydrogen, —$C_{1-6}$alkyl, —$C_{2-6}$alkenyl, —$C_{1-6}$alkyl-OH, —C(O)$C_{1-6}$alkyl, and $SO_2C_{1-6}$alkyl, wherein alkyl and alkenyl are unsubstituted or substituted with one to three substituents selected from halogen.

In another embodiment of the present invention, each $R^c$ is independently selected from the group consisting of: hydrogen, —$C_{1-6}$alkyl, —$C_{2-6}$alkenyl, —$C_{1-6}$alkyl-OH, —C(O)$C_{1-6}$alkyl, and $SO_2C_{1-6}$alkyl, wherein alkyl and alkenyl are unsubstituted or substituted with one to three F substituents.

In another embodiment of the present invention, each $R^c$ is independently selected from the group consisting of: hydrogen and $C_{1-6}$alkyl, wherein alkyl is unsubstituted or substituted with one to three F substituents. In another embodiment of the present invention, each $R^c$ is independently selected from the group consisting of: hydrogen and $C_{1-6}$alkyl. In another embodiment of the present invention, each $R^c$ is independently selected from the group consisting of: hydrogen and $CH_3$.

In another embodiment of the present invention, $R^c$ is hydrogen.

In another embodiment of the present invention, each $R^c$ is independently selected from the group consisting of $C_{1-6}$alkyl, wherein each alkyl is unsubstituted or substituted with one to three F substituents. In another embodiment of the present invention, each $R^c$ is independently selected from the group consisting of $C_{1-6}$alkyl. In another embodiment of the present invention, $R^c$ is $CH_3$.

In another embodiment of the present invention, each $R^d$ is independently selected from the group consisting of: hydrogen, —$C_{1-6}$alkyl, —$C_{2-6}$alkenyl, —$C_{1-6}$alkyl-OH, —$C_{3-6}$cycloalkyl, —$C(O)C_{1-6}$alkyl, and $SO_2C_{1-6}$alkyl, wherein alkyl, alkenyl and cycloalkyl are unsubstituted or substituted with one to three substituents selected from halogen, —$C_{1-6}$alkyl, —$OC_{1-6}$alkyl, and —$CO_2C_{1-6}$alkyl, or $R^c$ and $R^d$ together with the nitrogen atom they are attached to form a C$_{4-8}$cycloheteroalkyl ring, wherein the C$_{4-8}$cycloheteroalkyl ring is unsubstituted or substituted with 1-4 substituents selected from halogen, —C$_{1-6}$alkyl, —OC$_{1-6}$alkyl, and —CO$_2$C$_{1-6}$alkyl. In another embodiment of the present invention, each R$^d$ is independently selected from the group consisting of: hydrogen, —C$_{1-6}$alkyl, —C$_{2-6}$alkenyl, —C$_{1-6}$alkyl-OH, —C$_{3-6}$cycloalkyl, —C(O)C$_{1-6}$alkyl, and SO$_2$C$_{1-6}$alkyl, wherein alkyl, alkenyl and cycloalkyl are unsubstituted or substituted with one to three substituents selected from halogen, —C$_{1-6}$alkyl, —OC$_{1-6}$alkyl, and —CO$_2$C$_{1-6}$alkyl.

In another embodiment of the present invention, each R$^d$ is independently selected from the group consisting of: hydrogen, —C$_{1-6}$alkyl, —C$_{2-6}$alkenyl, —C$_{1-6}$alkyl-OH, —C(O)C$_{1-6}$alkyl, and SO$_2$C$_{1-6}$alkyl, wherein alkyl and alkenyl are unsubstituted or substituted with one to three substituents selected from halogen.

In another embodiment of the present invention, each R$^d$ is independently selected from the group consisting of: hydrogen and C$_{1-6}$alkyl, wherein alkyl is unsubstituted or substituted with one to three F substituents. In another embodiment of the present invention, each R$^d$ is independently selected from the group consisting of: hydrogen and C$_{1-6}$alkyl. In another embodiment of the present invention, each R$^d$ is independently selected from the group consisting of: hydrogen and CH$_3$. In another embodiment of the present invention, R$^d$ is hydrogen.

In another embodiment of the present invention, each R$^d$ is independently selected from the group consisting of C$_{1-6}$alkyl, wherein alkyl is unsubstituted or substituted with one to three F substituents. In another embodiment of the present invention, each R$^d$ is independently selected from the group consisting of C$_{1-6}$alkyl. In another embodiment of the present invention, R$^d$ is CH$_3$.

In another embodiment of the present invention, m is 0 or 1. In a class of this embodiment, m is 0. In another class of this embodiment, m is 1.

In another embodiment of the present invention, n is 0, 1, 2 or 3. In another class of this embodiment, n is 1, 2, or 3. In another class of this embodiment, n is 0, 1, or 2. In another class of this embodiment, n is 1 or 2. In another class of this embodiment, n is 0 or 1. In another class of this embodiment, n is 0 or 2. In another class of this embodiment, n is 0. In another class of this embodiment, n is 1. In another class of this embodiment, n is 2. In another class of this embodiment, n is 3.

In another embodiment of the present invention, p is 0, 1, 2, 3, 4, 5 or 6. In a class of this embodiment, p is 0, 1, 2, 3, or 4. In another class of this embodiment, p is 0, 1, 2, or 3. In another embodiment of the present invention, p is 1, 2, 3, 4, 5 or 6. In another class of this embodiment, p is 1, 2, 3, or 4. In another class of this embodiment, p is 1, 2, or 3. In another class of this embodiment, p is 0, 1 or 2. In another class of this embodiment, p is 0 or 1. In another class of this embodiment, p is 1 or 2. In another class of this embodiment, p is 0. In another class of this embodiment, p is 1. In another class of this embodiment, p is 2.

In another embodiment of the present invention, the invention relates to compounds of structural formula Ia:

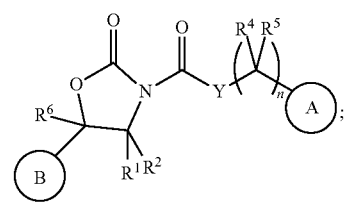

Ia or a pharmaceutically acceptable salt thereof.

In another embodiment of the present invention, the invention relates to compounds of structural formula Ib:

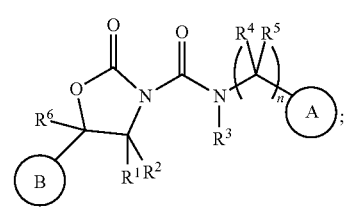

Ib or a pharmaceutically acceptable salt thereof.

In another embodiment of the present invention, the invention relates to compounds of structural formula Ic:

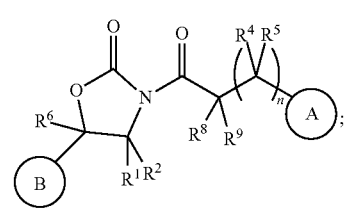

Ic or a pharmaceutically acceptable salt thereof.

In another embodiment of the present invention, the invention relates to compounds of structural formula Id:

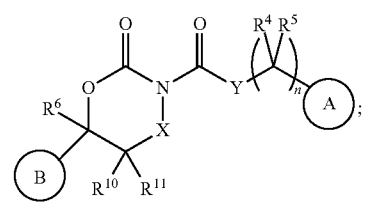

Id or a pharmaceutically acceptable salt thereof.

In another embodiment of the present invention, the invention relates to compounds of structural formula Ie:

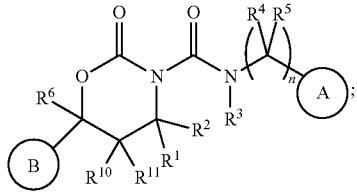

or a pharmaceutically acceptable salt thereof.

In another embodiment of the present invention, the invention relates to compounds of structural formula If:

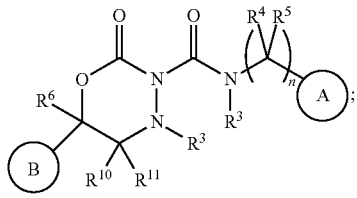

or a pharmaceutically acceptable salt thereof.

In another embodiment of the present invention, the invention relates to compounds of structural formula Ig:

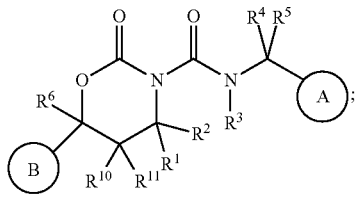

or a pharmaceutically acceptable salt thereof.

In another embodiment of the present invention, the invention relates to compounds of structural formula Ih:

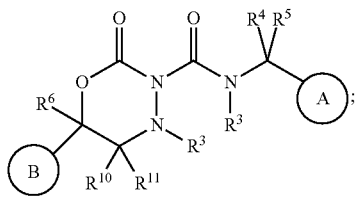

or a pharmaceutically acceptable salt thereof.

The compound of structural formula I, includes the compounds of structural formulas Ia, Ib, Ic, Id, Ie, If, Ig and Ih, and pharmaceutically acceptable salts, hydrates and solvates thereof.

Another embodiment of the present invention relates to compounds of structural formula I wherein:
A is selected from the group consisting of:
  (1) aryl,
  (2) heteroaryl, and
  (3) —O-aryl,
wherein aryl and heteroaryl are unsubstituted or substituted with 1-5 substituents selected from $R^a$;
B is selected from the group consisting of:
  (1) aryl, and
  (2) heteroaryl,
wherein aryl and heteroaryl are unsubstituted or substituted with 1-4 substituents selected from $R^b$;
X is selected from the group consisting of:
  (1) $NR^7$, and
  (2) —$CR^8R^9$;
Y is selected from the group consisting of:
  (1) $NR^3$, and
  (2) —$CR^{10}R^{11}$;
$R^1$ is selected from the group consisting of:
  (1) hydrogen,
  (2) —$C_{1-6}$alkyl, and
  (3) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;
$R^2$ is selected from the group consisting of:
  (1) hydrogen,
  (2) —$C_{1-6}$alkyl, and
  (3) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl, or $R^1$ and $R^2$ together with the carbon atom they are attached to form a $C_{3-6}$cycloalkyl ring, wherein the cycloalkyl ring is unsubstituted or substituted with 1-2 substituents selected from: halogen, —$C_{1-6}$alkyl, and —$OC_{1-6}$alkyl;
$R^3$ is selected from the group consisting of:
  (1) hydrogen, and
  (2) OH;
$R^4$, $R^5$, and $R^6$ are hydrogen;
$R^7$ is selected from the group consisting of:
  (1) hydrogen, and
  (2) —$C_{2-6}$alkenyl,
wherein alkenyl is unsubstituted or substituted with 1-2 substituents selected from: halogen, —$C_{1-6}$alkyl, and —$OC_{1-6}$alkyl;
$R^8$, $R^9$, $R^{10}$, $R^{11}$, $R^{12}$ and $R^{13}$ are hydrogen; and
m is 0 or 1;
or a pharmaceutically acceptable salt thereof.

Another embodiment of the present invention relates to compounds of structural formula I wherein:
A is selected from the group consisting of:
  (1) aryl, and
  (2) heteroaryl,
wherein aryl and heteroaryl are unsubstituted or substituted with 1-5 substituents selected from $R^a$;
B is selected from the group consisting of:
  (1) aryl, and
  (2) heteroaryl,
wherein aryl and heteroaryl are unsubstituted or substituted with 1-4 substituents selected from $R^b$;

X is selected from the group consisting of:
- (1) NR⁷, and
- (2) —CR⁸R⁹;

Y is NR³;

R¹ is selected from the group consisting of:
- (1) hydrogen, and
- (2) —$C_{1-6}$alkyl, wherein alkyl is unsubstituted or substituted with 1-2 substituents selected from: halogen, —$C_{1-6}$alkyl, and —$OC_{1-6}$alkyl;

R² is selected from the group consisting of:
- (1) hydrogen,
- (2) —$C_{1-6}$alkyl, and
- (3) —$(CH_2)_p$—OH, wherein $CH_2$ and alkyl are unsubstituted or substituted with 1-2 substituents selected from: halogen, —$C_{1-6}$alkyl, and —$OC_{1-6}$alkyl;

R³ is hydrogen;

R⁴, R⁵, R⁶, R⁷, R⁸, R⁹, R¹⁰, R¹¹, R¹² and R¹³ are hydrogen; and m is 0 or 1;

or a pharmaceutically acceptable salt thereof.

Illustrative, but non-limiting, examples of the compounds of the present invention that are useful as inhibitors of TarO are the following compounds:

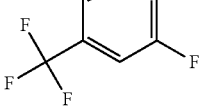

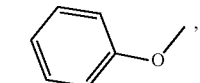

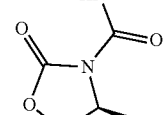

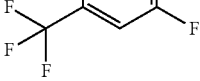

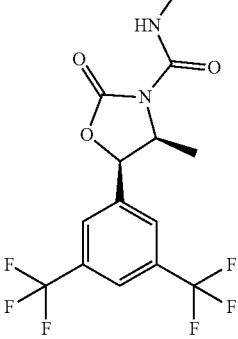

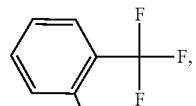

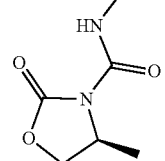

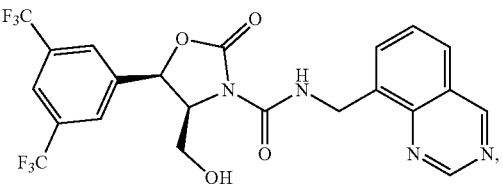

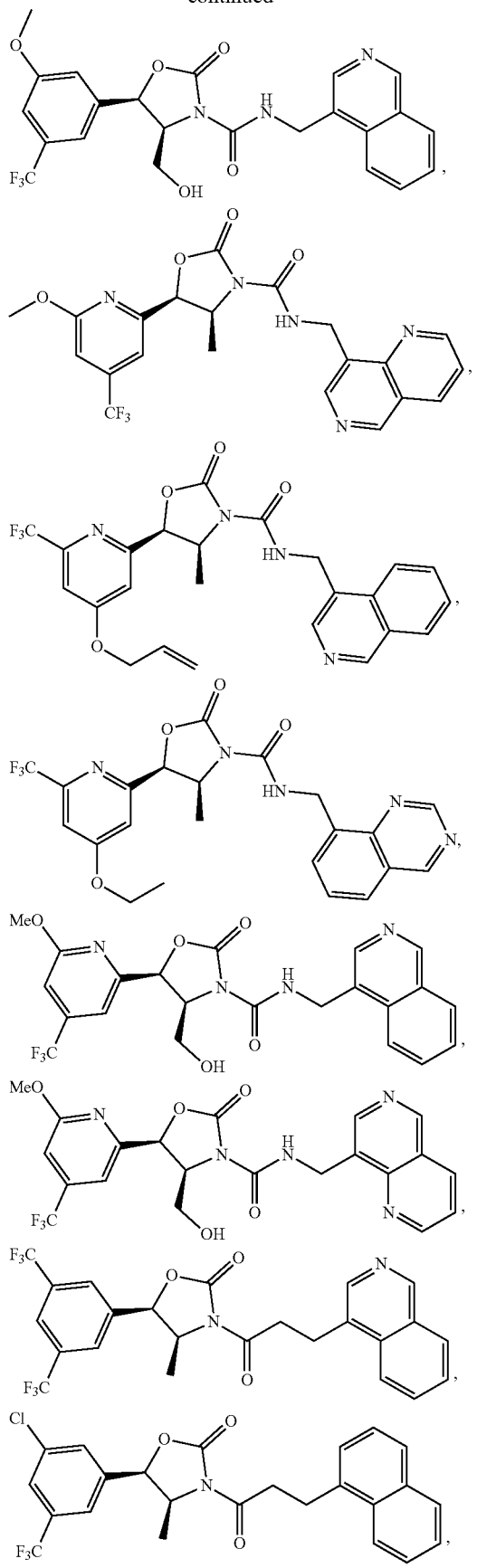
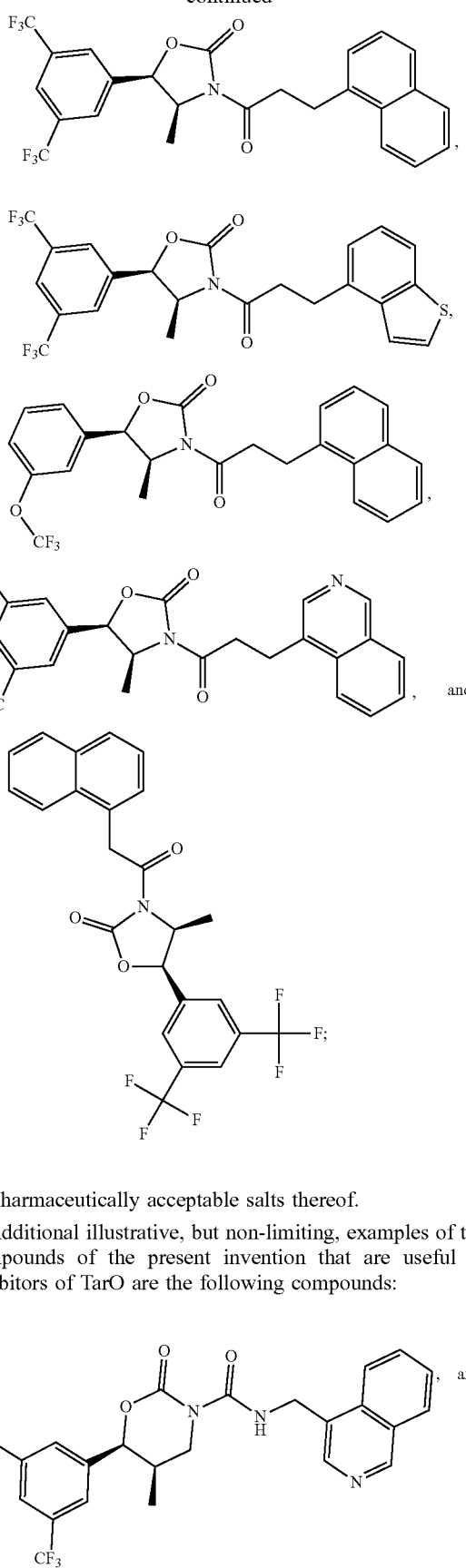
or pharmaceutically acceptable salts thereof.
Additional illustrative, but non-limiting, examples of the compounds of the present invention that are useful as inhibitors of TarO are the following compounds:
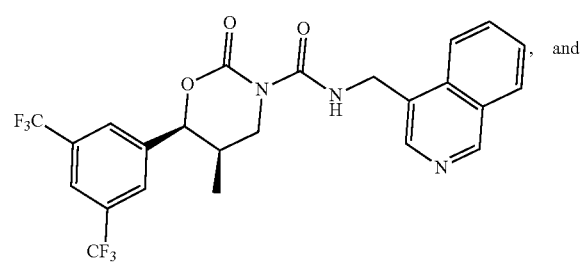

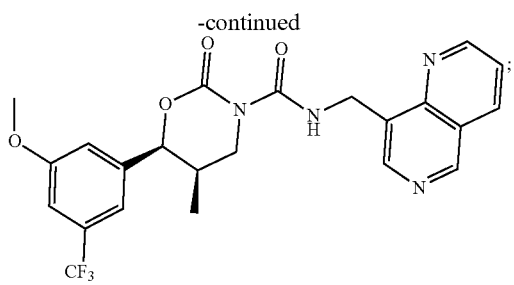

or pharmaceutically acceptable salts thereof.

Although the specific stereochemistries described above are preferred, other stereoisomers, including diastereoisomers, enantiomers, epimers, and mixtures of these may also have utility in treating TarO mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is $CH_3C(=O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Cycloalkyl" means a saturated monocyclic, bicyclic, tricyclic, bridged or spirocyclic carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. In one embodiment of the present invention, cycloalkyl is selected from: cyclohexane and norbornane. In another embodiment of the present invention, cycloalkyl is adamantane. In another embodiment of the present invention, cycloalkyl is cyclopropyl.

"Cycloheteroalkyl" means a saturated or partly unsaturated non-aromatic monocyclic, bicyclic, tricyclic, bridged or spirocyclic carbocyclic ring or ring system containing at least one ring heteroatom selected from N, NH, S (including SO and $SO_2$) and O. The cycloheteroalkyl ring may be substituted on the ring carbons and/or the ring nitrogen(s). Examples of cycloheteroalkyl include tetrahydrofuran, pyrrolidine, tetrahydrothiophene, azetidine, piperazine, piperidine, morpholine, oxetane and tetrahydropyran. In one embodiment of the present invention, cycloheteroalkyl is selected from: morpholine, pyrrolidine, piperazine and tetrahydrofuran. In another embodiment of the present invention, cycloheteroalkyl is selected from: pyrrolidine and piperidine.

"Aryl" means a monocyclic, bicyclic, tricyclic, bridged or spirocyclic aromatic ring or ring system containing 5-14 carbon atoms, wherein at least one of the rings is aromatic. The term may also be used to describe a ring system in which a cycloalkyl and/or cycloheteroalkyl ring is fused to an aryl group. Examples of aryl include phenyl, naphthyl, and tetrahydronaphthalene. In one embodiment of the present invention, aryl is phenyl, naphthalene and tetralin. In another embodiment of the present invention, aryl is phenyl, and naphthalene. In another embodiment of the present invention, aryl is phenyl. In another embodiment of the present invention, aryl is naphthalene. In another embodiment of the present invention, aryl is tetralin.

"Heteroaryl" means monocyclic, bicyclic, tricyclic, bridged or spirocyclic ring or ring system containing 5-14 carbon atoms and containing at least one ring heteroatom selected from N, NH, S (including SO and $SO_2$) and O, wherein at least one of the heteroatom containing rings is aromatic. The term may also be used to describe a ring system in which a cycloalkyl ring and/or a cycloheteroalkyl ring is fused to a heteroaryl group. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl, quinolyl, indolyl, isoquinolyl, quinazolinyl, dibenzofuranyl, isoindoline, isoindoline-1-one, benzo[b][1,4]oxazine, 2H-benzo[b][1,4]oxazin-3(4H)-one, benzo[d]oxazole. benzo[d]oxazol-2(3H)-one, and the like. In one embodiment of the present invention, heteroaryl is selected from: isoquinoline, pyrazolopyridine, naphthyridine, quinoxaline, dihydrobenzo-dioxine or benzodioxane, indole, indazole, thienopyridine, furopyridine, thiazole, quinoline, pyridine, pyrazole, quinazoline, dihydroisoindole, dihydrocyclopentan[b]pyridine, imidazo-thiazole, dihydropyridooxazine, and benzothiophene. In another embodiment, heteroaryl is selected from: isoindoline-1-one, 2H-benzo[b][1,4]oxazin-3(4H)-one, and benzo[d]oxazol-2(3H)-one. In another embodiment of the present invention, heteroaryl is selected from: isoquinoline, pyrazolo[1,5-a]pyridine, 1,6-naphthyridine, quinoxaline, 2,3-dihydro-1,4-benzodioxine or benzodioxane, indole, thieno[3,2-c]pyridine, furo[2,3-c]pyridine, thiazole, quinoline, pyridine, pyrazole, quinazoline, 2,3-dihydroisoindole, 6,7-dihydro-5H-cyclo-pentan[b]pyridine, imidazo[2,1-b][1,3]thiazole, 2,3-dihydropyrido[3,2-b][1,4]oxazine, and benzothiophene. In another embodiment of the present invention, heteroaryl is selected from: isoquinoline, pyrazolo[1,5-a]pyridine, 1,6-naphthyridine, quinazoline, and benzothiophene. In another embodiment of the present invention, heteroaryl is selected from: isoquinoline, and 1,6-naphthyridine. In another embodiment of the present invention, heteroaryl is isoquinoline. In another embodiment of the present invention, heteroaryl is pyrazolo[1,5-a]pyridine. In another embodiment of the present invention, heteroaryl is 1,6-naphthyridine. In another embodiment of the present invention, heteroaryl is quinazoline. In another embodiment of the present invention, heteroaryl is benzothiophene.

"Halogen" includes fluorine, chlorine, bromine and iodine.

"Me" represents methyl.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

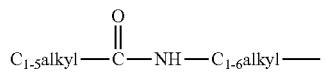

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to encompass all such isomeric forms of the compounds of Formula I.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixtures thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium (1H), deuterium (2H), and tritium (3H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that the present invention includes compounds of the present invention and the pharmaceutically acceptable salts thereof. The present invention also includes salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are TarO inhibitors, and may be useful to treat diseases that are modulated by TarO inhibitors. Many of these diseases are summarized below.

The compounds of the present invention, and pharmaceutically acceptable salts thereof, may be useful for the treatment, prevention or suppression of a bacterial infection, including but not limited to, a gram negative bacterial infection, a gram-positive bacterial infection, a methicillin-resistant S. aureus (MRSA) bacterial infection, and/or a methicillin-resistant S. epidermidis (MRSE) bacterial infection.

The compounds of the present invention, and pharmaceutically acceptable salts thereof, may also be useful to sensitize bacteria to a subject's innate immune response and enhance bacterial clearance by the subject's immune system, including but not limited to gram negative bacteria, gram positive bacteria, MRSA bacteria and MRSE bacteria.

Further, the compounds of the present invention, and pharmaceutically acceptable salts thereof, in combination with a β-lactam antibiotic, may be useful for the treatment, prevention or suppression of a bacterial infection, including but not limited to, a gram-positive bacterial infection, a methicillin-resistant S. aureus (MRSA) bacterial infection, and/or a methicillin-resistant S. epidermidis (MRSE) bacterial infection.

Further, the compounds of the present invention, and pharmaceutically acceptable salts thereof, may also be useful in combination with a β-lactam antibiotic, including but not limited to a penicillin antibiotic, a cephamycin antibiotic, a cephalosporin antibiotic or a carbapenem antibiotic, for the treatment of bacterial infections, particularly antibiotic resistant gram negative and/or gram positive bacterial infections such as MRSA infections and/or MRSE infections.

In particular, the compounds of the present invention, and pharmaceutically acceptable salts thereof, may be useful in combination with imipenem for the treatment of bacterial infections, particularly antibiotic resistant gram negative and/or gram positive bacterial infections such as MRSA infections, and/or MRSE infections.

In particular, the compounds of the present invention, and pharmaceutically acceptable salts thereof, may also be useful in combination with dicloxacillin for the treatment of bacterial infections, particularly antibiotic resistant gram negative and/or gram positive bacterial infections such as MRSA infections and/or MRSE infections.

The compounds of the present invention, or pharmaceutically acceptable salts thereof, alone or in combinations with a β-lactam antibiotic, may be effective in restoring bacterial susceptibility to treatment with a β-lactam antibiotic in a subject, including but not limited to, decreasing gram negative susceptibility, gram positive bacterial susceptibility, methicillin-resistant S. aureus (MRSA) bacterial susceptibility, and/or methicillin-resistant S. epidermidis (MRSE) bacterial susceptibility.

The compounds of the present invention, or pharmaceutically acceptable salts thereof, alone or in combinations with a β-lactam antibiotic, may also be effective in restoring bacterial susceptibility to treatment with a β-lactam antibiotic in a bacterial cell culture, including but not limited to, decreasing gram negative susceptibility, gram positive bacterial susceptibility, methicillin-resistant S. aureus (MRSA) bacterial susceptibility, and/or methicillin-resistant S. epidermidis (MRSE) bacterial susceptibility.

The compounds of the present invention, or pharmaceutically acceptable salts thereof, alone or in combinations with a β-lactam antibiotic, may be effective in decreasing bacterial resistance to treatment with a β-lactam antibiotic in a subject, including but not limited to, decreasing gram negative bacterial resistance, decreasing gram positive bacterial resistance, methicillin-resistant *S. aureus* (MRSA) bacterial resistance, and/or methicillin-resistant *S. epidermidis* (MRSE) bacterial resistance.

The compounds of the present invention, or pharmaceutically acceptable salts thereof, alone or in combination with a β-lactam antibiotic may be effective in treating highly resistant infections in a subject, including but not limited to, gram negative bacterial infections, gram positive bacterial infections, methicillin-resistant *S. aureus* (MRSA) bacterial infections, and/or methicillin-resistant *S. epidermidis* (MRSE) bacterial infections.

The compounds of the present invention, or pharmaceutically acceptable salts thereof, alone or in combination with a β-lactam antibiotic may be effective in increasing β-lactam antibiotic effectiveness to treat a bacterial infection in a subject, including but not limited to, a gram negative bacterial infection, a gram positive bacterial infection, a methicillin-resistant *S. aureus* (MRSA) bacterial infection, and/or a methicillin-resistant *S. epidermidis* (MRSE) bacterial infection.

The compounds of the present invention, or pharmaceutically acceptable salts thereof, in combination with a β-lactam antibiotic may increase bacterial susceptibility to treatment with a β-lactam antibiotic in a subject, wherein the bacteria includes but is not limited to gram negative bacteria, gram positive bacteria, methicillin-resistant *S. aureus* (MRSA) bacteria, and/or methicillin-resistant *S. epidermidis* (MRSE) bacteria.

The compounds of the present invention, or pharmaceutically acceptable salts thereof, in combination with a β-lactam antibiotic may provide bactericidal synergy against bacterial infections in a subject, including but not limited to, gram negative bacterial infections, gram positive bacterial infections, methicillin-resistant *S. aureus* (MRSA) bacterial infections, and/or methicillin-resistant *S. epidermidis* (MRSE) bacterial infections.

The compounds of this invention, or pharmaceutically acceptable salts thereof, alone or in combination with a β-lactam antibiotic, may also have utility in lowering the bacterial load in a subject. In particular, the compounds of this invention, or pharmaceutically acceptable salts thereof, may have utility in lowering the bacterial level in a subject, alone or in combination with imipenem or dicloxacillin.

The compounds of the present invention may be useful for the treatment or prevention of one or more of the following diseases by administering a therapeutically effective amount or a prophylactically effective amount of the compound of formula I, or a pharmaceutically acceptable salt thereof, to a patient in need of treatment:
(1) bacterial infections;
(2) gram negative bacterial infections;
(3) gram positive bacterial infections;
(4) methicillin-resistant *S. aureus* (MRSA) infections; and
(5) methicillin-resistant *S. epidermidis* (MRSE) infections.

One or more of these diseases may be treated by the administration of a therapeutically effective amount of a compound of the present invention, or a pharmaceutically acceptable salt thereof, to a patient in need of treatment. Further, one or more of these diseases may be prevented by the administration of a prophylactically effective amount of a compound of the present invention, or a pharmaceutically acceptable salt thereof, to a patient in need of treatment.

The compounds of the present invention may be useful for the treatment or prevention of one or more of the following diseases by administering a therapeutically effective or prophylactically effective amount of the compound of formula I, or a pharmaceutically acceptable salt thereof, and a β-lactam antibiotic, including but not limited to a penicillin antibiotic, a cephamycin antibiotic, a cephalosporin antibiotic or a carbapenem antibiotic, to a patient in need of treatment.
(1) bacterial infections;
(2) gram negative bacterial infections;
(3) gram positive bacterial infections;
(4) methicillin-resistant *S. aureus* (MRSA) infections; and
(5) methicillin-resistant *S. epidermidis* (MRSE) infections.

One or more of these diseases may be treated by the administration of a therapeutically effective amount of a compound of the present invention, or a pharmaceutically acceptable salt thereof, and a β-lactam antibiotic selected from: a penicillin antibiotic, a cephamycin antibiotic, a cephalosporin antibiotic and a carbapenem antibiotic, to a patient in need of treatment. Further, one or more of these diseases may be prevented by the administration of a prophylactically effective amount of a compound of the present invention, or a pharmaceutically acceptable salt thereof, and a β-lactam antibiotic selected from: a penicillin antibiotic, a cephamycin antibiotic, a cephalosporin antibiotic and a carbapenem antibiotic, to a patient in need of treatment.

In particular, the compounds of the present invention may also be useful for the treatment or prevention of one or more of the following diseases by administering a therapeutically effective amount or prophylactically effective amount of the compound of formula I, or a pharmaceutically acceptable salt thereof, and dicloxacillin to a patient in need of treatment:
(1) bacterial infections;
(2) gram negative bacterial infections;
(3) gram positive bacterial infections;
(4) methicillin-resistant *S. aureus* (MRSA) infections; and
(5) methicillin-resistant *S. epidermidis* (MRSE) infections.

One or more of these diseases may be treated by the administration of a therapeutically effective amount of a compound of the present invention, or a pharmaceutically acceptable salt thereof, and dicloxacillin, or a pharmaceutically acceptable salt or prodrug thereof, to a patient in need of treatment. Further, one or more of these diseases may be prevented by the administration of a prophylactically effective amount of a compound of the present invention, or a pharmaceutically acceptable salt thereof, and dicloxacillin, or a pharmaceutically acceptable salt or prodrug thereof, to a patient in need of treatment.

In particular, the compounds of the present invention may also be useful for the treatment or prevention of one or more of the following diseases by administering a therapeutically effective amount or prophylactically effective amount of the compound of formula I, or a pharmaceutically acceptable salt thereof, and imipenem to a patient in need of treatment:
(1) bacterial infections;
(2) gram negative bacterial infections;
(3) gram positive bacterial infections;
(4) methicillin-resistant *S. aureus* (MRSA) infections; and
(5) methicillin-resistant *S. epidermidis* (MRSE) infections.

One or more of these diseases may be treated by the administration of a therapeutically effective amount of a compound of the present invention, or a pharmaceutically acceptable salt thereof, and imipenem, or a pharmaceutically acceptable salt or prodrug thereof, to a patient in need of treatment. Further, one or more of these diseases may be prevented by the administration of a prophylactically effective amount of a compound of the present invention, or a pharmaceutically acceptable salt thereof, and imipenem, or a pharmaceutically acceptable salt or prodrug thereof, to a patient in need of treatment.

The compounds of the present invention, alone or in combination with a β-lactam antibiotic, may be useful in the following methods of treatment.

In another embodiment, the present invention relates to a method of treating or preventing a disorder, condition or disease that is responsive to the inhibition of TarO in a patient in need thereof comprising administration of a therapeutically effective amount of a compound according to Claims 1-14, or a pharmaceutically acceptable salt thereof.

In another embodiment, the present invention relates to a method of treating a bacterial infection in a patient in need of treatment comprising the administration to the patient of a therapeutically effective amount of a compound of Claims 1-14, or a pharmaceutically acceptable salt thereof. In a class of this embodiment, the bacterial infection is a methicillin-resistant *S. aureus* infection or a methicillin-resistant *S. epidermidis* infection.

In another embodiment, the present invention relates to a method of treating a bacterial infection in a patient in need of treatment comprising the administration to the patient of a therapeutically effective amount of a compound of Claims 1-14, or a pharmaceutically acceptable salt thereof, in combination with a β-lactam antibiotic, or a pharmaceutically acceptable salt thereof. In a class of this embodiment, the bacterial infection is a methicillin-resistant *S. aureus* infection or a methicillin-resistant *S. epidermidis* infection. In another class of this embodiment, the β-lactam antibiotic is imipenem or dicloxacillin.

A method of treating a bacterial infection comprising the administration of a therapeutically effective amount of a compound of formula I, or a pharmaceutically acceptable salt thereof, to a patient in need of treatment. In one embodiment, the bacterial infection is a gram positive bacterial infection. In another embodiment, the bacterial infection is a gram negative bacterial infection. In another embodiment, the bacterial infection is a MRSA infection. In another embodiment, the bacterial infection is a MRSE infection.

A method of treating a bacterial infection comprising administration of a therapeutically effective amount of a compound of formula I, or a pharmaceutically acceptable salt thereof, and a therapeutically effective amount of a β-lactam antibiotic, or a pharmaceutically acceptable salt thereof, to a patient in need of treatment. In one embodiment the β-lactam antibiotic is selected from: a penicillin antibiotic, a cephamycin antibiotic, a cephalosporin antibiotic or a carbapenem antibiotic. In another embodiment, the β-lactam antibiotic is selected from: a penicillin antibiotic and a carbapenem antibiotic. In another embodiment, the β-lactam antibiotic is a penicillin antibiotic. In a class of this embodiment, the penicillin antibiotic is dicloxacillin. In another embodiment, the β-lactam antibiotic is a carbapenem antibiotic. In a class of this embodiment, the carbapenem antibiotic is imipenem.

A method of treating a gram negative and/or a gram positive bacterial infection comprising administration of a therapeutically effective amount of a compound of formula I, or a pharmaceutically acceptable salt thereof, and a therapeutically effective amount of a β-lactam antibiotic, or a pharmaceutically acceptable salt thereof, to a patient in need of treatment. In one embodiment the β-lactam antibiotic is selected from: a penicillin antibiotic, a cephamycin antibiotic, a cephalosporin antibiotic or a carbapenem antibiotic. In another embodiment, the β-lactam antibiotic is selected from: a penicillin antibiotic and a carbapenem antibiotic. In another embodiment, the β-lactam antibiotic is a penicillin antibiotic. In a class of this embodiment, the penicillin antibiotic is dicloxacillin. In another class of this embodiment, the bacterial infection is a gram positive bacterial infection and the penicillin antibiotic is dicloxacillin. In another embodiment, the β-lactam antibiotic is a carbapenem antibiotic. In a class of this embodiment, the carbapenem antibiotic is imipenem. In another class of this embodiment, the bacterial infection is a gran negative bacterial infection and a gram positive bacterial infection and the carbapenem antibiotic is imipenem. In another class of this embodiment, the bacterial infection is a gran negative bacterial infection and the carbapenem antibiotic is imipenem. In another class of this embodiment, the bacterial infection is a gram positive bacterial infection and the carbapenem antibiotic is imipenem.

A method of treating MRSA infection comprising administration of a therapeutically effective amount of a compound of formula I, or a pharmaceutically acceptable salt thereof, and a therapeutically effective amount of a β-lactam antibiotic, or a pharmaceutically acceptable salt thereof, to a patient in need of treatment. In one embodiment the β-lactam antibiotic is selected from: a penicillin antibiotic, a cephamycin antibiotic, a cephalosporin antibiotic or a carbapenem antibiotic. In another embodiment, the β-lactam antibiotic is selected from: a penicillin antibiotic and a carbapenem antibiotic. In another embodiment, the β-lactam antibiotic is a penicillin antibiotic. In a class of this embodiment, the penicillin antibiotic is dicloxacillin. In another embodiment, the β-lactam antibiotic is a carbapenem antibiotic. In a class of this embodiment, the carbapenem antibiotic is imipenem.

A method of treating MRSE infection comprising administration of a therapeutically effective amount of a compound of formula I, or a pharmaceutically acceptable salt thereof, and a therapeutically effective amount of a β-lactam antibiotic, or a pharmaceutically acceptable salt thereof, to a patient in need of treatment. In one embodiment the β-lactam antibiotic is selected from: a penicillin antibiotic, a cephamycin antibiotic, a cephalosporin antibiotic or a carbapenem antibiotic. In another embodiment, the β-lactam antibiotic is selected from: a penicillin antibiotic and a carbapenem antibiotic. In another embodiment, the β-lactam antibiotic is a penicillin antibiotic. In a class of this embodiment, the penicillin antibiotic is dicloxacillin. In another embodiment, the β-lactam antibiotic is a carbapenem antibiotic. In a class of this embodiment, the carbapenem antibiotic is imipenem.

A method of treating a bacterial infection by sensitizing the bacteria to the subject's immune system response comprising the administration of a therapeutically effective amount of a compound of formula I, or a pharmaceutically acceptable salt thereof, to a patient in need of treatment. In one embodiment, the bacterial infection is a gram positive bacterial infection. In another embodiment, the bacterial infection is a gram negative bacterial infection. In another embodiment, the bacterial infection is a MRSA infection. In another embodiment, the bacterial infection is a MRSE infection.

A method of preventing a bacterial infection comprising the administration of a prophylactically effective amount of a compound of formula I, or a pharmaceutically acceptable salt thereof, to a patient in need of treatment. In one embodiment, the bacterial infection is a gram positive bacterial infection. In another embodiment, the bacterial infection is a gram negative bacterial infection. In another embodiment, the bacterial infection is a MRSA infection. In another embodiment, the bacterial infection is a MRSE infection.

A method of preventing a bacterial infection comprising administration of a prophylactically effective amount of a compound of formula I, or a pharmaceutically acceptable salt thereof, and a prophylactically effective amount of a β-lactam antibiotic, or a pharmaceutically acceptable salt thereof, to a patient in need of treatment. In one embodiment the β-lactam antibiotic is selected from: a penicillin antibiotic, a cephamycin antibiotic, a cephalosporin antibiotic or a carbapenem antibiotic. In another embodiment, the β-lactam antibiotic is selected from: a penicillin antibiotic and a carbapenem antibiotic. In another embodiment, the β-lactam antibiotic is a penicillin antibiotic. In a class of this embodiment, the penicillin antibiotic is dicloxacillin. In another embodiment, the β-lactam antibiotic is a carbapenem antibiotic. In a class of this embodiment, the carbapenem antibiotic is imipenem.

A method of preventing a gram negative and/or a gram positive bacterial infection comprising administration of a prophylactically effective amount of a compound of formula I, or a pharmaceutically acceptable salt thereof, and a prophylactically effective amount of a β-lactam antibiotic, or a pharmaceutically acceptable salt thereof, to a patient in need of treatment. In one embodiment the β-lactam antibiotic is selected from: a penicillin antibiotic, a cephamycin antibiotic, a cephalosporin antibiotic or a carbapenem antibiotic. In another embodiment, the β-lactam antibiotic is selected from: a penicillin antibiotic and a carbapenem antibiotic. In another embodiment, the β-lactam antibiotic is a penicillin antibiotic. In a class of this embodiment, the penicillin antibiotic is dicloxacillin. In another class of this embodiment, the bacterial infection is a gram positive bacterial infection and the penicillin antibiotic is dicloxacillin. In another embodiment, the β-lactam antibiotic is a carbapenem antibiotic. In a class of this embodiment, the carbapenem antibiotic is imipenem. In another class of this embodiment, the bacterial infection is a gram positive and/or a gram negative bacterial infection and the carbapenem antibiotic is imipenem. In another class of this embodiment, the bacterial infection is a gram positive bacterial infection and the carbapenem antibiotic is imipenem. In another class of this embodiment, the bacterial infection is a gram negative bacterial infection and the carbapenem antibiotic is imipenem.

A method of preventing a MRSA infection comprising administration of a prophylactically effective amount of a compound of formula I, or a pharmaceutically acceptable salt thereof, and a prophylactically effective amount of a β-lactam antibiotic, or a pharmaceutically acceptable salt thereof, to a patient in need of treatment. In one embodiment the β-lactam antibiotic is selected from: a penicillin antibiotic, a cephamycin antibiotic, a cephalosporin antibiotic or a carbapenem antibiotic. In another embodiment, the β-lactam antibiotic is selected from: a penicillin antibiotic and a carbapenem antibiotic. In another embodiment, the β-lactam antibiotic is a penicillin antibiotic. In a class of this embodiment, the penicillin antibiotic is dicloxacillin. In another embodiment, the β-lactam antibiotic is a carbapenem antibiotic. In a class of this embodiment, the carbapenem antibiotic is imipenem.

A method of preventing a MRSE infection comprising administration of a prophylactically effective amount of a compound of formula I, or a pharmaceutically acceptable salt thereof, and a prophylactically effective amount of a β-lactam antibiotic, or a pharmaceutically acceptable salt thereof, to a patient in need of treatment. In one embodiment the β-lactam antibiotic is selected from: a penicillin antibiotic, a cephamycin antibiotic, a cephalosporin antibiotic or a carbapenem antibiotic. In another embodiment, the β-lactam antibiotic is selected from: a penicillin antibiotic and a carbapenem antibiotic. In another embodiment, the β-lactam antibiotic is a penicillin antibiotic. In a class of this embodiment, the penicillin antibiotic is dicloxacillin. In another embodiment, the β-lactam antibiotic is a carbapenem antibiotic. In a class of this embodiment, the carbapenem antibiotic is imipenem.

A method of preventing a bacterial infection by sensitizing the bacteria to the patient's immune system response comprising administration of a prophylactically effective amount of a compound of formula I, or a pharmaceutically acceptable salt thereof, and a prophylactically effective amount of a β-lactam antibiotic, or a pharmaceutically acceptable salt thereof, to a patient in need of treatment. In one embodiment, the bacterial infection is a gram positive bacterial infection. In another embodiment the bacterial infection is a gram negative bacterial infection. In another embodiment, the bacterial infection is a MRSA infection. In another embodiment, the bacterial infection is a MRSE infection. In another embodiment the β-lactam antibiotic is selected from: a penicillin antibiotic, a cephamycin antibiotic, a cephalosporin antibiotic or a carbapenem antibiotic. In another embodiment, the β-lactam antibiotic is selected from: a penicillin antibiotic and a carbapenem antibiotic. In another embodiment, the β-lactam antibiotic is a penicillin antibiotic. In a class of this embodiment, the penicillin antibiotic is dicloxacillin. In another embodiment, the β-lactam antibiotic is a carbapenem antibiotic. In a class of this embodiment, the carbapenem antibiotic is imipenem.

The invention also includes pharmaceutically acceptable salts of the compounds of formula I, and pharmaceutical compositions comprising the compounds of formula I, or pharmaceutically acceptable salts thereof, and a pharmaceutically acceptable carrier.

The invention also includes pharmaceutically acceptable salts of the compounds of formula I, and pharmaceutical compositions comprising the compounds of formula I, or pharmaceutically acceptable salts thereof, in combination with a β-lactam antibiotic, and a pharmaceutically acceptable carrier.

Other embodiments of the present invention include the following:

(a) A pharmaceutical composition comprising an effective amount of a compound of Formula I as defined above, or a pharmaceutically acceptable salt thereof, and a pharmaceutically acceptable carrier.

(b) The pharmaceutical composition of (a), further comprising an effective amount of a β-lactam antibiotic.

(c) The pharmaceutical composition of (b), wherein the beta-lactam antibiotic is selected from the group consisting of methicillin, oxacillin, penicillin G, dicloxacillin, nafcillin, cefepime, cefoxitin, cefuroxime, imipenem, doripenem, meropenem, and tebipenem.

(d) The pharmaceutical composition of (b), wherein the beta-lactam antibiotic is selected from the group consisting of: imipenem and dicloxacillin.

(e) The pharmaceutical composition of (b), wherein the β-lactam antibiotic is imipenem.

(f) The pharmaceutical composition of (b), wherein the β-lactam antibiotic is dicloxacillin.

(g) A combination of therapeutically effective amounts of a compound of Formula I as defined above, or a pharmaceutically acceptable salt thereof, and a β-lactam antibiotic.

(h) The combination of (g), wherein the beta-lactam antibiotic is selected from the group consisting of methicillin, oxacillin, penicillin G, dicloxacillin, naficillin, cefepime, cefoxitin, cefuroxime, imipenem, doripenem, meropenem, and tebipenem.

(i) The combination of (g), wherein the beta-lactam antibiotic is selected from the group consisting of imipenem, and dicloxacillin.

(j) The combination of (g), wherein the β-lactam antibiotic is imipenem.

(k) The combination of (g), wherein the β-lactam antibiotic is dicloxacillin.

(l) A method for treating a bacterial infection comprising administering to a subject in need of such treatment a therapeutically effective amount of a compound of Formula I, or a pharmaceutically acceptable salt thereof, optionally in combination with an effective amount of a beta-lactam antibiotic.

(m) A method for treating a bacterial infection comprising administering to a subject in need of such treatment a therapeutically effective amount of the composition of (a), (b), (c), (d), (e), (f), (g), (i), (j) and (k).

(n) A method for treating a bacterial infection comprising administering to a subject in need of such treatment a therapeutically effective amount of the combination (j), and (k).

(o) The method of treating a bacterial infection as set forth in (m), or (n), wherein the bacterial infection is due to gram positive bacteria and/or gram negative bacteria.

(p) The method of treating a bacterial infection as set forth in (m), or (n), wherein the bacterial infection is due to methicillin-resistant *S. aureus* (MRSA) or methicillin-resistant *S. epidermidis* (MRSE).

(q) A method for preventing a bacterial infection comprising administering to a subject in need of such treatment a prophylactically effective amount of a compound of Formula I, or a pharmaceutically acceptable salt thereof, optionally in combination with an effective amount of a beta-lactam antibiotic.

(r) A method for preventing a bacterial infection comprising administering to a subject in need of such treatment a prophylactically effective amount of the composition of (a), (b), (c), (d), (e), (f), (g), (i), (j) and (k).

(s) A method for preventing a bacterial infection comprising administering to a subject in need of such treatment a prophylactically effective amount of the combination (j), and (k).

(t) The method of preventing a bacterial infection as set forth in (q), or (r), wherein the bacterial infection is due to gram positive bacteria and/or gram negative bacteria.

(u) The method of preventing a bacterial infection as set forth in (q), or (r), wherein the bacterial infection is due to methicillin-resistant *S. aureus* (MRSA) or methicillin-resistant *S. epidermidis* (MRSE).

The compounds of the present invention, and pharmaceutically acceptable salts thereof, may also be useful to prevent MRSA and MRSE infections in a subject. For example, TarO inhibitors may be used to coat medical devices such as catheters, shunts, and prosthetic devices to prevent infections by preventing the bacteria from forming biofilms.

The present invention also includes a compound of Formula I, or a pharmaceutically acceptable salt thereof, (i) for use in, (ii) for use as a medicament for, or (iii) for use in the preparation or manufacture of a medicament for treating bacterial infection. In these uses, the compounds of the present invention can optionally be employed in combination with one or more β-lactam antibiotics.

The compounds of the present invention may be used for the manufacture of a medicament which may be useful for treating one or more of these diseases, alone or in combination with a β-lactam antibiotic, including but not limited to, a penicillin antibiotic, a cephamycin antibiotic, a cephalosporin antibiotic or a carbapenem antibiotic:

(1) bacterial infections;
(2) gram negative bacterial infections;
(3) gram positive bacterial infections;
(4) methicillin-resistant *S. aureus* (MRSA) infections; and
(4) methicillin-resistant *S. epidermidis* (MRSE) infections.

The compounds of the present invention may be used for manufacturing a medicament for the treatment of one or more of these diseases in combination with a β-lactam antibiotic, such as a penicillin antibiotic, a cephamycin antibiotic, a cephalosporin antibiotic or a carbapenem antibiotic:

(1) bacterial infections;
(2) gram negative bacterial infections;
(3) gram positive bacterial infections;
(4) methicillin-resistant *S. aureus* (MRSA) infections; and
(4) methicillin-resistant *S. epidermidis* (MRSE) infections.

Further, the compounds of the present invention may be used for manufacturing a medicament for the treatment of one or more of these diseases in combination with a β-lactam antibiotic selected from: imipenem and dicloxacillin:

(1) bacterial infections;
(2) gram negative bacterial infections;
(3) gram positive bacterial infections;
(4) methicillin-resistant *S. aureus* (MRSA) infections; and
(4) methicillin-resistant *S. epidermidis* (MRSE) infections.

A compound of formula I of the present invention, or a pharmaceutically acceptable salt thereof, may be used in the manufacture of a medicament for the treatment of bacterial infections in a human or other mammalian patient.

A compound of formula I of the present invention, or a pharmaceutically acceptable salt thereof, may be used in the manufacture of a medicament for the treatment of gram negative bacterial infections in a human or other mammalian patient.

A compound of formula I of the present invention, or a pharmaceutically acceptable salt thereof, may be used in the manufacture of a medicament for the treatment of gram positive bacterial infections in a human or other mammalian patient.

In particular, a compound of formula I of the present invention, or a pharmaceutically acceptable salt thereof, may be used in the manufacture of a medicament for the treatment of MRSA infections in a human or other mammalian patient. In particular, a compound of formula I of the present invention, or a pharmaceutically acceptable salt thereof, may be used in the manufacture of a medicament for the treatment of MRSE infections in a human or other mammalian patient.

Other medical uses of the compounds of the present invention are described herein.

The phrase "treatment of a bacterial infection" means the administration of a compound of the present invention, or a pharmaceutically acceptable salt thereof, alone or in combination with another antibiotic, such as but not limited to a β-lactam antibiotic, to a subject, such as a human or mammal, infected with bacteria. The phrase "treatment of a bacterial infection" as used herein includes but is not limited to, treatment of a gram negative bacterial infection, treatment of a gram positive bacterial infection, treatment of a MRSA infection, and treatment of a MRSE infection.

The phrase "bacterial infection" means an infection caused by bacteria.

The phrase "gram negative bacterial infection" means an infection caused by gram negative bacteria.

The phrase "gram positive bacterial infection" means an infection caused by gram positive bacteria.

The phrase "MRSA infection" means an infection caused by MRSA bacteria.

The phrase "MRSE infection" means an infection caused by MRSE bacteria.

One outcome of treatment may be killing the bacteria in the bacterial infection. Another outcome of treatment may be decreasing the number of bacteria. Another outcome of treatment may be inducing cell death in a bacterium, in particular in a gram positive bacterium. Another outcome of treatment may be reducing the proliferation of bacterium, in particular gram positive bacterium. Another outcome of treatment may be inducing cell death in a bacterium, in particular in a gram negative bacterium. Another outcome of treatment may be reducing the proliferation of bacterium, in particular gram negative bacterium. Another outcome of treatment may be decreasing bacterial levels in a subject. Another outcome of treatment may be decreasing the bacterial load. Another outcome of treatment may be increasing β-lactam antibiotic effectiveness against the bacteria. Another outcome of treatment may be decreasing bacterial resistance to β-lactam antibiotics. Another outcome of treatment may be increasing bacterial susceptibility to treatment with β-lactam antibiotics. Another outcome of treatment may be to decrease the viability of the bacteria. Another outcome of treatment may be to inhibit bacterial growth. Another outcome of treatment may be to kill >95% of the bacteria. Another outcome of treatment may be to kill >80% of the bacteria. Another outcome of treatment may be to kill >50% of the bacteria. Another outcome of treatment may be to kill >20% of the bacteria. Another outcome of treatment may be to kill >10% of the bacteria. Another outcome of treatment may be to kill enough bacteria in a subject to enable the subject's immune system to kill the bacteria. Another outcome of treatment may be to sensitize bacteria to the subject's immune system response.

Another outcome of treatment may be achieving the clinical breakpoint of β-lactam antibiotics established by CLSI (the Clinical and Laboratory Standard Institute USA), or the maximum concentration at which a specific bacterium is designated as susceptible or resistant to the antibiotic. The antibiotic clinical breakpoint definitions are determined and published yearly by the Clinical and Laboratory Standard Institute USA (CLSI). The current clinical breakpoint for imipenem is 4 µg/ml for the susceptibility/resistance profile of Staphylococci. The current clinical breakpoint for dicloxacillin is 8 µg/ml for the susceptibility/resistance profile of Staphylocci.

Another outcome of treatment may be restoring the efficacy of β-lactam antibiotics against methicillin resistant Staphylococci. Another outcome of treatment may be restoring the efficacy of imipenem against MRSA and/or MRSE. Another outcome of treatment may be restoring the efficacy of dicloxacillin against MRSA and/or MRSE. Another outcome of treatment may be a decrease in the number of symptoms of a bacterial infection. Another outcome of treatment may be the reduction in the duration, severity, or frequency of one or more symptoms of a bacterial infection.

Symptoms of a bacterial infection differ depending on the specific population of gram negative and/or gram positive bacteria present in the subject and the site (e.g. tissue in the subject) where the bacteria are located. General symptoms of a gram negative and/or a gram positive bacterial infection include but are not limited to: fever, swelling, pain, and discharge in the infected area. Additional symptoms may include sore throat, sinus infection, pharyngitis, nasal discharge, headaches, nausea, stomach pain, stomach inflammation, dehydration, peptic ulcer, stomach ulcer, indigestion, meningitis, lethargy, gatigue, stiffness in neck and back, shaking, low blood pressure, redness in the eye, watery or itchy eyes, blurred vision, abdominal cramping, vomiting, weakness, sensory loss, chills, difficulty breathing, chest pain, stuffy nose, congestion, increased heartbeat, discomfort, rash, skin discoloration, strong urge to urinate, burning sensation during urination, blood in urine, cloudy urine, strong-smelling urine, black tarry or bloody stools, diarrhea, loss of bowel control, swollen lymph nodes, confusion or disorientation, yeast infection, bacterial baginosis, sepsis, painful acne, and boils. Additional symptoms of bacterial infections are known in the art.

The term "bacterial load" means the measurable quantity of bacteria in a subject or patient. The phrase "decreasing bacterial load" includes decreasing gram negative bacterial load; decreasing gram positive bacterial load; decreasing MRSE bacterial load; and decreasing MRSA bacterial load.

The phrase "increasing β-lactam antibiotic effectiveness" means the ability of a compound of the present invention to increase or restore the ability of β-lactam antibiotics to treat bacterial infections, including but not limited to gram positive bacterial infections, MRSA infections and MRSE infections, when administered in combination with a β-lactam antibiotic.

The phrases "increase bacterial susceptibility to treatment with a β-lactam antibiotic" and "decreasing bacterial resistance to β-lactam antibiotics" mean that when the bacteria is treated with a combination of a compound of the present invention and a β-lactam antibiotic, less of the β-lactam antibiotic is required to reach 95% inhibition of the bacteria (or $MITC_{95}$) than when the β-lactam antibiotic is administered alone.

The phrase "decreasing bacterial resistance to β-lactam antibiotics" includes decreasing gram negative bacteria resistance to β-lactam antibiotics; decreasing gram positive bacteria resistance to β-lactam antibiotics; decreasing MRSE resistance to β-lactam antibiotics; and decreasing MRSA resistance to β-lactam antibiotics.

The term "antibiotic" refers to a compound or composition which decreases the viability of a microorganism or bacteria, or which inhibits the growth or proliferation of a microorganism or bacteria. The phrase "inhibits the growth or proliferation" means increasing the generation time (i.e., the time required for the bacterial cell to divide or for the population to double).

The terms "beta-lactam antibiotic"and" β-lactam antibiotic" refer to a compound with antibiotic properties that contains a beta-lactam ring in their molecular structures. β-lactam antibiotics that may be suitable for use in combination with the compounds of the present invention include, but are not limited to: penicillin antibiotics, cephamycin antibiotics, cephalosporin antibiotics, and carbapenem antibiotics.

The terms "MRSA infection" as used herein means a methicillin-resistant *Staphylococcus aureus* infection.

The terms "MRSE infection" as used herein means a methicillin-resistant *Staphylococcus epidermidis* infection.

The terms "administration of" and or "administering a" compound should be understood to mean providing a compound of the invention or a prodrug of a compound of the invention to the individual or mammal in need of treatment. Administration includes providing the compound of the invention or a prodrug of a compound of the invention to the individual or mammal in need of treatment, alone or in combination with a β-lactam.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, rectal, topical, parenteral, ocular, pulmonary, nasal, intravenous, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require inhibition of TarO activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1, 2, 3, 4, 5 or 6 times per day, preferably 1, 2, 3, or 4 times a day, more preferably once or twice per day. The compounds may be administered for 1 day to 28 days, or longer until the bacterial infection is treated or prevented.

The compounds of the present invention may be administered intravenously as shots or vaccinations. Intravenous administration of a compound of the present invention can be conducted by reconstituting a powdered form of the compounds with an acceptable solvent. Suitable solvents include, for example, saline solutions (e.g. 90% sodium chloride injection) and sterile water (e.g. Sterile Water for Injection, Bacteriostatic Water for Injection with methylparaben and propylparaben). The powdered form of the compound can be obtained by lyophilization of a solution of the compound, after which the powder can be stored (e.g. in a sealed vial) at or below room temperature until it is reconstituted. The concentration of the compound in the reconstituted IV solution can be, for example, in a range of from about 0.1 mg/mL to about 20 mg/mL.

For intravenous administration, the compositions are preferably provided in the form of an intravenous (IV) solution containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The intravenous solution may be administered on a regimen of 1, 2, 3, 4, 5 or 6 times per day, preferably 1, 2, 3, or 4 times a day, more preferably once or twice per day. The compounds may be administered for 1 day to 28 days, or longer until the bacterial infection is treated or prevented.

When treating or preventing bacterial infections, including but not limited to MRSA and MRSE, or other diseases for which compounds of the present invention are indicated, generally satisfactory results are obtained when the compounds of the present invention are administered at a daily dosage of from about 0.01 mg to about 500 mg per kilogram of animal body weight, preferably given as a single daily dose or in divided doses two to six times a day, or in sustained release form. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients.

The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Combinations

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have bacterial infections, including but not limited to antibiotic resistant gram negative bacterial infections, gram positive bacterial infections, MRSA infections and MRSE infections, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antibiotic compounds, or in combination with one or more antibiotics, such as β-lactam antibiotics, when the patient's bacterial levels are not adequately responding to treatment.

When a compound of the present invention is used contemporaneously with one or more other drugs, a pharmaceutical composition in unit dosage form containing such other drugs and the compound of the present invention is preferred. However, the combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

It is generally advantageous to use a compound of Formula I in admixture or conjunction with a beta-lactam antibiotic, such as a carbapenem antibiotic, a penicillin antibiotic, a cephalosporin antibiotic, a cephamycin antibiotic, or another β-lactam antibiotic, or a prodrug thereof. The compound of Formula I and the β-lactam antibiotic can be administered separately (at the same time or as different times) or in the form of a single composition containing both active ingredients.

Examples of beta-lactam antibiotics that may be administered, separately or in the same pharmaceutical composition, in combination with a compound of the formulas described herein include, but are not limited to:

(1) penicillin antibiotics, including but not limited to, methicillin, oxacillin, penicillin G, dicloxacillin and naficillin;
(2) cephamycin antibiotics, including but not limited to, cefepime and cefoxitin;
(3) cephalosporin antibiotics, including but not limited to, cefuroxime, ceftiofur and cefquinome; and
(4) carbapenem antibiotics, including but not limited to, imipenem, doripenem, meropenem, and tebipenem.

Other suitable beta-lactam antibiotics that may be administered in combination with a compound of the present invention, and either administered separately or in the same pharmaceutical composition are summarized below.

Carbapenem antibiotics suitable for co-administration with compounds of the present invention include imipenem, meropenem, doripenem, tebipenem, biapenem, (4R,5S, 6S)-3-[3S, 5S)-5-(3-carboxyphenyl-carbamoyl)pyrrolidin-3-yl-thio]-6-(1R)-1-hydroxyethyl]-4-methyl-7-oxo-1-azabicyclo [3.2.0]hept-2-ene-2-carboxylic acid, (1S,5R, 6S)-2-(4-(2-(((carbamoylmethyl)-1,4-diazoniabicyclo[2.2.2]oct-1-yl)-ethyl(1,8-naphthosultam)methyl)-6-[1(R)-hydroxyethyl]-1-methylcarbapen-2-em-3-carboxylate chloride, BMS181139 ([4R-[4alpha,5beta,6beta(R*)]]-4-[2-[(aminoiminomethyl) amino]ethyl]-3-[(2-cyanoethyl)thio]-6-(1-hydroxyethyl)-7-oxo-1-azabicyclo[3.2.0]hept-2-ene-2-carboxylic acid), B0-2727 ([4R-3[3S*,5S*(R*)], 4alpha,5beta,6beta(R*)]]-6-(1-hydroxyethyl)-3-[[5-[1-hydroxy-3-(methylamino)propyl]-3-pyrrolidinyl]thio]-4-methyl-7-oxo-1-azabicyclo[3.2.0] hept-2-ene-2-carboxylic acid monohydrochloride), E1010 ((1R,5S, 6S)-6-[1(R)-hydroxymethyl]-2-[2(S)-[1(R)-hydroxy-1-[pyrrolidin-3(R)-yl]methyl]pyrrolidin-4(S)-ylsulfanyl]-1-methyl-1-carba-2-penem-3-carboxylic acid hydrochloride) and S4661 ((1R,5S,6S)-2-[(3S,5S)-5-(sulfamoylaminomethyl) pyrrolidin-3-yl]thio-6-[(1R)-1-hydroxyethyl]-1-methylcarbapen-2-em-3-carboxylic acid), (1S,5R, 6S)-1-methyl-2-{7-[4-(aminocarbonylmethyl)-1,4-diazoniabicyclo(2.2.2)octan-1yl]-methyl-fluoren-9-on-3-yl}-6-(1R-hydroxyethyl)-carbapen-2-em-3 carboxylate chloride.

Penicillin antibiotics suitable for co-administration with compounds of the present invention include dicloxacillin, methicillin, oxacillin, penicillin G, naficillin, benzylpenicillin, phenoxymethylpenicillin, carbenicillin, azidocillin, propicillin, ampicillin, amoxicillin, epicillin, ticarcillin, cyclacillin, pirbenicillin, azlocillin, mezlocillin, sulbenicillin, piperacillin, and other known penicillins. The penicillins may be used in the form of pro-drugs thereof, for example as in vivo hydrolysable esters, for example the acetoxymethyl, pivaloyloxymethyl, α-ethoxycarbonyloxy-ethyl and phthalidyl esters of ampicillin, benzylpenicillin and amoxicillin; as aldehyde or ketone adducts of penicillins containing a 6-α-aminoacetamido side chain (for example hetacillin, metampicillin and analogous derivatives of amoxicillin); and as esters of carbenicillin and ticarcillin, for example the phenyl and indanyl α-esters.

Cephalosporin antibiotics suitable for co-administration with compound of the present invention include cefuroxime, cefatrizine, cephaloridine, cephalothin, cefazolin, cephalexin, cephacetrile, cephapirin, cephamandole nafate, cephradine, 4-hydroxycephalexin, cephaloglycin, cefoperazone, cefsulodin, ceftazidime, cefmetazole, cefotaxime, ceftriaxone, ceftiofur and cefquinome; and other known cephalosporins, all of which may be used in the form of pro-drugs thereof.

Cephamycin antibiotics suitable for co-administration with compound of the present invention include cefepime, cefoxitin, cefotetan and cefmetazole, all of which may be used in the form of pro-drugs thereof.

In one embodiment, the antibiotic co-administered with a compound of the present invention is selected from: imipenem and dicloxacillin.

In another embodiment, the antibiotic co-administered with a compound of the present invention is a carbapenem antibiotic selected from: imipenem, meropenem, doripenem and tebipenem.

In another embodiment, the antibiotic co-administered with a compound of the present invention is a penicillin antibiotic selected from: methicillin, oxacillin, penicillin G, dicloxacillin, naficillin, ampicillin, amoxicillin, carbenicillin, piperacillin, azlocillin, mezlocillin, and ticarcillin, or pharmaceutically acceptable salts thereof. In another embodiment, the antibiotic co-administered with a compound of the present invention is a penicillin antibiotic selected from: methicillin, oxacillin, penicillin G, dicloxacillin, and naficillin, or pharmaceutically acceptable salts thereof. Such penicillins can optionally be used in the form of their pharmaceutically acceptable salts, for example their sodium salts. Ampicillin or amoxicillin can alternatively be employed in the form of fine particles of the zwitterionic form (generally as ampicillin trihydrate or amoxicillin trihydrate) for use in an injectable or infusable suspension. In an aspect of this embodiment, the penicillin co-administered with a compound of the present invention is amoxicillin, optionally in the form of its sodium salt or the trihydrate.

In another embodiment, the antibiotic co-administered with a compound of the present invention is a cephalosporin antibiotic selected from: cefuroxime, cefotaxime, ceftriaxone and ceftazidime, or a pharmaceutically acceptable salts thereof. In another embodiment, the antibiotic co-administered with a compound of the present invention is the cephalosporin antibiotic cefuroxime, or a pharmaceutically acceptable salt thereof.

In another embodiment, the antibiotic co-administered with a compound of the present invention is a cephamycin antibiotic selected from: cefepime, cefoxitin, cefotetan and cefmetazole, all of which may be used in the form of pro-drugs thereof. In another embodiment, the antibiotic co-administered with a compound of the present invention is a cephamycin antibiotic selected from: cefepime and cefoxitin, all of which may be used in the form of pro-drugs thereof.

The compounds of the present invention, or pharmaceutically acceptable salts thereof, in combination with a β-lactam antibiotic, including but not limited to imipenem and dicloxacillin, may provide bactericidal synergy in treating bacterial infections in a subject. When co-administered with a β-lactam antibiotic, the combination of the compound of the invention and the β-lactam antibiotic can provide a synergistic bactericical effect.

The terms "synergistic bactericidal effect" and "bactericidal synergy" indicate that the bactericidal effect produced when a β-lactam antibiotic is administered in combination with a compound of the present invention is greater than the bactericidal effect produced when the (3-lactam antibiotic is administered alone, or when a compound of the present invention is administered alone. The "synergistic bactericidal effect" and "bactericidal synergy" may represent a significant reduction in minimum inhibition concentration (MIC) values for a beta-lactam as a single agent. As a result, less β-lactam antibiotic is required to reach 95% inhibition (MITC$_{95}$) of the bacteria when used in combination with a compound of the present invention.

The term bactericidal effect includes but is not limited to bacteria death or the amount of bacteria killed.

The compositions and combinations of the present invention are suitably administered in therapeutically effective amounts. The term "therapeutically effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated (e.g., bacterial infection and/or bacterial drug resistance). In another embodiment, the effective amount is a "prophylactically effective amount" for prophylaxis of the symptoms of the disease or condition being prevented (e.g., bacterial infection and/or bacterial drug resistance. The term "therapeutically effective amount" also includes herein the amount of active compound sufficient to decrease the bacterial level in a subject and thereby elicit the response being sought (i.e., an "inhibition effective amount"). When the active compound (i.e., active ingredient) is administered as the salt, references to the amount of active ingredient are to the free acid or free base form of the compound.

The term "drug resistance" refers to the loss of susceptibility of a drug target, such as bacteria, to drug treatment. The term "resistance" refers to the decrease or loss of inhibitory effect of the drug on the target bacteria.

The present invention also includes a method for inhibiting bacterial growth comprising administering to a bacterial cell culture, or to a bacterially infected cell culture, tissue, or organism, an inhibition effective amount of a compound of Formula I, or a pharmaceutically acceptable salt thereof, alone or in combination with a β-lactam antibiotic. The method can involve administration of a compound of Formula I, or a pharmaceutically acceptable salt thereof, alone or in combination with a β-lactam antibiotic, to an experimental cell culture in vitro to prevent the growth of β-lactam resistant bacteria. The method can alternatively involve administration of a compound of Formula I, or a pharmaceutically acceptable salt thereof, alone or in combination with a β-lactam antibiotic, to a subject including a patient, human or mammal, to prevent or inhibit the growth of β-lactam resistant bacteria in vivo, or to kill β-lactam resistant bacteria in vivo. In these cases the compound of Formula I is typically co-administered with a β-lactam antibiotic.

Compounds of the invention, or a pharmaceutically acceptable salt thereof, alone or in combination with a β-lactam antibiotic, may be employed for the treatment, prevention, prophylaxis or inhibition of bacterial growth or infections due to bacteria that are resistant to β-lactam antibiotics.

More particularly, the bacteria may be β-lactamase positive strains that are highly resistant to β-lactam antibiotics. The terms "slightly resistant" and "highly resistant" are well-understood by those of ordinary skill in the art (see, e.g., Payne et al., Antimicrobial Agents and Chemotherapy 38:767-772 (1994); Hanaki et al., Antimicrobial Agents and Chemotherapy 30:11.20-11.26 (1995)).

Compounds of the invention may be useful in combination with antibiotic agents for the treatment of infections caused by Class C-β-lactamase producing strains, in addition to those infections which are subsumed within the antibacterial spectrum of the antibiotic agent.

Examples of class C-β-lactamase producing bacteria are *Pseudomonas aeruginosa, Enterobacter cloacae, Klebsiella pneumoniae, Escherichia coli* and *Acinetobacter baumannii.*

The present invention also provides a method for the treatment or prevention of a TarO mediated disease, which method comprises administration to a patient in need of such treatment or at risk of developing a TarO mediated disease of an amount of a compound of formula I, or a pharmaceutically acceptable salt thereof, and an amount of one or more active ingredients, such that together they give effective relief.

In a further aspect of the present invention, there is provided a pharmaceutical composition comprising a compound of formula I, or a pharmaceutically acceptable salt thereof, and one or more active ingredients, together with at least one pharmaceutically acceptable carrier or excipient.

Thus, according to a further aspect of the present invention there is provided the use of a compound of formula I, or a pharmaceutically acceptable salt thereof, and one or more active ingredients for the manufacture of a medicament for the treatment or prevention of a TarO mediated disease. In a further or alternative aspect of the present invention, there is therefore provided a product comprising a compound of formula I, or a pharmaceutically acceptable salt thereof, and one or more active ingredients as a combined preparation for simultaneous, separate or sequential use in the treatment or prevention of a TarO mediated disease. Such a combined preparation may be, for example, in the form of a twin pack.

It will be appreciated that for the treatment or prevention of bacterial infections, gram negative bacterial infections, gram positive bacterial infections, MRSA infections, MRSE infections, and related bacterial infections, a compound of formula I, or a pharmaceutically acceptable salt thereof, may be used in conjunction with another pharmaceutical agent effective to treat the bacterial infection.

The present invention also provides a method for the treatment or prevention of bacterial infections, gram negative bacterial infections, gram positive bacterial infections, MRSA infections, MRSE infections, and related bacterial infections, which method comprises administration to a patient in need of such treatment an amount of compound of formula I, or a pharmaceutically acceptable salt thereof, and an amount of another pharmaceutical agent effective to treat that bacterial infection, such that together they give effective relief.

The present invention also provides a method for the treatment or prevention of bacterial infections, gram negative bacterial infections, gram positive bacterial infections, MRSA infections, MRSE infections, and related bacterial infections, which method comprises administration to a patient in need of such treatment an amount of a compound of formula I, or a pharmaceutically acceptable salt thereof, and an amount of a β-lactam antibiotic useful in treating that particular bacterial infection, such that together they give effective relief.

The compounds of formula I, or a pharmaceutically acceptable salt thereof, may be useful in combination with β-lactam antibiotics, such as, but not limited to, imipenem and dicloxacillin, for the treatment of bacterial infections, particularly antibiotic resistant gram negative bacterial infections and/or gram positive bacterial infections such as methicillin-resistant Staphylocuccus *aureus* (MRSA) infections.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. In one embodiment, the therapeutically effective amount as used herein means that amount of the compound of the present invention that alleviates the symptoms of the bacterial infection or bacterial drug resistance when administered alone or in combination with a beta-lactam antibiotic.

The novel methods of treatment and prevention of this invention are for disorders known to those skilled in the art. The term "patient" as used herein means a human or mammal. The term "subject" as used herein means a human, mammal or cell. The term "mammal" includes humans, companion animals such as dogs and cats, and livestock such as cattle, swine and poultry. The term cell includes cells in a cell culture.

The weight ratio of the compound of the Formula I to the second active ingredient may be varied and will depend upon the effective dose of each ingredient. Generally, an effective dose of each will be used. Thus, for example, when a compound of the Formula I is combined with a beta-lactam antibiotic the weight ratio of the compound of the Formula I to the beta-lactam antibiotic will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

Abbreviations

Ac is acetyl; AcCN is acetonitrile; AcO is acetoxy; Alk is alkyl; Al(OiPr)$_3$ is aluminum triisopropoxide; APCI is atmospheric pressure chemical ionization; aq or aq. is aqueous; Ar is aryl; Boc is tert-butoxycarbonyl; Br is broad; t-BuOK is potassium tert-butoxide; ° C. is degrees celsius; Cbz is benzyloxycarbonyl; CH$_2$Cl$_2$ is dichloromethane; CO is carbon monoxide; conc or conc. is concentrated; d is doublet; DAST is (diethylamino)sulfur trifluoride; DBU is 1,8-diazabicyclo[5.4.0]undec-7-ene; DIAD is diisopropyl azodicarboxylate; DCM is dichloromethane; DIEA and DIPEA are N,N-diisopropylethylamine; DMAP is 4-dimethylaminopyridine; DMF is N,N-dimethylformamide; DMSO is dimethylsulfoxide; dppf is 1,1'-Bis(diphenyl-phosphino)ferrocene; EDC and EDCl are 1-ethyl-3-(3-dimethylaminopropyl)carbodiimide; ESI is electrospray ionization; EA or EtOAc is ethyl acetate; Et is ethyl; EtMgBr is ethyl magnesium bromide; EtOH is ethanol; g is gram(s); h or hr or hrs is hour(s); HPLC is high pressure liquid chromatography; HOAc or AcOH is acetic acid; iPrMgCl is isopropyl magnesium chloride; IPA and iPrOH are isopropanol; kg is kilogram(s); KOH ispotassium hydroxide; KOAc is potassium acetate; L is liter; LC-MS is liquid chromatography-mass spectroscopy; LDA is lithium diisopropyl amide; LiGH is lithium hydroxide; m is multiplet; m-CPBA, MCPBA, or mCPBA is meta chloroperbenzoic acid; mL or ml is milliliter; min or mins is minute(s); mol is mole(s); mmol is mmole(s); mg is milligram(s); MeI is methyl iodide; MeCN is acetonitrile; MeMgBr is methyl magnesium bromide; MeOH is methyl alcohol; MgSO$_4$ is magnesium sulfate; MS is mass spectroscopy; MsCl or Ms-Cl is methane sulfonyl chloride; N is normal; Na(AcO)$_3$BH is sodium triacetoxy borohydride; NaHMDS is sodium hexamethyldisilazide; NaOH is sodium hydroxide; Na$_2$SO$_4$ is sodium sulfate; NH$_4$OAc is ammonium acetate; NBS is N-bromo succinamide; NIS is N-iodo succinamide; HNMe(OMe)HCl is N-methoxy-N-methylamine hydrochloride salt; NMM is N-methyl morpholine; NMO is 4-methyl morpholine N-oxide; NMP is 1-methyl-2-pyrrolidinone; NMR is nuclear magnetic resonance spectroscopy; PE is petroleum ether; PG is protecting group; P(Cy)$_3$ is tricyclohexyl phosphine; Pd(Ph$_3$)$_4$ is tetrakis(triphenylphosphine)-palladium(O); Pd$_2$(dba)$_3$ is tris(dibenzylideneacetone)-dipalladium(0); Pd[P(t-Bu)$_3$]$_2$ is bis(tri-tert-butylphosphine)palladium (0); Pd(dppf)Cl$_2$ is [1,1'-bis(diphenylphosphino)ferrocene]-dichloropalladium (II); PMB is para-methoxybenzyl; PMBCl ispara-methoxybenzyl chloride; prep is preparative; prep. TLC or prep-TLC, or prep TLC is preparative thin layer chromatography; RBF is round bottom flask; RCM is ring closing metathesis reaction; rt or r.t. or RT is room temperature; s is singlet; SFC is supercritical fluid chromatography; s-phos is 2-dicyclohexylphosphino-2',6'-dimethoxybiphenyl; t is triplet; TBDMSCl is tert-butyldimethyl silyl chloride; TBTU is N,N,N',N'-Tetramethyl-O-(benzotriazol-1-yl)uronium tetrafluoroborate; TEA is triethyl amine; THF is tetrahydrofuran; Ti(OiPr)$_4$ is titanium isopropoxide; TFA is trifluoroacetic acid; TLC is thin-layer chromatography; TMSCl is trimethyl silyl chloride; TsCl or TosCl isp-toluene sulfonyl chloride; TsOH is p-toluenesulfonic acid, and xphos is 2-Dicyclohexylphosphino-2',4',6'-triisopropylbiphenyl.

Several methods for preparing the compounds of this invention are illustrated in the following Schemes and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following examples are provided for the purpose of illustration only and are not to be construed as limitations on the disclosed invention. All temperatures are degrees Celsius unless otherwise noted.

Example 1

(4S,5R)-5-(3,5-bis(trifluoromethyl)phenyl)-N-(isoquinolin-4-ylmethyl)-4-methyl-2-oxooxazolidine-3-carboxamide

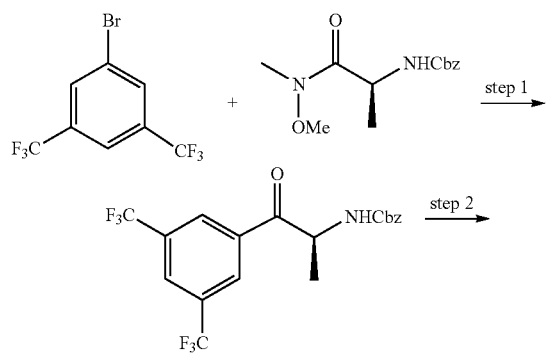

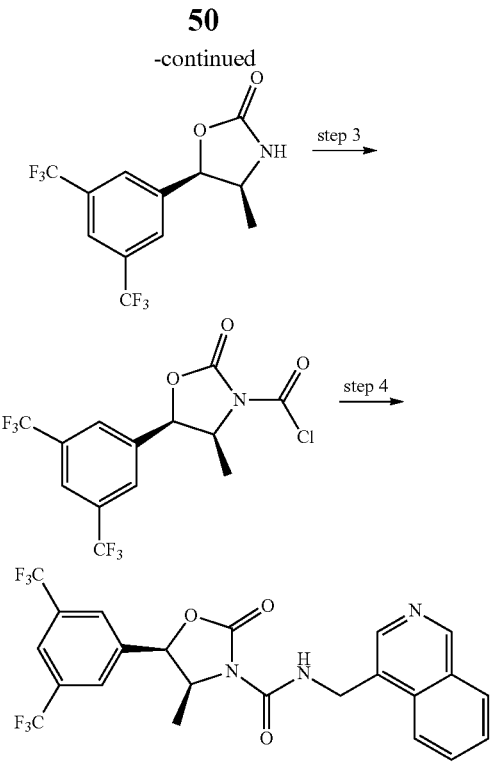

Example 1

Step 1: Benzyl (S)-(1-(3,5-bis(trifluoromethyl)phenyl)-1-oxopropan-2-yl)carbamate To a solution of 1-bromo-3,5-bis(trifluoromethyl)benzene (10.0 g, 34 mmol, 1 eq) and benzyl (S)-(1 (methoxy(methyl)amino)-1-oxopropan-2-yl)carbamate (10.8 g, 40 mmol, 1.2 eq) in THF (100 mL) at −10° C. was added dropwise i-PrMgCl (85 mL, 1 M in THF, 85 mmol, 2.5 eq). After the addition, the reaction mixture was stirred at rt for 12 h. Then the reaction mixture was added slowly into a solution of 1 N HCl (190 mL) at 0° C. The resulting solution was extracted with EtOAc (150 mL×3), and the combined EtOAc extracts were dried, and evaporated to give the title compound, which was used in the next step without further purification.

Step 2: (4S,5R)-5-(3,5-bis(trifluoromethyl)phenyl)-4-methyloxazolidin-2-one To a mixture of benzyl (S)-(1-(3,5-bis(trifluoromethyl)phenyl)-1-oxopropan-2-yl)carbamate (16.0 g, 38 mmol, 1 eq) and i-PrOH (22.0 g, 418 mmol, 11 eq) in toluene (60 mL) was added Al(OiPr)$_3$ (6.2 g, 34 mmol). After the addition, the reaction mixture was stirred at 40-50° C. for 12 h. The reaction mixture was cooled to rt, then 50% KOH (3.9 g in 3.9 g of H$_2$O) was added. The resulting mixture was stirred at 20° C. for 3 h and then quenched with brine (100 mL) and extracted with EtOAc (100 mL×2). The combined organic layers were washed with brine (100 mL×4) and dried. The crude product was purified by flash chromatography (0% to 100% EtOAc in hexane) to provide the title compound.

Step 3: (4S,5R)-5-(3,5-bis(trifluoromethyl)phenyl)-4-methyl-2-oxooxazolidine-3-carbonyl chloride To a solution of (4S,5R)-5-(3,5-bis(trifluoromethyl)phenyl)-4-methyloxazolidin-2-one (8.0 g, 26.1 mmol) in THF (50 mL) was added n-butyllithium (10.4 mL, 2.5 M in hexane, 26.1 mmol) slowly at −78° C. The resulting mixture was stirred at −78° C. for 20 min. Then trichloromethyl carbonochloridate (3.2 mL, 26.1 mmol) was added rapidly. The reaction mixture was stirred for 30 min, and then allowed to warm to rt. The reaction mixture was evaporated to obtain the title compound, which was used in next step without further purification.

Step 4: (4S,5R)-5-(3,5-bis(trifluoromethyl)phenyl)-N-(isoquinolin-4-ylmethyl)-4-methyl-2-oxooxazolidine-3-carboxamide To a solution of (4S,5R)-5-(3,5-bis(trifluoromethyl)phenyl)-4-methyl-2-oxooxazolidine-3-carbonyl chloride (64.0 mg, 0.17 mmol) in DCM (1 mL) was added a solution of isoquinolin-4-yl methanamine (93.0 mg, 0.34 mmol) and triethylamine (0.19 mL, 1.38 mmol) in DCM (1 mL). The resulting mixture was stirred at rt for 12 h, then quenched with water, extracted with DCM, and dried. The resulting residue was purified by flash chromatography (500 to 5000 EtOAc in hexane) to obtain the title compound. LC-MS m/z [M+H]$^+$ 498.47 (calc'd 498.39).

TABLE 1

The compounds in Examples 2-49 were prepared according to the procedure of Example 1.

| Example Number | Structure | Name | Calc'd Mass M + H$^+$ | Observed Mass M + H$^+$ |
|---|---|---|---|---|
| 2 | 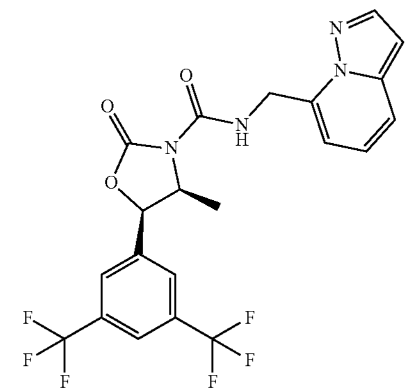 [SMILES: C[C@H]1[C@@H](c2cc(C(F)(F)F)cc(C(F)(F)F)c2)OC(=O)N1C(=O)NCc1cccc2ccnn12] | (4S,5R)-5-[3,5-bis(trifluoromethyl)phenyl]-4-methyl-2-oxo-N-(pyrazolo[1,5-a]pyridin-7-ylmethyl)-1,3-oxazolidine-3-carboxamide | 487.11 | 487.10 |
| 3 | 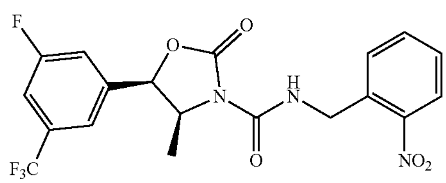 [SMILES: C[C@H]1[C@@H](c2cc(F)cc(C(F)(F)F)c2)OC(=O)N1C(=O)NCc1ccccc1[N+](=O)[O-]] | (4S,5R)-5-[3-fluoro-5-(trifluoromethyl)phenyl]-4-methyl-N-(2-nitrobenzyl)-2-oxo-1,3-oxazolidine-3-carboxamide | 442.10 | 442.16 |
| 4 | 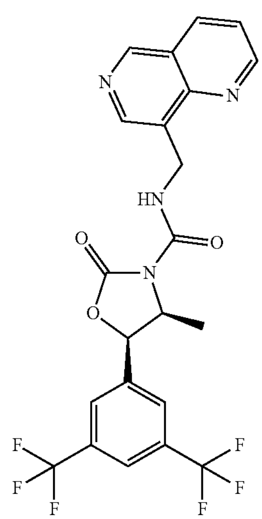 [SMILES: C[C@H]1[C@@H](c2cc(C(F)(F)F)cc(C(F)(F)F)c2)OC(=O)N1C(=O)NCc1cncc2cccnc12] | (4S,5R)-5-[3,5-bis(trifluoromethyl)phenyl]-4-methyl-N-(1,6-naphthyridin-8-ylmethyl)-2-oxo-1,3-oxazolidine-3-carboxamide | 499.38 | 499.68 |

TABLE 1-continued

The compounds in Examples 2-49 were prepared according to the procedure of Example 1.

| Example Number | Structure | Name | Calc'd Mass M + H⁺ | Observed Mass M + H⁺ |
|---|---|---|---|---|
| 5 | 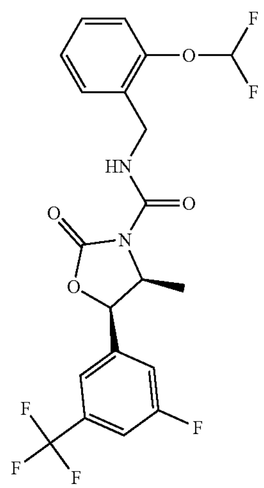 [SMILES: C[C@H]1[C@@H](c2cc(F)cc(C(F)(F)F)c2)OC(=O)N1C(=O)NCc1ccccc1OC(F)F] | (4S,5R)-N-[2-(difluoromethoxy)benzyl]-5-[3-fluoro-5-(trifluoromethyl)phenyl]-4-methyl-2-oxo-1,3-oxazolidine-3-carboxamide | 463.11 | 463.08 |
| 6 | 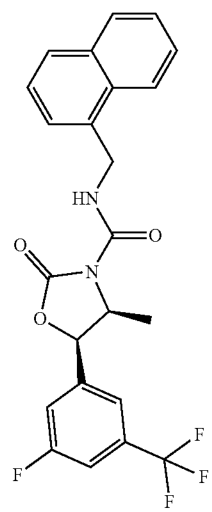 [SMILES: C[C@H]1[C@@H](c2cc(F)cc(C(F)(F)F)c2)OC(=O)N1C(=O)NCc1cccc2ccccc12] | (4S,5R)-5-[3-fluoro-5-(trifluoromethyl)phenyl]-4-methyl-N-(naphthalen-1-ylmethyl)-2-oxo-1,3-oxazolidine-3-carboxamide | 447.39 | 447.09 |
| 7 | 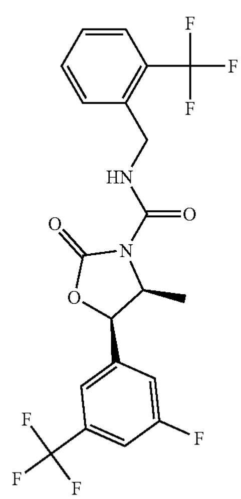 [SMILES: C[C@H]1[C@@H](c2cc(F)cc(C(F)(F)F)c2)OC(=O)N1C(=O)NCc1ccccc1C(F)(F)F] | (4S,5R)-5-[3-fluoro-5-(trifluoromethyl)phenyl]-4-methyl-2-oxo-N-[2-(trifluoromethyl)benzyl]-1,3-oxazolidine-3-carboxamide | 465.10 | 465.15 |

TABLE 1-continued

The compounds in Examples 2-49 were prepared according to the procedure of Example 1.

| Example Number | Structure | Name | Calc'd Mass M + H⁺ | Observed Mass M + H⁺ |
|---|---|---|---|---|
| 8 | 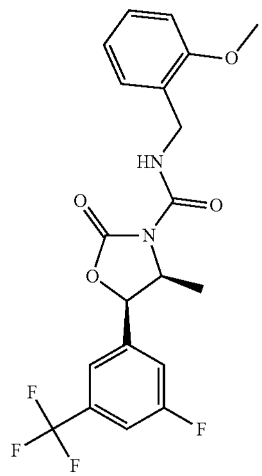 [SMILES: COc1ccccc1CNC(=O)N1C(=O)O[C@H](c2cc(F)cc(C(F)(F)F)c2)[C@@H]1C] | (4S,5R)-5-[3-fluoro-5-(trifluoromethyl)phenyl]-N-(2-methoxybenzyl)-4-methyl-2-oxo-1,3-oxazolidine-3-carboxamide | 427.13 | 427.22 |
| 9 | 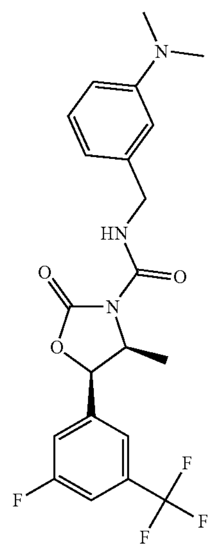 [SMILES: C[C@H]1[C@@H](c2cc(F)cc(C(F)(F)F)c2)OC(=O)N1C(=O)NCc1cccc(N(C)C)c1] | (4S,5R)-N-[3-(dimethylamino)benzyl]-5-[3-fluoro-5-(trifluoromethyl)phenyl]-4-methyl-2-oxo-1,3-oxazolidine-3-carboxamide | 440.16 | 440.25 |
| 10 | 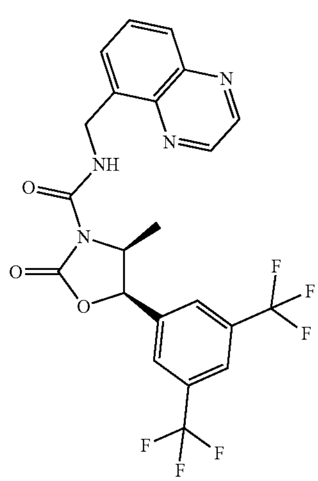 [SMILES: C[C@H]1[C@@H](c2cc(C(F)(F)F)cc(C(F)(F)F)c2)OC(=O)N1C(=O)NCc1cccc2nccnc12] | (4S,5R)-5-[3,5-bis(trifluoromethyl)phenyl]-4-methyl-2-oxo-N-(quinoxalin-5-ylmethyl)-1,3-oxazolidine-3-carboxamide | 499.12 | 499.00 |

TABLE 1-continued

The compounds in Examples 2-49 were prepared according to the procedure of Example 1.

| Example Number | Structure | Name | Calc'd Mass M + H⁺ | Observed Mass M + H⁺ |
|---|---|---|---|---|
| 11 | 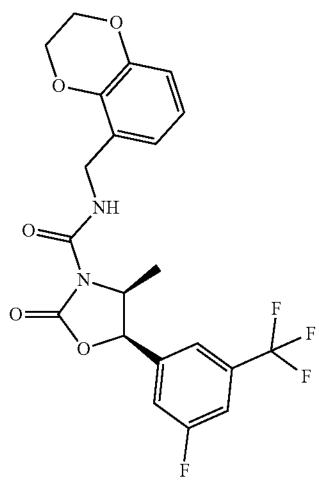 [SMILES: C[C@H]1[C@@H](c2cc(F)cc(C(F)(F)F)c2)OC(=O)N1C(=O)NCc1cccc2c1OCCO2] | (4S,5R)-N-(2,3-dihydro-1,4-benzodioxin-5-ylmethyl)-5-[3-fluoro-5-(trifluoromethyl)phenyl]-4-methyl-2-oxo-1,3-oxazolidine-3-carboxamide | 455.12 | 454.90 |
| 12 | 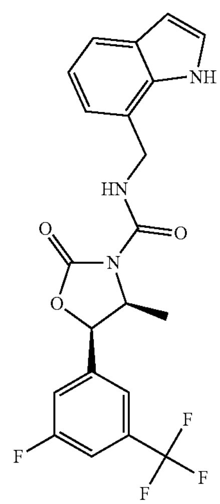 [SMILES: C[C@H]1[C@@H](c2cc(F)cc(C(F)(F)F)c2)OC(=O)N1C(=O)NCc1cccc2cc[nH]c12] | (4S,5R)-5-[3-fluoro-5-(trifluoromethyl)phenyl]-N-(1H-indol-7-ylmethyl)-4-methyl-2-oxo-1,3-oxazolidine-3-carboxamide | 436.13 | 436.16 |
| 13 | 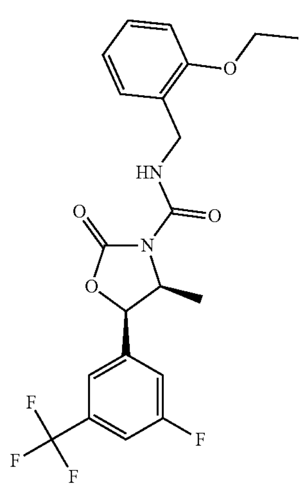 [SMILES: CCOc1ccccc1CNC(=O)N1C(=O)O[C@H](c2cc(F)cc(C(F)(F)F)c2)[C@@H]1C] | (4S,5R)-N-(2-ethoxybenzyl)-5-[3-fluoro-5-(trifluoromethyl)phenyl]-4-methyl-2-oxo-1,3-oxazolidine-3-carboxamide | 441.14 | 441.04 |

TABLE 1-continued

The compounds in Examples 2-49 were prepared according to the procedure of Example 1.

| Example Number | Structure | Name | Calc'd Mass M + H$^+$ | Observed Mass M + H$^+$ |
|---|---|---|---|---|
| 14 | 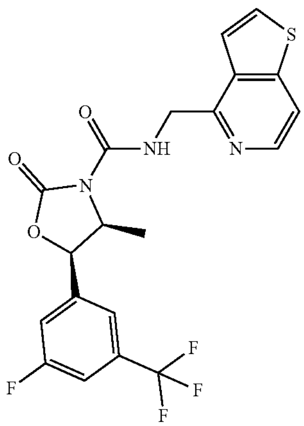 [SMILES: C[C@H]1[C@@H](c2cc(F)cc(C(F)(F)F)c2)OC(=O)N1C(=O)NCc1nccc2sccc12] | (4S,5R)-5-[3-fluoro-5-(trifluoromethyl)phenyl]-4-methyl-2-oxo-N-(thieno[3,2-c]pyridin-4-ylmethyl)-1,3-oxazolidine-3-carboxamide | 454.08 | 454.00 |
| 15 | 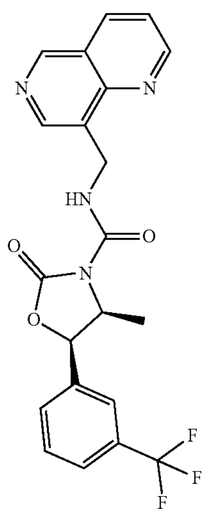 [SMILES: C[C@H]1[C@@H](c2cccc(C(F)(F)F)c2)OC(=O)N1C(=O)NCc1cncc2cccnc12] | (4S,5R)-4-methyl-N-(1,6-naphthyridin-8-ylmethyl)-2-oxo-5-[3-(trifluoromethyl)phenyl]-1,3-oxazolidine-3-carboxamide | 431.38 | 431.54 |
| 16 | 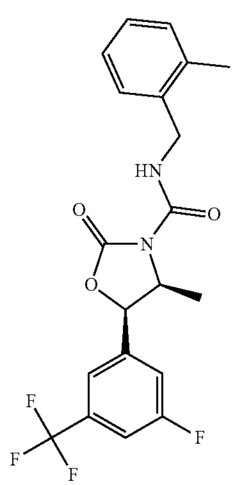 [SMILES: Cc1ccccc1CNC(=O)N1C(=O)O[C@H](c2cc(F)cc(C(F)(F)F)c2)[C@@H]1C] | (4S,5R)-5-[3-fluoro-5-(trifluoromethyl)phenyl]-4-methyl-N-(2-methylbenzyl)-2-oxo-1,3-oxazolidine-3-carboxamide | 411.13 | 411.23 |

TABLE 1-continued

The compounds in Examples 2-49 were prepared according to the procedure of Example 1.

| Example Number | Structure | Name | Calc'd Mass M + H⁺ | Observed Mass M + H⁺ |
|---|---|---|---|---|
| 17 | 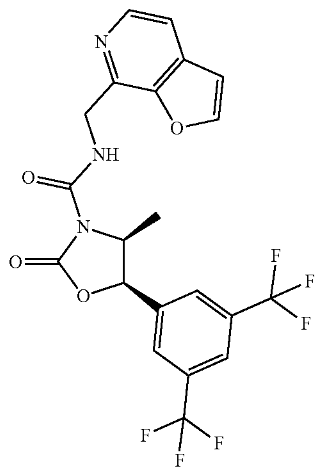 [SMILES: C[C@H]1[C@@H](c2cc(C(F)(F)F)cc(C(F)(F)F)c2)OC(=O)N1C(=O)NCc1nccc2ccoc12] | (4S,5R)-5-[3,5-bis(trifluoromethyl)phenyl]-N-(furo[2,3-c]pyridin-7-ylmethyl)-4-methyl-2-oxo-1,3-oxazolidine-3-carboxamide | 488.10 | 488.10 |
| 18 | 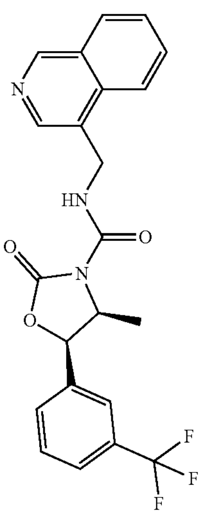 [SMILES: C[C@H]1[C@@H](c2cccc(C(F)(F)F)c2)OC(=O)N1C(=O)NCc1cncc2ccccc12] | (4S,5R)-N-(isoquinolin-4-ylmethyl)-4-methyl-2-oxo-5-[3-(trifluoromethyl)phenyl]-1,3-oxazolidine-3-carboxamide | 430.39 | 430.27 |
| 19 | 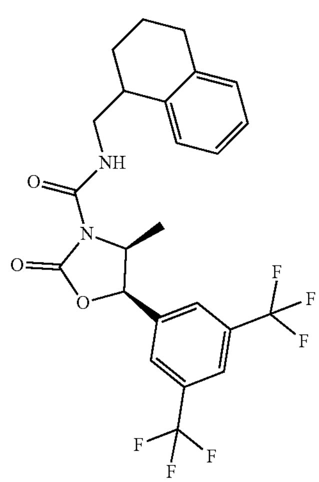 [SMILES: C[C@H]1[C@@H](c2cc(C(F)(F)F)cc(C(F)(F)F)c2)OC(=O)N1C(=O)NCC1CCCc2ccccc21] | (4S,5R)-5-[3,5-bis(trifluoromethyl)phenyl]-4-methyl-2-oxo-N-(1,2,3,4-tetrahydronaphthalen-1-ylmethyl)-1,3-oxazolidine-3-carboxamide | 501.16 | 501.10 |

TABLE 1-continued

The compounds in Examples 2-49 were prepared according to the procedure of Example 1.

| Example Number | Structure | Name | Calc'd Mass M + H⁺ | Observed Mass M + H⁺ |
|---|---|---|---|---|
| 20 | 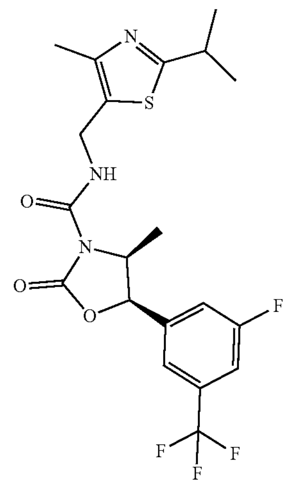 [SMILES: Cc1nc(C(C)C)sc1CNC(=O)N1C(=O)O[C@H](c2cc(F)cc(C(F)(F)F)c2)[C@@H]1C] | (4S,5R)-5-[3-fluoro-5-(trifluoromethyl)phenyl]-4-methyl-N-{[4-methyl-2-(1-methylethyl)-1,3-thiazol-5-yl]methyl}-2-oxo-1,3-oxazolidine-3-carboxamide | 460.12 | 460.20 |
| 21 | 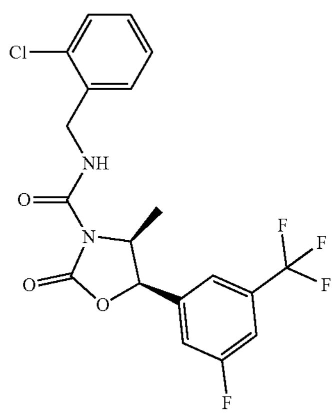 [SMILES: C[C@H]1[C@@H](c2cc(F)cc(C(F)(F)F)c2)OC(=O)N1C(=O)NCc1ccccc1Cl] | (4S,5R)-N-(2-chlorobenzyl)-5-[3-fluoro-5-(trifluoromethyl)phenyl]-4-methyl-2-oxo-1,3-oxazolidine-3-carboxamide | 431.07 | 431.00 |
| 22 | 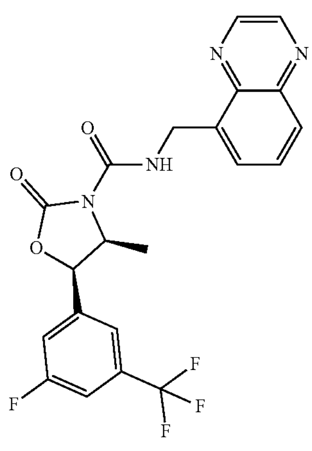 [SMILES: C[C@H]1[C@@H](c2cc(F)cc(C(F)(F)F)c2)OC(=O)N1C(=O)NCc1cccc2nccnc12] | (4S,5R)-5-[3-fluoro-5-(trifluoromethyl)phenyl]-4-methyl-2-oxo-N-(quinoxalin-5-ylmethyl)-1,3-oxazolidine-3-carboxamide | 449.12 | 449.10 |

TABLE 1-continued

The compounds in Examples 2-49 were prepared according to the procedure of Example 1.

| Example Number | Structure | Name | Calc'd Mass M + H+ | Observed Mass M + H+ |
|---|---|---|---|---|
| 23 | 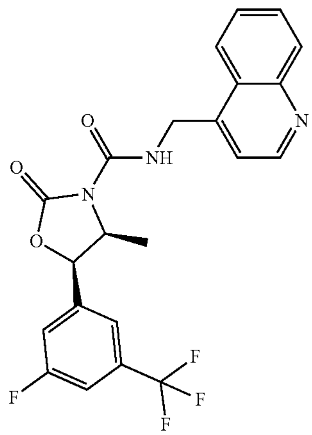 [SMILES: C[C@H]1[C@@H](c2cc(F)cc(C(F)(F)F)c2)OC(=O)N1C(=O)NCc1ccnc2ccccc12] | (4S,5R)-5-[3-fluoro-5-(trifluoromethyl)phenyl]-4-methyl-2-oxo-N-(quinolin-4-ylmethyl)-1,3-oxazolidine-3-carboxamide | 448.12 | 448.10 |
| 24 | 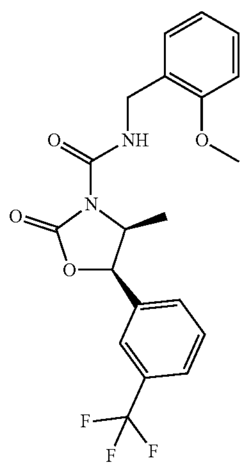 [SMILES: COc1ccccc1CNC(=O)N1C(=O)O[C@H](c2cccc(C(F)(F)F)c2)[C@@H]1C] | (4S,5R)-N-(2-methoxybenzyl)-4-methyl-2-oxo-5-[3-(trifluoromethyl)phenyl]-1,3-oxazolidine-3-carboxamide | 409.14 | 409.25 |
| 25 | 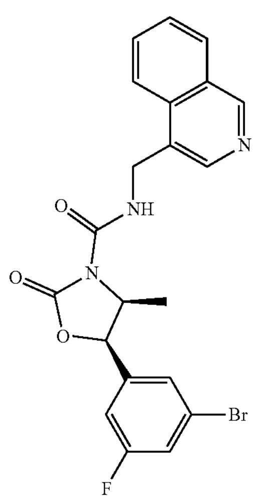 [SMILES: C[C@H]1[C@@H](c2cc(F)cc(Br)c2)OC(=O)N1C(=O)NCc1cncc2ccccc12] | (4S,5R)-5-(3-bromo-5-fluorophenyl)-N-(isoquinolin-4-ylmethyl)-4-methyl-2-oxo-1,3-oxazolidine-3-carboxamide | 458.05; 460.05 | 458.16; 460.16 |

TABLE 1-continued

The compounds in Examples 2-49 were prepared according to the procedure of Example 1.

| Example Number | Structure | Name | Calc'd Mass M + H⁺ | Observed Mass M + H⁺ |
|---|---|---|---|---|
| 26 | 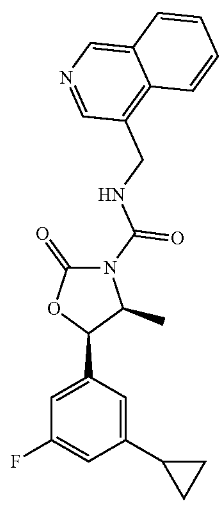 [SMILES: C[C@H]1[C@@H](c2cc(F)cc(C3CC3)c2)OC(=O)N1C(=O)NCc1cncc2ccccc12] | (4S,5R)-5-(3-cyclopropyl-5-fluorophenyl)-N-(isoquinolin-4-ylmethyl)-4-methyl-2-oxo-1,3-oxazolidine-3-carboxamide | 420.17 | 420.16 |
| 27 | 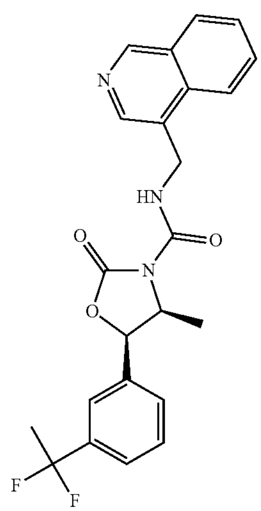 [SMILES: C[C@H]1[C@@H](c2cccc(C(C)(F)F)c2)OC(=O)N1C(=O)NCc1cncc2ccccc12] | (4S,5R)-5-[3-(1,1-difluoroethyl)phenyl]-N-(isoquinolin-4-ylmethyl)-4-methyl-2-oxo-1,3-oxazolidine-3-carboxamide | 426.16 | 426.12 |
| 28 | 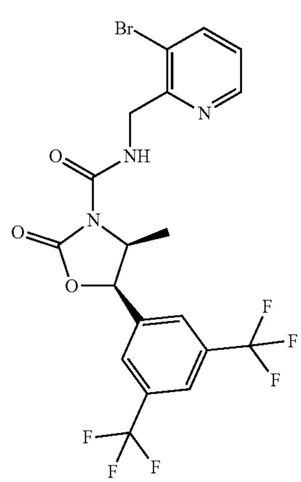 [SMILES: C[C@H]1[C@@H](c2cc(C(F)(F)F)cc(C(F)(F)F)c2)OC(=O)N1C(=O)NCc1ncccc1Br] | (4S,5R)-5-[3,5-bis(trifluoromethyl)phenyl]-N-[(3-bromopyridin-2-yl)methyl]-4-methyl-2-oxo-1,3-oxazolidine-3-carboxamide | 526.02 | 525.94 |

TABLE 1-continued

The compounds in Examples 2-49 were prepared according to the procedure of Example 1.

| Example Number | Structure | Name | Calc'd Mass M + H⁺ | Observed Mass M + H⁺ |
|---|---|---|---|---|
| 29 | 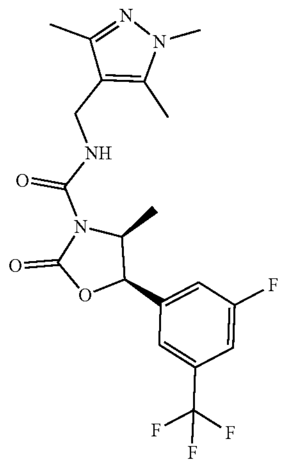 [SMILES: Cc1nn(C)c(C)c1CNC(=O)N1C(=O)O[C@H](c2cc(F)cc(C(F)(F)F)c2)[C@@H]1C] | (4S,5R)-5-[3-fluoro-5-(trifluoromethyl)phenyl]-4-methyl-2-oxo-N-[(1,3,5-trimethyl-1H-pyrazol-4-yl)methyl]-1,3-oxazolidine-3-carboxamide | 429.15 | 429.20 |
| 30 | 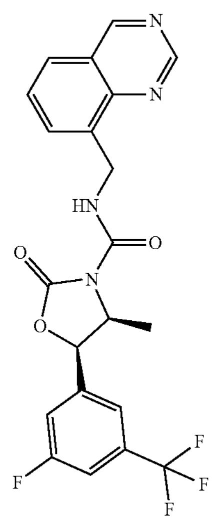 [SMILES: C[C@H]1[C@@H](c2cc(F)cc(C(F)(F)F)c2)OC(=O)N1C(=O)NCc1cccc2cncnc12] | (4S,5R)-5-[3-fluoro-5-(trifluoromethyl)phenyl]-4-methyl-2-oxo-N-(quinazolin-8-ylmethyl)-1,3-oxazolidine-3-carboxamide | 449.37 | 449.10 |
| 31 | 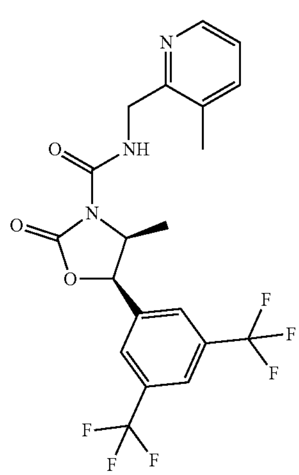 [SMILES: Cc1cccnc1CNC(=O)N1C(=O)O[C@H](c2cc(C(F)(F)F)cc(C(F)(F)F)c2)[C@@H]1C] | (4S,5R)-5-[3,5-bis(trifluoromethyl)phenyl]-4-methyl-N-[(3-methylpyridin-2-yl)methyl]-2-oxo-1,3-oxazolidine-3-carboxamide | 462.13 | 462.00 |

TABLE 1-continued

The compounds in Examples 2-49 were prepared according to the procedure of Example 1.

| Example Number | Structure | Name | Calc'd Mass M + H⁺ | Observed Mass M + H⁺ |
|---|---|---|---|---|
| 32 | 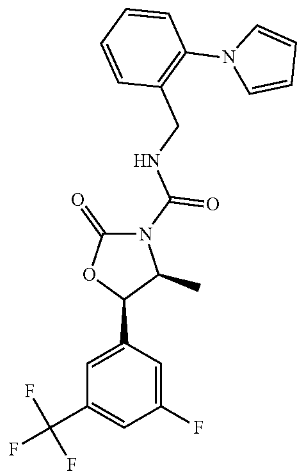 [SMILES: C[C@H]1[C@@H](c2cc(F)cc(C(F)(F)F)c2)OC(=O)N1C(=O)NCc1ccccc1-n1cccc1] | (4S,5R)-5-[3-fluoro-5-(trifluoromethyl)phenyl]-4-methyl-2-oxo-N-[2-(1H-pyrrol-1-yl)benzyl]-1,3-oxazolidine-3-carboxamide | 462.14 | 462.19 |
| 33 | 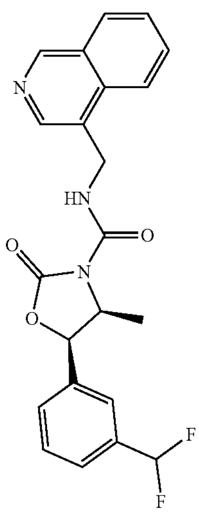 [SMILES: C[C@H]1[C@@H](c2cccc(C(F)F)c2)OC(=O)N1C(=O)NCc1cncc2ccccc12] | (4S,5R)-5-[3-(difluoromethyl)phenyl]-N-(isoquinolin-4-ylmethyl)-4-methyl-2-oxo-1,3-oxazolidine-3-carboxamide | 412.15 | 412.26 |
| 34 | 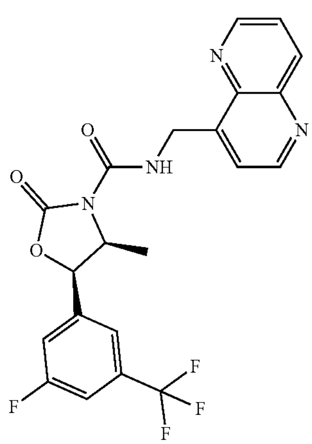 | (4S,5R)-5-[3-fluoro-5-(trifluoromethyl)phenyl]-4-methyl-N-(1,5-naphthyridin-4-ylmethyl)-2-oxo-1,3-oxazolidine-3-carboxamide | 449.12 | 449.00 |

TABLE 1-continued

The compounds in Examples 2-49 were prepared according to the procedure of Example 1.

| Example Number | Structure | Name | Calc'd Mass M + H⁺ | Observed Mass M + H⁺ |
|---|---|---|---|---|
| 35 | 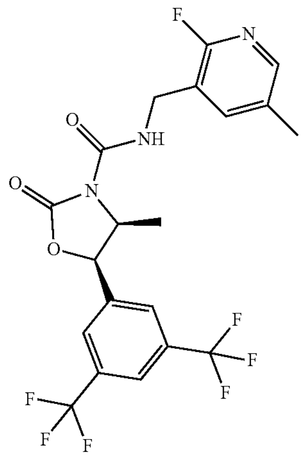 [SMILES: Cc1cnc(F)c(CNC(=O)N2C(=O)O[C@H](c3cc(C(F)(F)F)cc(C(F)(F)F)c3)[C@@H]2C)c1] | (4S,5R)-5-[3,5-bis(trifluoromethyl)phenyl]-N-[(2-fluoro-5-methylpyridin-3-yl)methyl]-4-methyl-2-oxo-1,3-oxazolidine-3-carboxamide | 480.12 | 480.00 |
| 36 | 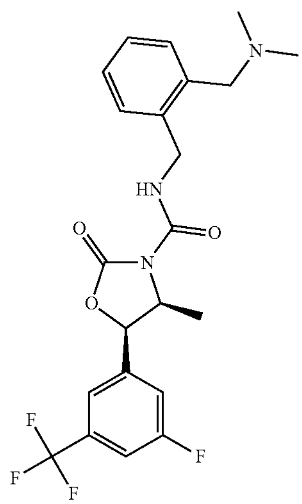 [SMILES: C[C@H]1[C@@H](c2cc(F)cc(C(F)(F)F)c2)OC(=O)N1C(=O)NCc1ccccc1CN(C)C] | (4S,5R)-N-{2-[(dimethylamino)methyl]benzyl}-5-[3-fluoro-5-(trifluoromethyl)phenyl]-4-methyl-2-oxo-1,3-oxazolidine-3-carboxamide | 454.18 | 454.24 |
| 37 | 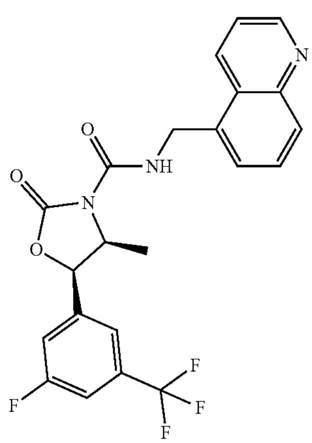 [SMILES: C[C@H]1[C@@H](c2cc(F)cc(C(F)(F)F)c2)OC(=O)N1C(=O)NCc1cccc2ncccc12] | (4S,5R)-5-[3-fluoro-5-(trifluoromethyl)phenyl]-4-methyl-2-oxo-N-(quinolin-5-ylmethyl)-1,3-oxazolidine-3-carboxamide | 448.12 | 448.10 |

TABLE 1-continued

The compounds in Examples 2-49 were prepared according to the procedure of Example 1.

| Example Number | Structure | Name | Calc'd Mass M + H⁺ | Observed Mass M + H⁺ |
|---|---|---|---|---|
| 38 | 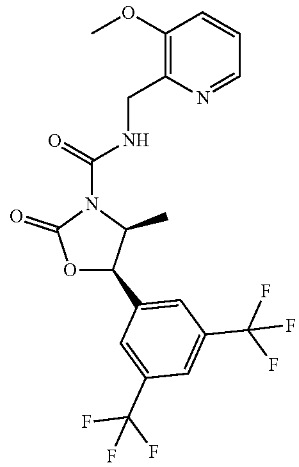 [SMILES: COc1cccnc1CNC(=O)N1C(=O)O[C@H](c2cc(C(F)(F)F)cc(C(F)(F)F)c2)[C@@H]1C] | (4S,5R)-5-[3,5-bis(trifluoromethyl)phenyl]-N-[(3-methoxypyridin-2-yl)methyl]-4-methyl-2-oxo-1,3-oxazolidine-3-carboxamide | 478.36 | 478.15 |
| 39 | 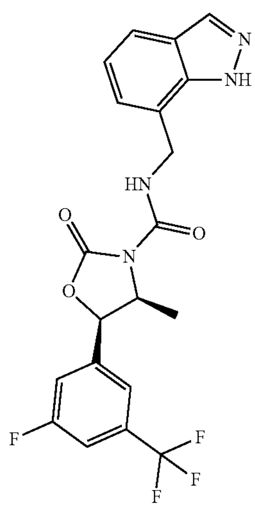 [SMILES: C[C@H]1[C@@H](c2cc(F)cc(C(F)(F)F)c2)OC(=O)N1C(=O)NCc1cccc2cn[nH]c12] | (4S,5R)-5-[3-fluoro-5-(trifluoromethyl)phenyl]-N-(1H-indazol-7-ylmethyl)-4-methyl-2-oxo-1,3-oxazolidine-3-carboxamide | 437.36 | 437.10 |
| 40 | 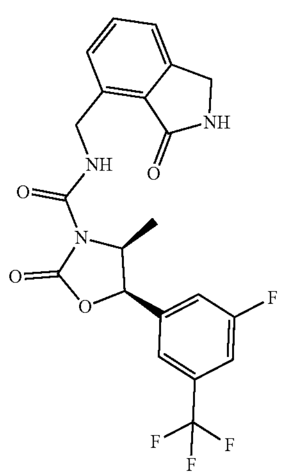 [SMILES: C[C@H]1[C@@H](c2cc(F)cc(C(F)(F)F)c2)OC(=O)N1C(=O)NCc1cccc2c1C(=O)NC2] | (4S,5R)-5-[3-fluoro-5-(trifluoromethyl)phenyl]-4-methyl-2-oxo-N-[(3-oxo-2,3-dihydro-1H-isoindol-4-yl)methyl]-1,3-oxazolidine-3-carboxamide | 452.12 | 452.20 |

TABLE 1-continued

The compounds in Examples 2-49 were prepared according to the procedure of Example 1.

| Example Number | Structure | Name | Calc'd Mass M + H⁺ | Observed Mass M + H⁺ |
|---|---|---|---|---|
| 41 | 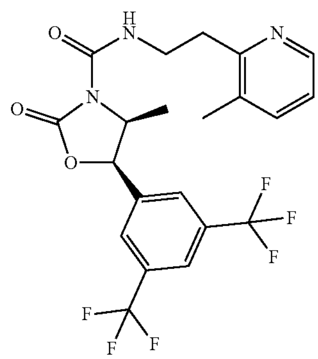 [SMILES: Cc1cccnc1CCNC(=O)N1C(=O)O[C@H](c2cc(C(F)(F)F)cc(C(F)(F)F)c2)[C@@H]1C] | (4S,5R)-5-[3,5-bis(trifluoromethyl)phenyl]-4-methyl-N-[2-(3-methylpyridin-2-yl)ethyl]-2-oxo-1,3-oxazolidine-3-carboxamide | 476.14 | 476.00 |
| 42 | 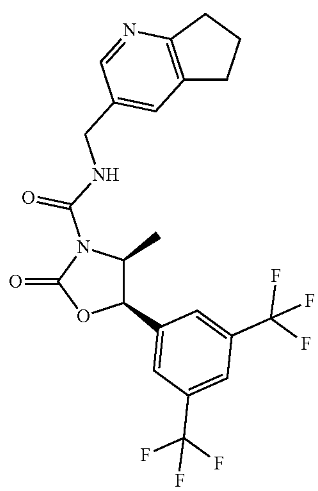 [SMILES: C[C@H]1[C@@H](c2cc(C(F)(F)F)cc(C(F)(F)F)c2)OC(=O)N1C(=O)NCc1cnc2c(c1)CCC2] | (4S,5R)-5-[3,5-bis(trifluoromethyl)phenyl]-N-(6,7-dihydro-5H-cyclopenta[b]pyridin-3-ylmethyl)-4-methyl-2-oxo-1,3-oxazolidine-3-carboxamide | 488.14 | 488.00 |
| 43 | 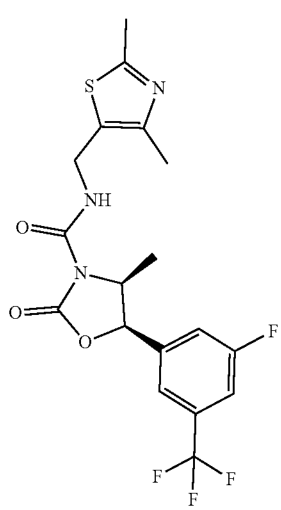 [SMILES: Cc1nc(C)c(CNC(=O)N2C(=O)O[C@H](c3cc(F)cc(C(F)(F)F)c3)[C@@H]2C)s1] | (4S,5R)-N-[(2,4-dimethyl-1,3-thiazol-5-yl)methyl]-5-[3-fluoro-5-(trifluoromethyl)phenyl]-4-methyl-2-oxo-1,3-oxazolidine-3-carboxamide | 432.09 | 432.20 |

TABLE 1-continued

The compounds in Examples 2-49 were prepared according to the procedure of Example 1.

| Example Number | Structure | Name | Calc'd Mass M + H⁺ | Observed Mass M + H⁺ |
|---|---|---|---|---|
| 44 | 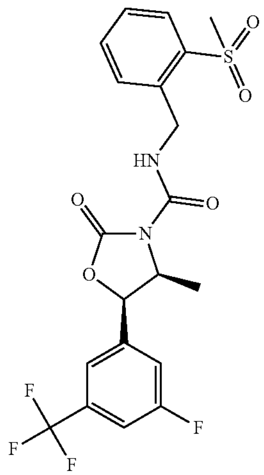 [SMILES: C[C@H]1[C@@H](c2cc(F)cc(C(F)(F)F)c2)OC(=O)N1C(=O)NCc1ccccc1S(C)(=O)=O] | (4S,5R)-5-[3-fluoro-5-(trifluoromethyl)phenyl]-4-methyl-N-[2-(methylsulfonyl)benzyl]-2-oxo-1,3-oxazolidine-3-carboxamide | 475.10 | 475.14 |
| 45 | 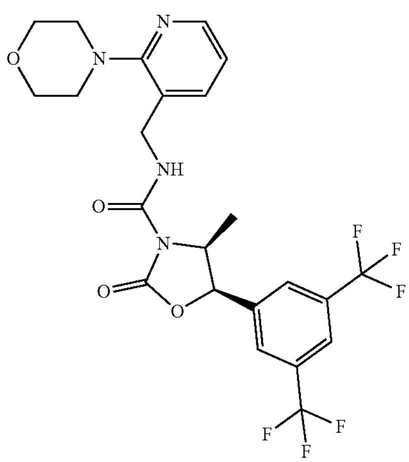 [SMILES: C[C@H]1[C@@H](c2cc(C(F)(F)F)cc(C(F)(F)F)c2)OC(=O)N1C(=O)NCc1cccnc1N1CCOCC1] | (4S,5R)-5-[3,5-bis(trifluoromethyl)phenyl]-4-methyl-N-[(2-morpholin-4-ylpyridin-3-yl)methyl]-2-oxo 1,3-oxazolidine-3-carboxamide | 533.15 | 533.10 |
| 46 | 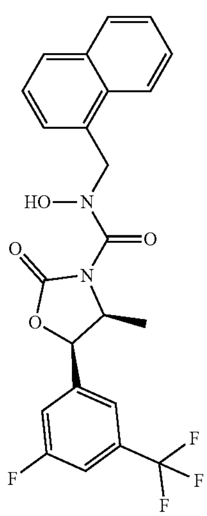 [SMILES: C[C@H]1[C@@H](c2cc(F)cc(C(F)(F)F)c2)OC(=O)N1C(=O)N(O)Cc1cccc2ccccc12] | (4S,5R)-5-[3-fluoro-5-(trifluoromethyl)phenyl]-N-hydroxy-4-methyl-N-(naphthalen-1-ylmethyl)-2-oxo-1,3-oxazolidine-3-carboxamide | 463.39 | 463.00 |

TABLE 1-continued

The compounds in Examples 2-49 were prepared according to the procedure of Example 1.

| Example Number | Structure | Name | Calc'd Mass M + H+ | Observed Mass M + H+ |
|---|---|---|---|---|
| 47 | 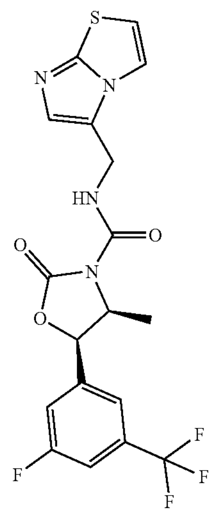 [SMILES: C[C@H]1[C@@H](c2cc(F)cc(C(F)(F)F)c2)OC(=O)N1C(=O)NCc1cnc2sccn12] | (4S,5R)-5-[3-fluoro-5-(trifluoromethyl)phenyl]-N-(imidazo[2,1-b][1,3]thiazol-5-ylmethyl)-4-methyl-2-oxo-1,3-oxazolidine-3-carboxamide | 443.39 | 443.05 |
| 48 | 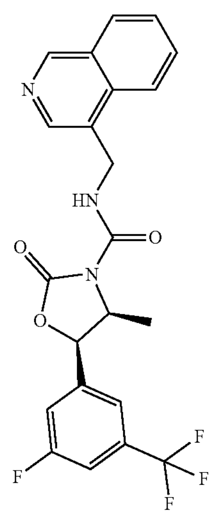 | (4S,5R)-5-[3-fluoro-5-(trifluoromethyl)phenyl]-N-(isoquinolin-4-ylmethyl)-4-methyl-2-oxo-1,3-oxazolidine-3-carboxamide | 448.38 | 448.11 |
| 49 | 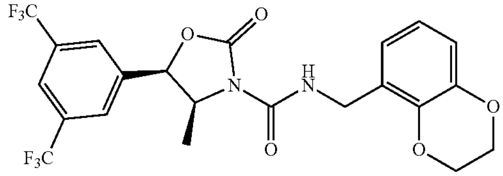 [SMILES: C[C@H]1[C@@H](c2cc(C(F)(F)F)cc(C(F)(F)F)c2)OC(=O)N1C(=O)NCc1cccc2c1OCCO2] | (4S,5R)-5-[3,5-bis(trifluoromethyl)phenyl]-N-(2,3-dihydro-1,4-benzodioxin-5-ylmethyl)-4-methyl-2-oxo-1,3-oxazolidine-3-carboxamide | 505.12 | 504.90 |

Example 50

(4S,5R)-5-(3,5-bis(trifluoromethyl)phenyl)-4-(hydroxymethyl)-N-(isoquinolin-4-ylmethyl)-2-oxooxazolidine-3-carboxamide

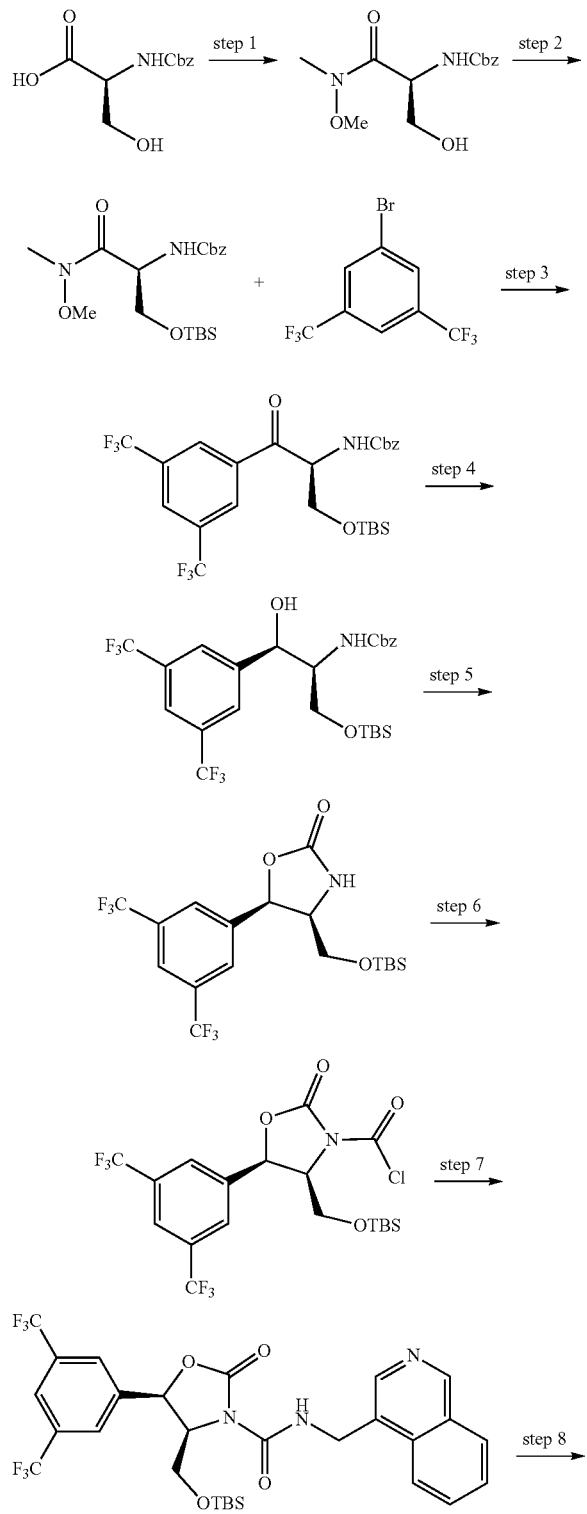

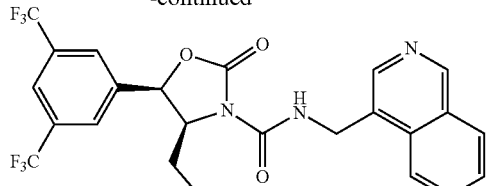

Example 50

Step 1: Benzyl (S)-(3-hydroxy-1-(methoxy(methyl) amino)-1-oxopropan-2-yl)carbamate To a solution of (benzyloxy)carbonyl)-L-serine (170.0 g, 0.8 mol) and HNMe (OMe) HCl (116.0 g, 0.9 mol) in DCM (1.8 L) was stirred at −15° C. for 5 min. Then NMM (220 mL, 0.9 mol) and EDCl (160.0 g, 0.9 mol) were added in portions to keep the temperature below −5° C. After addition, the mixture was stirred at −5° C. for 3 h. The reaction was quenched with ice-cooled 1 N HCl (800 mL). The organic phase was separated and washed with 1 N HCl (300 mL×2), saturated NaHCO$_3$, dried and concentrated to afford the title compound. $^1$H NMR (CDCl$_3$, 400 MHz): δ 7.36-7.31 (m, 5H), 5.91 (s, 1H), 5.11 (d, J=2.0 Hz, 2H), 4.87 (s, 1H), 3.85 (s, 2H), 3.77 (s, 3H), 3.22 (s, 3H). LC-MS m/z [M+H]$^+$ 282.90 (calc'd 283.12).

Step 2: benzyl (S)-(3,8,8,9,9-pentamethyl-4-oxo-2,7-dioxa-3-aza-8-siladecan-5-yl)carbamate To a solution of benzyl (S)-(3-hydroxy-1-(methoxy(methyl)amino)-1-oxopropan-2-yl)carbamate (20.0 g, 72 mmol) in DCM (400 mL) was added imidazole (12.0 g, 176 mmol) and TBDMSCl (16.0 g, 106 mmol). After stirring at rt for 2 h, the mixture was quenched with aqueous NH$_4$Cl, extracted with DCM, washed with water, brine, dried, concentrated and purified by flash chromatography (hexane:EtOAc=15:1) to afford the title compound. $^1$H NMR (CDCl$_3$, 400 MHz): δ 7.36-7.29 (m, 5H), 5.63 (s, 1H), 5.14-5.06 (m, 2H), 4.81 (s, 1H), 3.90-3.80 (m, 2H), 3.73 (s, 3H), 3.21 (s, 3H), 0.83 (s, 9H), 0.01 (s, 6H). LC-MS m/z [M+H]$^+$ 396.90 (calc'd 396.21).

Step 3: benzyl (S)-(1-(3,5-bis(trifluoromethyl)phenyl)-3-((tert-butyldimethylsilyl)oxy)-1-oxopropan-2-yl)carbamate A mixture of benzyl (S)-(3,8,8,9,9-pentamethyl-4-oxo-2,7-dioxa-3-aza-8-siladecan-5-yl)carbamate (23.0 g, 58 mmol), 1-bromo-3,5-bis-trifluoromethylbenzene (27.0 g, 70 mmol) in anhydrous THF (200 mL) was stirred at −10° C. for 5 min. Then iPrMgCl (73 mL, 2 M in THF) was added dropwise to keep the temperature below −5° C. After addition, the mixture was stirred at rt overnight. The mixture was quenched by 3 N HCl, extracted with EtOAc, washed with water. The organic layer was evaporated and purified by flash chromatography (Petroleum ether:EtOAc=10:1) to afford the title compound. $^1$H NMR (CDCl$_3$, 400 MHz): δ 8.37 (s, 2H), 8.08 (s, 1H), 7.37-7.34 (m, 5H), 5.84 (d, J=4.0 Hz, 1H), 5.39-5.37 (m, 1H), 5.13 (s, 2H), 4.02-3.84 (m, 2H), 0.70 (s, 9H), −0.10 (d, J=5.6 Hz, 6H). LC-MS m/z [M+H]$^+$ 549.90 (calc'd 550.18).

Step 4: Benzyl ((1R,2S)-1-(3,5-bis(trifluoromethyl)phenyl)-3-((tert-butyldimethylsilyl)oxy)-1-hydroxypropan-2-yl)carbamate A mixture of benzyl (S)-(1-(3,5-bis(trifluoromethyl)phenyl)-3-((tert-butyldimethylsilyl)oxy)-1-oxopropan-2-yl)carbamate (10.0 g, 18 mmol), Al(OiPr)$_3$ (3.9 g, 18 mmol), iPrOH (15.6 mL, 198 mmol) in anhydrous toluene (200 mL) was stirred at 60° C. overnight. Cooled to rt, the mixture was washed with water, dried and concentrated. It was purified by flash chromatography (Petroleum ether:EtOAc=5:1) to afford the title compound. $^1$H NMR (CDCl₃, 400 MHz): δ 7.89-7.79 (m, 3H), 7.40-7.31 (m, 5H), 5.60 (s, 1H), 5.15-5.03 (m, 2H), 4.45-4.35 (m, 1H), 3.95 (s, 1H), 3.69-3.61 (m, 2H), 0.91 (s, 9H), 0.04 (d, J=5.6 Hz, 6H). LC-MS m/z [M+H]⁺ 551.90 (calc'd 552.19).

Step 5: (4S,5R)-5-(3,5-bis(trifluoromethyl)phenyl)-4-(((tert-butyldimethylsilyl)oxy)-methyl)oxazolidin-2-one A mixture of benzyl ((1R,2S)-1-(3,5-bis(trifluoromethyl)phenyl)-3-((tert-butyldimethylsilyl)oxy)-1-hydroxypropan-2-yl)carbamate (20.0 g, 36 mmol), KOH (20 mL, 48% aq.) in toluene (200 mL) was stirred at rt overnight. The mixture was diluted with EtOAc, washed with water and brine, purified by flash chromatography (Petroleum ether:EtOAc=5:1) to afford the title compound. ¹H NMR (CDCl₃, 400 MHz): δ 7.88 (s, 1H), 7.84 (s, 2H), 5.86 (s, 1H), 5.77 (s, 1H), 4.17 (t, J=4.2 Hz, 1H), 3.29-3.21 (m, 2H), 0.769 (s, 9H), −0.11 (d, J=5.6 Hz, 6H). LC-MS m/z [M+H]⁺ 443.90 (calc'd 444.14).

Step 6: (4S,5R)-5-(3,5-bis(trifluoromethyl)phenyl)-4-(((tert-butyldimethylsilyl)oxy)methyl)-2-oxooxazolidine-3-carbonyl chloride N-Butyl lithium (0.39 mL, 2.5 M in hexane, 0.96 mmol) was added slowly to a stirred mixture of (4S,5R)-5-(3,5-bis(trifluoromethyl)phenyl)-4-(((tert-butyldimethylsilyl)oxy)methyl)oxazolidin-2-one (200.0 mg, 0.96 mmol) in THF (5 mL) and the mixture was stirred at 0° C. for 20 min. The mixture was cooled to −78° C., and trichloromethyl chloroformate (0.23 mL, 0.96 mmol) was added rapidly, and stirred another 30 min. The mixture was allowed to warm to rt. The solvent and generated phosgene was removed by vacuum. The crude product was taken directly to the next step without further purification.

Step 7: (4S,5R)-5-(3,5-bis(trifluoromethyl)phenyl)-4-(((tert-butyldimethylsilyl)oxy)methyl)-N-(isoquinolin-4-ylmethyl)-2-oxooxazolidine-3-carboxamide Isoquinolin-4-ylmethanamine (107.0 mg, 0.68 mmol) was added to a stirred mixture of (4S,5R)-5-(3,5-bis(trifluoromethyl)phenyl)-4-(((tert-butyldimethylsilyl)oxy)methyl)-2-oxooxazolidine-3-carbonyl chloride (228.0 mg, 0.45 mmol) in DCM (5 mL) and triethylamine (0.23 mL, 1.80 mmol) and water (2 drops) and the mixture was stirred from 0° C. to rt overnight. The reaction mixture was diluted with DCM (10 mL) and washed with water (10 mL). Collected organic layer, dried with Na₂SO₄, filtered and concentrated. The crude product was purified by flash chromatography (0% to 50% EtOAc in hexane) to give the title compound.

Step 8: (4S,5R)-5-(3,5-bis(trifluoromethyl)phenyl)-4-(hydroxymethyl)-N-(isoquinolin-4-ylmethyl)-2-oxooxazolidine-3-carboxamide Acetyl chloride (0.01 mL, 0.19 mmol) was added to a stirred mixture of (4S,5R)-5-(3,5-bis(trifluoromethyl)phenyl)-4-(((tert-butyldimethylsilyl)oxy)methyl)-N-(isoquinolin-4-ylmethyl)-2-oxooxazolidine-3-carboxamide (100.0 mg, 0.16 mmol) in MeOH (5 mL) and reaction was stirred at rt for 2 h. The reaction mixture was diluted with DCM (10 mL) and washed with water (10 mL). The organic layers were combined, dried with Na₂SO₄, filtered and concentrated. The crude product was purified by flash chromatography (0% to 50% EtOAc in hexane) to give the title compound. LC-MS m/z [M+H]⁺ 514.04 (calc'd 514.12).

TABLE 2

The compounds in Examples 51-59* were prepared according to the procedure of Example 50.

| Example Number | Structure | Name | Calc'd Mass M + H⁺ | Observed Mass M + H⁺ |
|---|---|---|---|---|
| 51 | 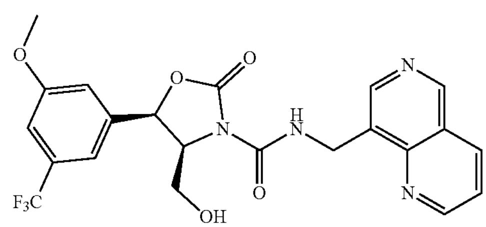 [SMILES: COc1cc([C@H]2OC(=O)N(C(=O)NCc3cncc4cccnc34)[C@H]2CO)cc(C(F)(F)F)c1] | (4S,5R)-4-(hydroxymethyl)-5-[3-methoxy-5-(trifluoromethyl)phenyl]-N-(1,6-naphthyridin-8-ylmethyl)-2-oxo-1,3-oxazolidine-3-carboxamide | 477.14 | 476.71 |
| 52 | 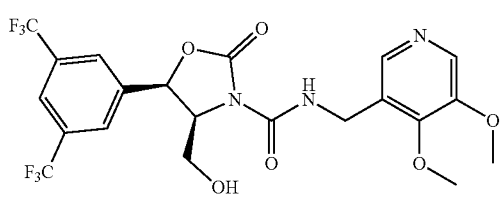 [SMILES: COc1cncc(CNC(=O)N2C(=O)O[C@H](c3cc(C(F)(F)F)cc(C(F)(F)F)c3)[C@@H]2CO)c1OC] | (4S,5R)-5-[3,5-bis(trifluoromethyl)phenyl]-N-(2,3-dimethoxybenzyl)-4-(hydroxymethyl)-2-oxo-1,3-oxazolidine-3-carboxamide | 523.13 | 523.30 |
| 53 | 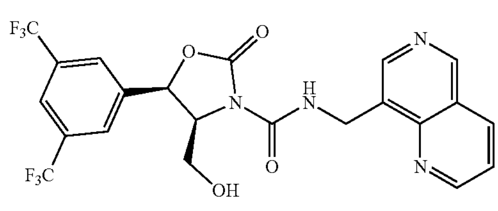 [SMILES: O=C(NCc1cncc2cccnc12)N1C(=O)O[C@H](c2cc(C(F)(F)F)cc(C(F)(F)F)c2)[C@@H]1CO] | (4S,5R)-5-[3,5-bis(trifluoromethyl)phenyl]-4-(hydroxymethyl)-N-(1,6-naphthyridin-8-ylmethyl)-2-oxo-1,3-oxazolidine-3-carboxamide | 515.12 | 515.12 |

TABLE 2-continued

The compounds in Examples 51-59* were prepared according to the procedure of Example 50.

| Example Number | Structure | Name | Calc'd Mass M + H⁺ | Observed Mass M + H⁺ |
|---|---|---|---|---|
| 54 | 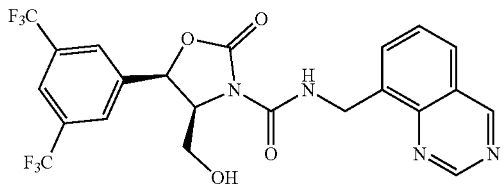 [SMILES: O=C(NCc1cccc2cncnc12)N1C(=O)O[C@H](c2cc(C(F)(F)F)cc(C(F)(F)F)c2)[C@@H]1CO] | (4S,5R)-5-[3,5-bis(trifluoromethyl)phenyl]-4-(hydroxymethyl)-2-oxo-N-(quinazolin-8-ylmethyl)-1,3-oxazolidine-3-carboxamide | 515.12 | 515.40 |
| 55 | 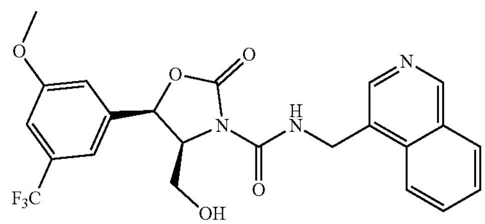 [SMILES: COc1cc([C@H]2OC(=O)N(C(=O)NCc3cncc4ccccc34)[C@H]2CO)cc(C(F)(F)F)c1] | (4S,5R)-4-(hydroxymethyl)-N-(isoquinolin-4-ylmethyl)-5-[3-methoxy-5-(trifluoromethyl)phenyl]-2-oxo-1,3-oxazolidine-3-carboxamide | 476.42 | 476.28 |
| 56 | 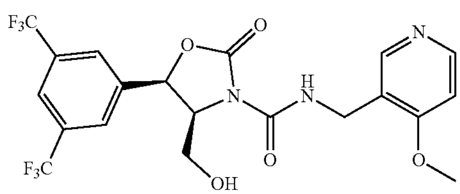 [SMILES: COc1ccncc1CNC(=O)N1C(=O)O[C@H](c2cc(C(F)(F)F)cc(C(F)(F)F)c2)[C@@H]1CO] | (4S,5R)-5-[3,5-bis(trifluoromethyl)phenyl]-4-(hydroxymethyl)-N-(2-methoxybenzyl)-2-oxo-1,3-oxazolidine-3-carboxamide | 493.12 | 493.85 |
| 57 | 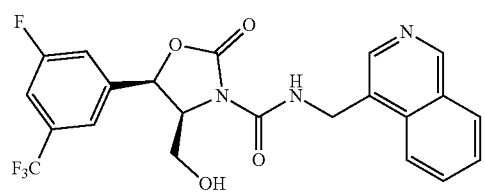 [SMILES: O=C(NCc1cncc2ccccc12)N1C(=O)O[C@H](c2cc(F)cc(C(F)(F)F)c2)[C@@H]1CO] | (4S,5R)-5-[3-fluoro-5-(trifluoromethyl)phenyl]-4-(hydroxymethyl)-N-(isoquinolin-4-ylmethyl)-2-oxo-1,3-oxazolidine-3-carboxamide | 464.12 | 464.26 |
| 58 | 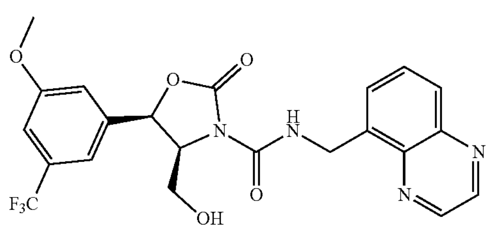 [SMILES: COc1cc([C@H]2OC(=O)N(C(=O)NCc3cccc4nccnc34)[C@H]2CO)cc(C(F)(F)F)c1] | (4S,5R)-4-(hydroxymethyl)-5-[3-methoxy-5-(trifluoromethyl)phenyl]-2-oxo-N-(quinoxalin-5-ylmethyl)-1,3-oxazolidine-3-carboxamide | 477.13 | 477.28 |
| 59 | 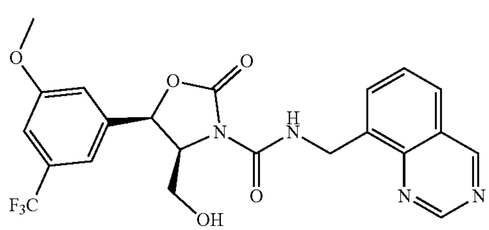 [SMILES: COc1cc([C@H]2OC(=O)N(C(=O)NCc3cccc4cncnc34)[C@H]2CO)cc(C(F)(F)F)c1] | (4S,5R)-4-(hydroxymethyl)-5-[3-methoxy-5-(trifluoromethyl)phenyl]-2-oxo-N-(quinazolin-8-ylmethyl)-1,3-oxazolidine-3-carboxamide | 477.13 | 477.15 |

*The compounds in Examples 50-59 were purified using either flash chromatography or by mass triggered HPLC using the following conditions: column: Waters Sunfire C18, 5u, 19 × 100 mm; solvent: gradient range: 10-15% initial to 70-98% final MeCN (either 0.1% formic acid or TFA) in water (0.1% formic acid or TFA) 50 mL/min, 8 min run time.

Example 60

(4S,5S)—N-((1,6-naphthyridin-8-yl)methyl)-5-(6-methoxy-4-(trifluoromethyl)pyridin-2-yl)-4-methyl-2-oxooxazolidine-3-carboxamide

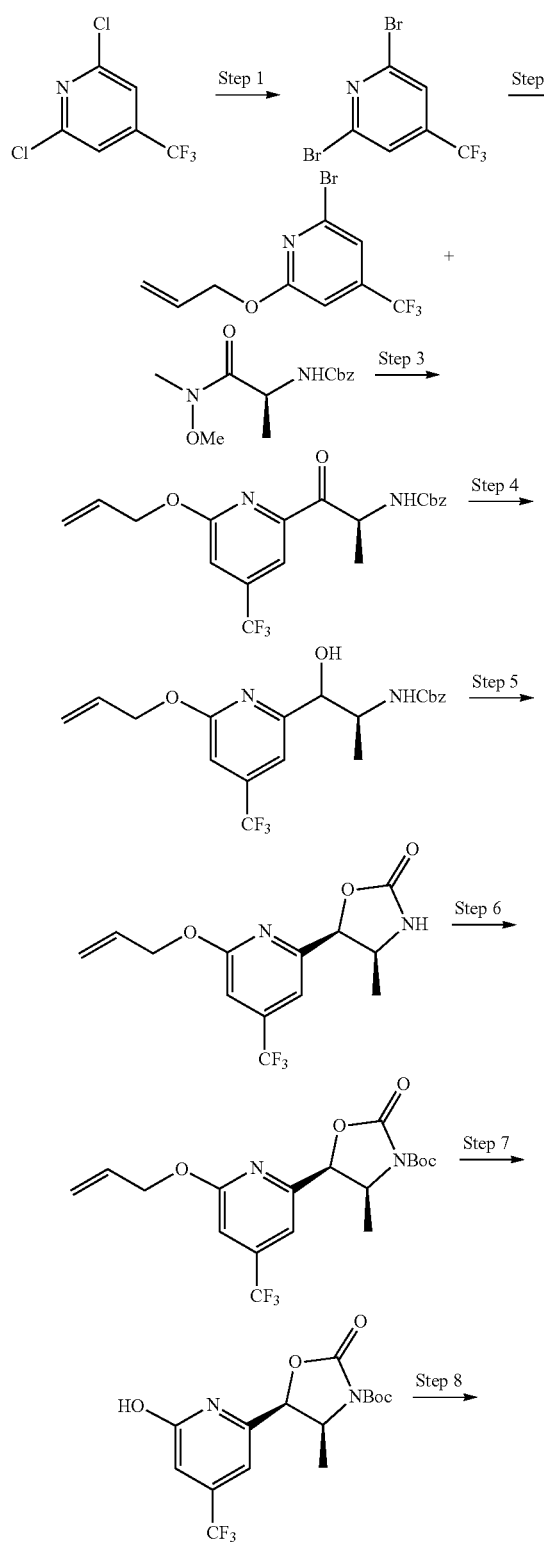

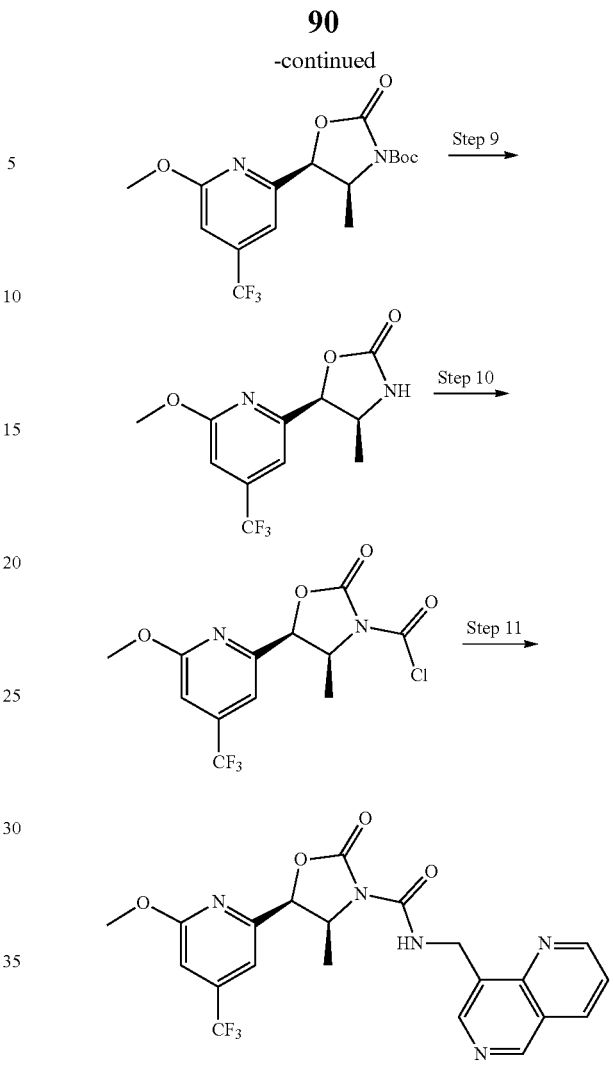

Example 60

Step 1: 2,6-dibromo-4-(trifluoromethyl)pyridine A mixture of 2,6-dichloro-4-(trifluoromethyl)pyridine (5.0 g, 23.2 mmol) and 30% HBr in acetic acid (4 mL) were heated at 100° C. for 24 h in a sealed tube. The reaction mixture was cooled to 0° C., neutralized with 6 N NaOH and extracted with diethyl ether. The ether layer was evaporated and crude product was purified by flash chromatography (0% to 10% EtOAc in hexane) to provide the title compound.

Step 2: 2-(allyloxy)-6-bromo-4-(trifluoromethyl)pyridine To a solution of prop-2-en-1-ol (3.6 mL, 52.5 mmol) in THF (40 mL) was added NaH (2.1 g, 52.5 mmol) portion wise at 0° C. The resulting solution was slowly warmed to rt and stirred for 10 min. Then the reaction mixture was cooled to 0° C. and was added a solution of 2,6-dibromo-4-(trifluoromethyl)pyridine (16.0 g, 52.5 mmol) in THF (50 mL). The resulting mixture was slowly warmed to rt and stirred for 30 min. The reaction was diluted with NH₄Cl, then extracted with ethyl acetate, and purified by flash chromatography (0% to 10% EtOAc in hexane) to provide the title compound.

Step 3: benzyl (S)-(1-(6-(allyloxy)-4-(trifluoromethyl)pyridin-2-yl)-1-oxopropan-2-yl)carbamate To a solution of nBuLi (18.0 mL, 45.1 mmol) in THF (25 mL) was added a solution of 2-(allyloxy)-6-bromo-4-(trifluoromethyl)pyridine (12.7 g, 45.1 mmol) in THF (20 mL) at −78° C. The resulting solution was stirred at −78° C. for 20 min and then was added a solution of (S)-benzyl (1-(methoxy(methyl)amino)-1-oxopropan-2-yl)carbamate (6.0 g, 22.5 mmol) in 20 mL THF. The reaction was slowly warmed to 0° C. over 1 h, and quenched with NH$_4$Cl, extracted with ethyl acetate and purified using flash chromatography (0% to 100% EtOAc in hexane to provide the title compound. LC-MS m/z [M+H]$^+$ 409.25 (calc'd 409.13).

Step 4: benzyl ((1S,2S)-1-(6-(allyloxy)-4-(trifluoromethyl)pyridin-2-yl)-1-hydroxypropan-2-yl)carbamate To a solution of (S)-benzyl (1-(6-(allyloxy)-4-(trifluoromethyl)pyridin-2-yl)-1-oxopropan-2-yl)carbamate (5.0 g, 12.2 mmol) in the mixture of toluene (10 mL) and 2-propanol (5 mL) was added aluminum isopropoxide (0.5 g, 2.4 mmol), and the resulting solution was heated at 50° C. for 4 h when the LCMS indicated the completion of reaction. The reaction mixture was diluted with brine and extracted with ethyl acetate. The organic layer was dried with MgSO$_4$, evaporated and purified by flash chromatography (0% to 10% EtOAc in hexane, 80 g Redisep™ column) to provide the title compound. LC-MS m/z [M+H]$^+$ 411.26 (calc'd 411.13).

Step 5: (4S,5S)-5-(6-(allyloxy)-4-(trifluoromethyl)pyridin-2-yl)-4-methyloxazolidin-2-one To a solution of benzyl (1S,2S)-1-(6-(allyloxy)-4-(trifluoromethyl)pyridin-2-yl)-1-hydroxypropan-2-yl)carbamate (900.0 mg, 2.19 mmol) in THF (3 mL) was added potassium bis(trimethylsilyl)-amide (4.82 mL, 4.82 mmol) at −20° C. The reaction mixture was stirred at −20° C. for 10 min and slowly warmed to 0° C. Saturated ammonium chloride was added, and the resulting mixture was extracted with ethyl acetate. The reaction mixture was diluted with ethyl acetate, washed with saturated NaHCO$_3$, and then washed with brine. The organic layer was dried with MgSO$_4$, evaporated and purified by flash chromatography (0% to 10% EtOAc in hexane) to provide the title compound. LC-MS m/z [M+H]$^+$ 303.15 (calc'd 303.09).

Step 6: tert-butyl (4S,5S)-5-(6-(allyloxy)-4-(trifluoromethyl)pyridin-2-yl)-4-methyl-2-oxooxazolidine-3-carboxylate The mixture of (4S,5S)-5-(6-(allyloxy)-4-(trifluoromethyl)-pyridin-2-yl)-4-methyloxazolidin-2-one (300.0 mg, 0.99 mmol), BOC-Anhydride (461 μl, 1.98 mmol) and DMAP (24.2 mg, 0.20 mmol) were stirred in a sealed tube for 12 h. The reaction mixture was diluted with DCM and directly loaded into column and purified by flash chromatography (0% to 10% EtOAc in hexane) to provide the title compound. LC-MS m/z [2M+H]$^+$ 805.49 (calc'd 805.28).

Step 7: tert-butyl (4S,5S)-5-(6-hydroxy-4-(trifluoromethyl)pyridin-2-yl)-4-methyl-2-oxooxazolidine-3-carboxylate To a solution of (4S,5S)-tert-butyl 5-(6-(allyloxy)-4-(trifluoromethyl)pyridin-2-yl)-4-methyl-2-oxooxazolidine-3-carboxylate (400.0 mg, 0.99 mmol) in DCM (2 mL) was added Pd(Ph$_3$)$_4$ (115.0 mg, 0.10 mmol) followed by 1,3-dimethylpyrimidine-2,4,6(1H,3H,5H)-trione (466.0 mg, 2.98 mmol). The resulting mixture was cooled to −78° C. and degassed and back filled with nitrogen. This process was repeated three times. Then the reaction mixture was warmed to rt and stirred at rt for 12 h. The reaction mixture was diluted with ethyl acetate, washed with saturated NaHCO$_3$. The organic layer was evaporated to dryness and purified by flash chromatography (0% to 10% EtOAc in hexane) to provide the title compound. LC-MS m/z [2M+H]$^+$ 725.42 (calc'd 725.22).

Step 8: tert-butyl (4S,5S)-5-(6-methoxy-4-(trifluoromethyl)pyridin-2-yl)-4-methyl-2-oxooxazolidine-3-carboxylate To a solution of (4S,5S)-tert-butyl 5-(6-hydroxy-4-(trifluoromethyl)pyridin-2-yl)-4-methyl-2-oxooxazolidine-3-carboxylate (200.0 mg, 0.55 mmol) in DMF (2 mL) was added CsF (252.0 mg, 1.66 mmol) and iodomethane (0.1 mL, 1.66 mmol). The resulting solution was stirred at rt for 12 h. The reaction mixture was quenched with NH$_4$Cl, then diluted with ethyl acetate, then washed with brine. The organic layer was evaporated to dryness, and crude was purified by flash chromatography (0% to 10% EtOAc in hexane) to provide the title compound.

Step 9: (4S,5S)-5-(6-methoxy-4-(trifluoromethyl)pyridin-2-yl)-4-methyloxazolidin-2-one To a solution of (tert-butyl (4S,5S)-5-(6-methoxy-4-(trifluoromethyl)pyridin-2-yl)-4-methyl-2-oxooxazolidine-3-carboxylate (536.0 mg, 1.42 mmol) in DCM (5 mL) was added trifluoroacetic acid (545 μL, 7.12 mmol) and the mixture was stirred at rt for 12 h. The reaction was quenched with saturated NaHCO$_3$(5 mL), extracted with DCM, dried over MgSO$_4$, and concentrated to provide the title compound, which was used in the next step without further purification.

Step 10: (4S,5S)-5-(6-methoxy-4-(trifluoromethyl)pyridin-2-yl)-4-methyl-2-oxooxazolidine-3-carbonyl chloride n-Butyllithium (0.83 mL, 2.07 mmol) was added to a stirred mixture of (4S,5S)-5-(6-methoxy-4-(trifluoromethyl)pyridin-2-yl)-4-methyloxazolidin-2-one (382.0 mg, 1.38 mmol) in THF at 0° C., and the resulting mixture was stirred for 30 min. Then, the reaction mixture was cooled to −78° C., trichloromethyl carbonochloridate (0.25 mL, 2.00 mmol) was added rapidly, stirred for 30 min at −78° C. The crude was dried on rotavap to give the title compound, which was used in the next step without further purification.

Step 11: (4S,5S)—N-((1,6-naphthyridin-8-yl)methyl)-5-(6-methoxy-4-(trifluoromethyl)pyridin-2-yl)-4-methyl-2-oxooxazolidine-3-carboxamide (4S,5S)-5-(6-methoxy-4-(trifluoromethyl)-pyridin-2-yl)-4-methyl-2-oxooxazolidine-3-carbonyl chloride from step 10 (156.0 mg, 0.46 mmol) was added to a stirred mixture of (1,6-naphthyridin-8-yl)methanamine.3HCl (247.0 mg, 0.92 mmol) and trimethylamine (0.51 mL, 3.69 mmol) in DCM and the mixture was stirred at rt for 4 h. The reaction mixture was concentrated and the residue was purified by flash chromatography (0% to 100% EtOAc in hexane) to give the title compound. LC-MS m/z [M+H]$^+$ 462.19 (calc'd 462.39).

TABLE 3

The compounds in Examples 61-62* were prepared according to the procedure of Example 60.

| Example Number | Structure | Name | Calc'd Mass M + H+ | Observed Mass M + H+ |
|---|---|---|---|---|
| 61 | 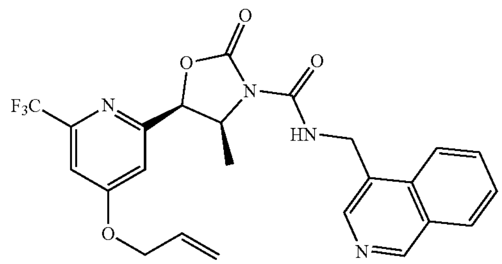 [SMILES: C=CCOc1cc([C@H]2OC(=O)N(C(=O)NCc3cncc4ccccc34)[C@H]2C)nc(C(F)(F)F)c1] | (4S,5S)-N-(isoquinolin-4-ylmethyl)-4-methyl-2-oxo-5-[6-(prop-2-en-1-yloxy)-4-(trifluoromethyl)pyridin-2-yl]-1,3-oxazolidine-3-carboxamide | 487.44 | 487.13 |
| 62 | 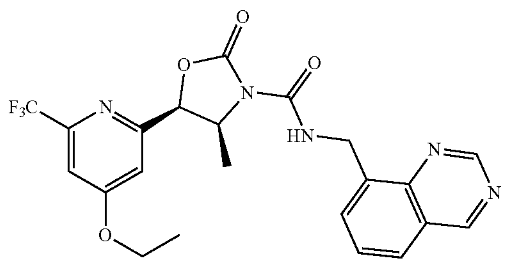 [SMILES: CCOc1cc([C@H]2OC(=O)N(C(=O)NCc3cccc4cncnc34)[C@H]2C)nc(C(F)(F)F)c1] | (4S,5S)-5-[6-ethoxy-4-(trifluoromethyl)pyridin-2-yl]-4-methyl-2-oxo-N-(quinazolin-8-ylmethyl)-1,3-oxazolidine-3-carboxamide | 476.42 | 476.18 |

*The compounds in Examples 60-62 were purified using either silica gel column chromatography or by mass triggered HPLC using the following conditions: column: Waters Sunfire C18, 5u, 19 × 100 mm; solvent: gradient range: 10-15% initial to 70-98% final MeCN (either 0.1% formic acid or TFA) in water (0.1% formic acid or TFA) 50 mL/min, 8 min run time.

Example 63

(4S,5S)-4-(hydroxymethyl)-N-(isoquinolin-4-ylmethyl)-5-(6-methoxy-4-(trifluoromethyl)-pyridin-2-yl)-2-oxooxazolidine-3-carboxamide

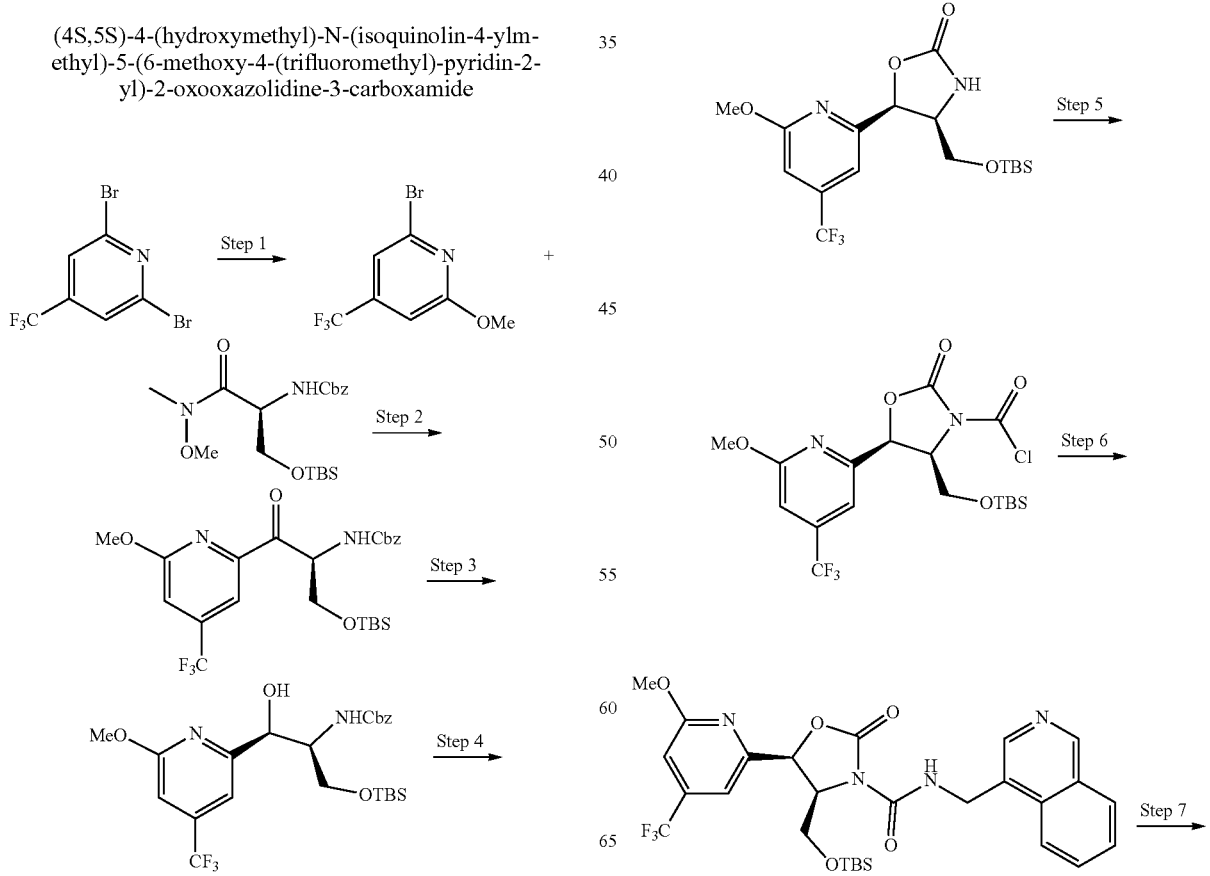

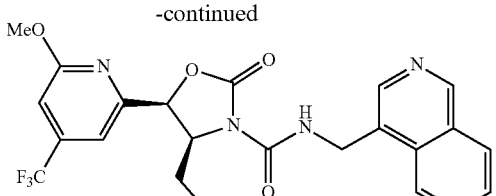

Example 63

Step 1: 2-bromo-6-methoxy-4-(trifluoromethyl)pyridine 2-bromo-6-methoxy-4-(trifluoromethyl)pyridine was prepared according to the procedure of Step 2 of Example 60.

Step 2: benzyl (S)-(3-((tert-butyldimethylsilyl)oxy)-1-(6-methoxy-4-(trifluoromethyl)pyridin-2-yl)-1-oxopropan-2-yl)carbamate To a solution of nBuLi (3.47 ml, 5.55 mmol) in THF (8 mL) was added a solution of 2-bromo-6-methoxy-4-(trifluoromethyl)pyridine (1.42 g, 5.55 mmol) in 3 mL THF at −78° C. The resulting mixture was stirred at −78° C. for 20 min, then was added a solution of (S)-benzyl (3,8,8,9,9-pentamethyl-4-oxo-2,7-dioxa-3-aza-8-siladecan-5-yl)carbamate (1.00 g, 2.52 mmol) in 4 mL THF. The reaction mixture was slowly warmed to 0° C. over 1 h.

The reaction was quenched with NH₄Cl, and brine, extracted with ethyl acetate, evaporated, and purified by flash chromatography (0% to 100% EtOAc in hexane) to provide the title compound.

Steps 3-7: (4S,5S)-4-(hydroxymethyl)-N-(isoquinolin-4-ylmethyl)-5-(6-methoxy-4-(trifluoro-methyl)-pyridin-2-yl)-2-oxooxazolidine-3-carboxamide Benzyl (S)-(3-((tert-butyldimethyl-silyl)oxy)-1-(6-methoxy-4-(trifluoromethyl)pyridin-2-yl)-1-oxopropan-2-yl)carbamate (the product of Step 2 of Example 63) was converted to the title compound following the procedure of Steps 4-8 of Example 50. LC-MS m/z [M+H]⁺ 477.17 (calc'd 477.14).

Example 65

(4S,5R)-5-(3,5-bis(trifluoromethyl)phenyl)-3-(3-(isoquinolin-4-yl)propanoyl)-4-methyloxazolidin-2-one

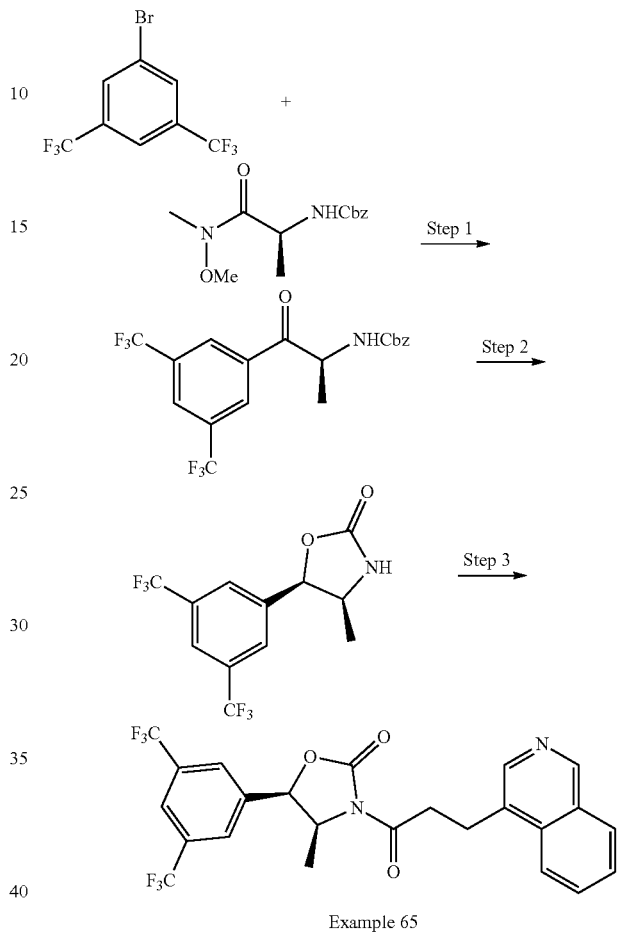

Example 65

(4S,5R)-5-(3,5-bis(trifluoromethyl)phenyl)-3-(3-(isoquinolin-4-yl)propanoyl)-4-methyloxazolidin-2-one 1,1'-Carbonyldiimidazole (0.79 g, 4.87 mmol) was added to a stirred mixture of 3-(isoquinolin-4-yl)propanoic acid (0.70 g, 3.48 mmol) in AcCN (60 mL) and the mixture was stirred at rt for 1 h. Then (4S,5R)-5-(3,5-bis(trifluoromethyl)phenyl)-4-methyloxazolidin-2-one (1.09 g, 3.48 mmol, synthesized according to Steps 1-2 in of Example 1) was added, followed by the addition of DBU (1.56 mL, 4.87 mmol). The resulting

TABLE 4

Example 64 was prepared according to the procedure of Example 63.

| Example Number | Structure | Name | Calc'd Mass M + H⁺ | Observed Mass M + H⁺ |
|---|---|---|---|---|
| 64 | ![structure] | (4S,5S)-4-(hydroxymethyl)-5-[6-methoxy-4-(trifluoromethyl)pyridin-2-yl]-N-(1,6-naphthyridin-8-ylmethyl)-2-oxo-1,3-oxazolidine-3-carboxamide | 478.39 | 478.30 | mixture was stirred at rt for 12 h. Then the reaction mixture was concentrated and purified by flash chromatography (000 to 60 EtOAc in hexane) to provide the title compound. LC-MS m/z [M+H]+ 497.22 (calc'd 497.40).

TABLE 5

The compounds in Examples 66-89* were prepared according to the procedure of Example 65.

| Example Number | Structure | Name | Calc'd Mass M + H+ | Observed Mass M + H+ |
|---|---|---|---|---|
| 66 | 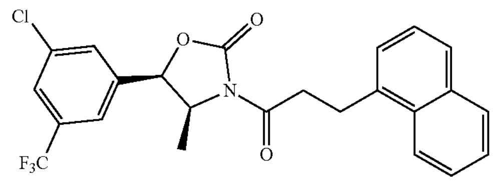 [SMILES: C[C@H]1[C@@H](c2cc(Cl)cc(C(F)(F)F)c2)OC(=O)N1C(=O)CCc1cccc2ccccc12] | (4S,5R)-5-[3-chloro-5-(trifluoromethyl)phenyl]-4-methyl-3-(3-naphthalen-1-ylpropanoyl)-1,3-oxazolidin-2-one | 462.11 | 462.23 |
| 67 | 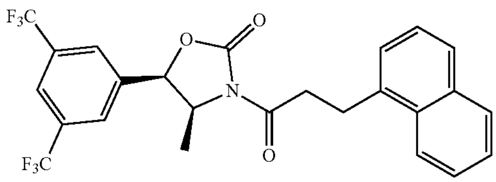 [SMILES: C[C@H]1[C@@H](c2cc(C(F)(F)F)cc(C(F)(F)F)c2)OC(=O)N1C(=O)CCc1cccc2ccccc12] | (4S,5R)-5-[3,5-bis(trifluoromethyl)phenyl]-4-methyl-3-(3-naphthalen-1-ylpropanoyl)-1,3-oxazolidin-2-one | 496.13 | 495.99 |
| 68 | 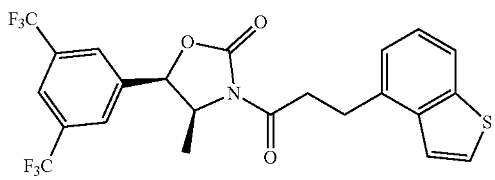 [SMILES: C[C@H]1[C@@H](c2cc(C(F)(F)F)cc(C(F)(F)F)c2)OC(=O)N1C(=O)CCc1cccc2sccc12] | (4S,5R)-3-[3-(1-benzothiophen-4-yl)propanoyl]-5-[3,5-bis(trifluoromethyl)phenyl]-4-methyl-1,3-oxazolidin-2-one | 502.09 | 501.93 |
| 69 | 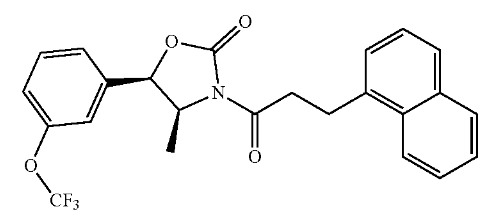 [SMILES: C[C@H]1[C@@H](c2cccc(OC(F)(F)F)c2)OC(=O)N1C(=O)CCc1cccc2ccccc12] | (4S,5R)-4-methyl-3-(3-naphthalen-1-ylpropanoyl)-5-[3-(trifluoromethoxy)phenyl]-1,3-oxazolidin-2-one | 444.14 | 444.34 |
| 70 | 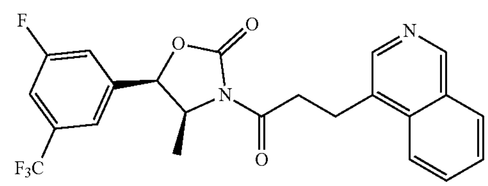 [SMILES: C[C@H]1[C@@H](c2cc(F)cc(C(F)(F)F)c2)OC(=O)N1C(=O)CCc1cncc2ccccc12] | (4S,5R)-5-[3-fluoro-5-(trifluoromethyl)phenyl]-3-(3-isoquinolin-4-ylpropanoyl)-4-methyl-1,3-oxazolidin-2-one | 447.39 | 447.02 |
| 71 | 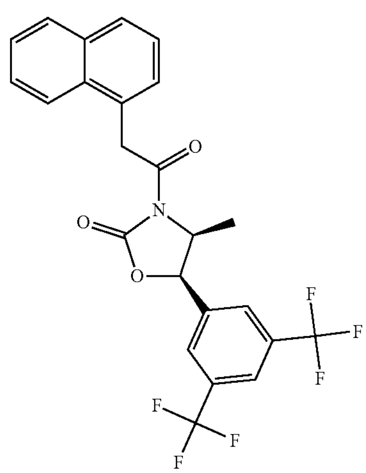 [SMILES: C[C@H]1[C@@H](c2cc(C(F)(F)F)cc(C(F)(F)F)c2)OC(=O)N1C(=O)Cc1cccc2ccccc12] | (4S,5R)-5-[3,5-bis(trifluoromethyl)phenyl]-4-methyl-3-(naphthalen-1-ylacetyl)-1,3-oxazolidin-2-one | 482.12 | 482.28 |

TABLE 5-continued

The compounds in Examples 66-89* were prepared according to the procedure of Example 65.

| Example Number | Structure | Name | Calc'd Mass M + H+ | Observed Mass M + H+ |
|---|---|---|---|---|
| 72 | 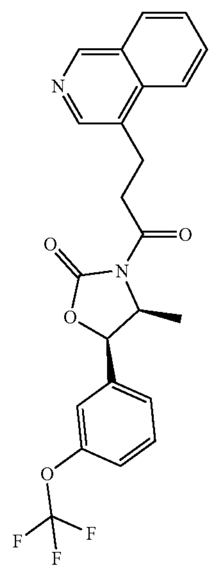 [SMILES: C[C@H]1[C@@H](c2cccc(OC(F)(F)F)c2)OC(=O)N1C(=O)CCc1cncc2ccccc12] | (4S,5R)-3-(3-isoquinolin-4-ylpropanoyl)-4-methyl-5-[3-(trifluoromethoxy)phenyl]-1,3-oxazolidin-2-one | 445.14 | 444.90 |
| 73 | 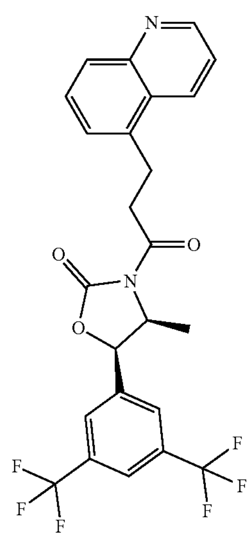 [SMILES: C[C@H]1[C@@H](c2cc(C(F)(F)F)cc(C(F)(F)F)c2)OC(=O)N1C(=O)CCc1cccc2ncccc12] | (4S,5R)-5-[3,5-bis(trifluoromethyl)phenyl]-4-methyl-3-(3-quinolin-5-ylpropanoyl)-1,3-oxazolidin-2-one | 497.13 | 497.16 |
| 74 | 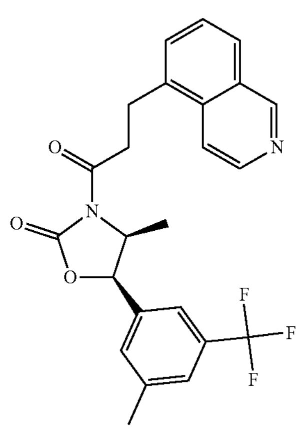 [SMILES: Cc1cc([C@H]2OC(=O)N(C(=O)CCc3cccc4cnccc34)[C@H]2C)cc(C(F)(F)F)c1] | (4S,5R)-3-(3-isoquinolin-5-ylpropanoyl)-4-methyl-5-[3-methyl-5-(trifluoromethyl)phenyl]-1,3-oxazolidin-2-one | 443.43 | 443.27 |

TABLE 5-continued

The compounds in Examples 66-89* were prepared according to the procedure of Example 65.

| Example Number | Structure | Name | Calc'd Mass M + H⁺ | Observed Mass M + H⁺ |
|---|---|---|---|---|
| 75 | 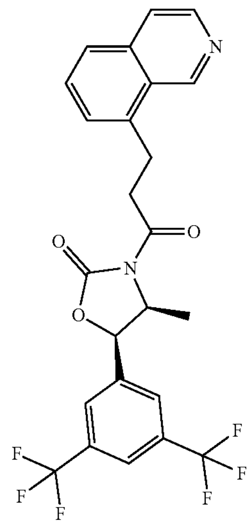 [SMILES: C[C@H]1[C@@H](c2cc(C(F)(F)F)cc(C(F)(F)F)c2)OC(=O)N1C(=O)CCc1cccc2ccncc12] | (4S,5R)-5-[3,5-bis(trifluoromethyl)phenyl]-3-(3-isoquinolin-8-ylpropanoyl)-4-methyl-1,3-oxazolidin-2-one | 497.13 | 497.40 |
| 76 | 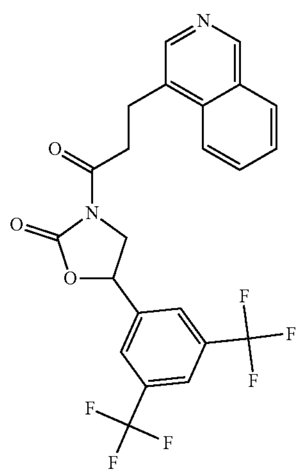 [SMILES: O=C(CCc1cncc2ccccc12)N1CC(c2cc(C(F)(F)F)cc(C(F)(F)F)c2)OC1=O] | 5-[3,5-bis(trifluoromethyl)phenyl]-3-(3-isoquinolin-4-ylpropanoyl)-1,3-oxazolidin-2-one | 483.38 | 483.26 |
| 77 | 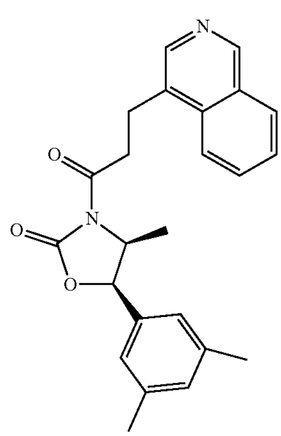 [SMILES: Cc1cc(C)cc([C@H]2OC(=O)N(C(=O)CCc3cncc4ccccc34)[C@H]2C)c1] | (4S,5R)-5-(3,5-dimethylphenyl)-3-(3-isoquinolin-4-ylpropanoyl)-4-methyl-1,3-oxazolidin-2-one | 389.46 | 389.19 |

TABLE 5-continued

The compounds in Examples 66-89* were prepared according to the procedure of Example 65.

| Example Number | Structure | Name | Calc'd Mass M + H+ | Observed Mass M + H+ |
|---|---|---|---|---|
| 78 | 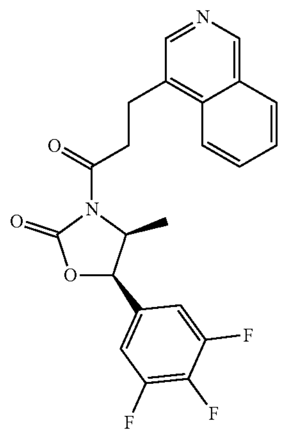 [SMILES: C[C@H]1[C@@H](c2cc(F)c(F)c(F)c2)OC(=O)N1C(=O)CCc1cncc2ccccc12] | (4S,5R)-3-(3-isoquinolin-4-ylpropanoyl)-4-methyl-5-(3,4,5-trifluorophenyl)-1,3-oxazolidin-2-one | 415.38 | 415.32 |
| 79 | 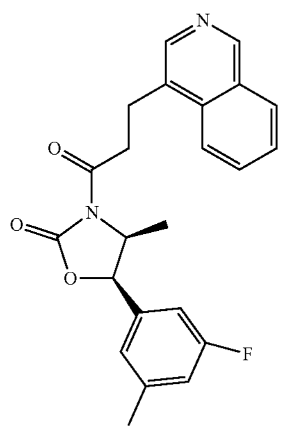 | (4S,5R)-5-(3-fluoro-5-methylphenyl)-3-(3-isoquinolin-4-ylpropanoyl)-4-methyl-1,3-oxazolidin-2-one | 393.42 | 393.01 |
| 80 | 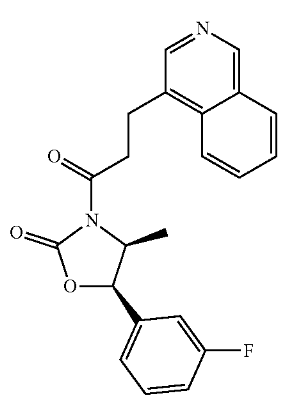 [SMILES: C[C@H]1[C@@H](c2cccc(F)c2)OC(=O)N1C(=O)CCc1cncc2ccccc12] | (4S,5R)-5-(3-fluorophenyl)-3-(3-isoquinolin-4-ylpropanoyl)-4-methyl-1,3-oxazolidin-2-one | 379.40 | 379.18 |

TABLE 5-continued

The compounds in Examples 66-89* were prepared according to the procedure of Example 65.

| Example Number | Structure | Name | Calc'd Mass M + H$^+$ | Observed Mass M + H$^+$ |
|---|---|---|---|---|
| 81 | 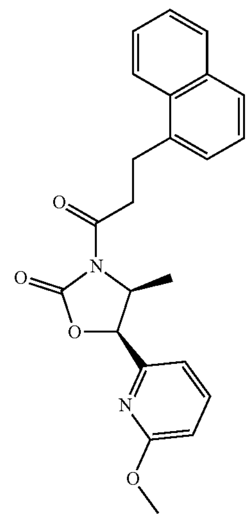 [SMILES: COc1cccc([C@H]2OC(=O)N(C(=O)CCc3cccc4ccccc34)[C@H]2C)n1] | (4S,5S)-5-(6-methoxypyridin-2-yl)-4-methyl-3-(3-naphthalen-1-ylpropanoyl)-1,3-oxazolidin-2-one | 391.17 | 391.34 |
| 82 | 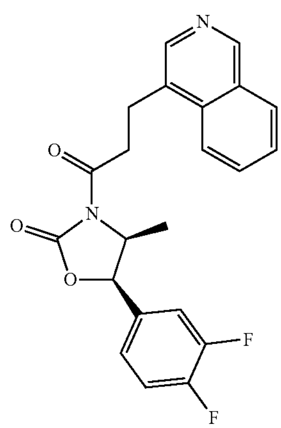 [SMILES: C[C@H]1[C@@H](c2ccc(F)c(F)c2)OC(=O)N1C(=O)CCc1cncc2ccccc12] | (4S,5R)-5-(3,4-difluorophenyl)-3-(3-isoquinolin-4-ylpropanoyl)-4-methyl-1,3-oxazolidin-2-one | 397.39 | 397.20 |
| 83 | 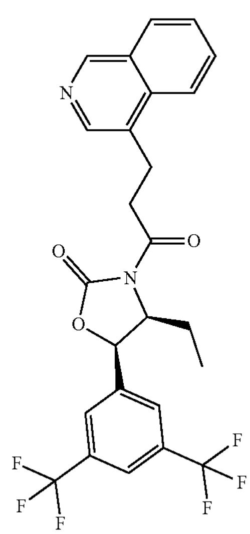 [SMILES: CC[C@H]1[C@@H](c2cc(C(F)(F)F)cc(C(F)(F)F)c2)OC(=O)N1C(=O)CCc1cncc2ccccc12] | (4S,5R)-5-[3,5-bis(trifluoromethyl)phenyl]-4-ethyl-3-(3-isoquinolin-4-ylpropanoyl)-1,3-oxazolidin-2-one | 511.43 | 511.18 |

TABLE 5-continued

The compounds in Examples 66-89* were prepared according to the procedure of Example 65.

| Example Number | Structure | Name | Calc'd Mass M + H⁺ | Observed Mass M + H⁺ |
|---|---|---|---|---|
| 84 | 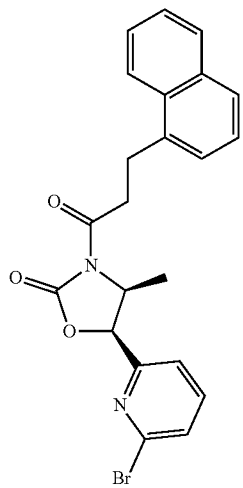 [SMILES: C[C@H]1[C@@H](c2cccc(Br)n2)OC(=O)N1C(=O)CCc1cccc2ccccc12] | (4S,5S)-5-(6-bromopyridin-2-yl)-4-methyl-3-(3-naphthalen-1-ylpropanoyl)-1,3-oxazolidin-2-one | 439.07; 441.07 | 438.80; 441.08 |
| 85 | 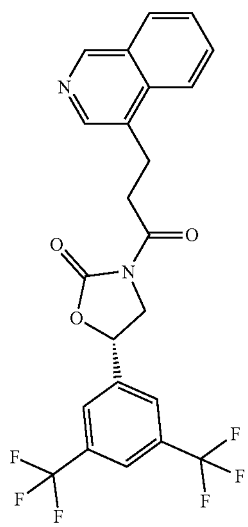 [SMILES: O=C(CCc1cncc2ccccc12)N1C[C@H](c2cc(C(F)(F)F)cc(C(F)(F)F)c2)OC1=O] | (5S)-5-[3,5-bis(trifluoromethyl)phenyl]-3-(3-isoquinolin-4-ylpropanoyl)-1,3-oxazolidin-2-one | 483.11 | 483.17 |
| 86 | 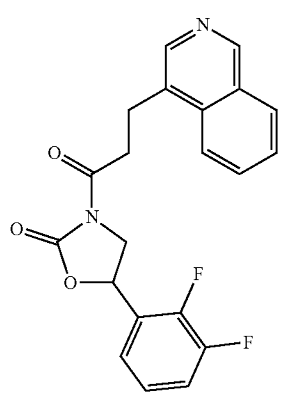 [SMILES: O=C(CCc1cncc2ccccc12)N1CC(c2cccc(F)c2F)OC1=O] | 5-(2,3-difluorophenyl)-3-(3-isoquinolin-4-ylpropanoyl)-1,3-oxazolidin-2-one | 383.36 | 383.24 |

TABLE 5-continued
The compounds in Examples 66-89* were prepared according to the procedure of Example 65.
| Example Number | Structure | Name | Calc'd Mass M + H⁺ | Observed Mass M + H⁺ |
|---|---|---|---|---|
| 87 | 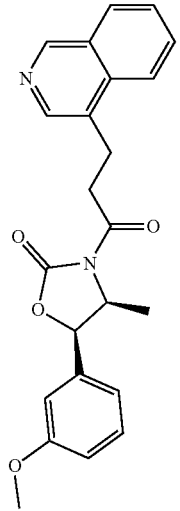 [SMILES: COc1cccc([C@H]2OC(=O)N(C(=O)CCc3cncc4ccccc34)[C@H]2C)c1] | (4S,5R)-3-(3-isoquinolin-4-ylpropanoyl)-5-(3-methoxyphenyl)-4-methyl-1,3-oxazolidin-2-one | 391.17 | 391.43 |
| 88 | 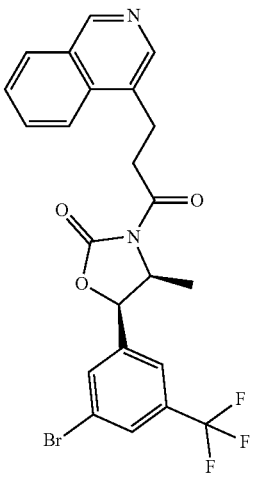 [SMILES: C[C@H]1[C@@H](c2cc(Br)cc(C(F)(F)F)c2)OC(=O)N1C(=O)CCc1cncc2ccccc12] | (4S,5R)-5-[3-bromo-5-(trifluoromethyl)phenyl]-3-(3-isoquinolin-4-ylpropanoyl)-4-methyl-1,3-oxazolidin-2-one | 507.05; 509.05 | 507.61; 508.90 |

TABLE 5-continued

The compounds in Examples 66-89* were prepared according to the procedure of Example 65.

| Example Number | Structure | Name | Calc'd Mass M + H+ | Observed Mass M + H+ |
|---|---|---|---|---|
| 89 | 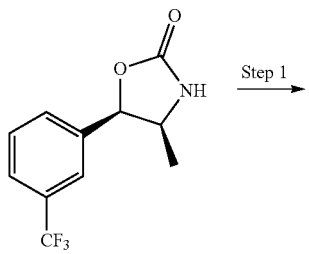 | (4S,5S)-3-(3-(isoquinolin-4-yl)propanoyl)-4-methyl-5-(4-(trifluoromethyl)pyridin-2-yl)oxazolidin-2-one | 430.14 | 430.16 |

*The compounds in Examples 65-89 were purified by either silica gel column chromatography or by mass triggered HPLC using the following conditions: column: Waters Sunfire C18, 5u, 19 × 100 mm; solvent: gradient range: 10-15% initial to 70-98% final MeCN (either 0.1% formic acid or TFA) in water (0.1% formic acid or TFA) 50 mL/min 8 min run time.

Example 90

(4S,5R)-3-(2-(2,3-dimethylphenoxy)acetyl)-4-methyl-5-(3-(trifluoromethyl)-phenyl)oxazolidin-2-one

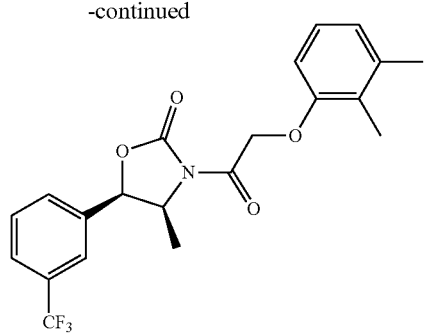

Example 90

Step 1: (4S,5R)-3-(2-bromoacetyl)-4-methyl-5-(3-(trifluoromethyl)phenyl)oxazolidin-2-one To a stirred solution of (4S,5R)-4-methyl-5-(3-(trifluoromethyl)phenyl)oxazolidin-2-one (1.0 g, 4.08 mmol) in THF (20 mL) was added n-butyllithium in hexane (1.79 mL, 4.49 mmol) dropwise at 0° C. under Ar atmosphere. After stirring for 15 min, 2-bromoacetyl bromide (0.46 mL, 5.30 mmol) was added dropwise, and the mixture was stirred at the same temperature for 3 h. The resulting mixture was quenched with saturated aqueous NaHCO₃ and extracted with ethyl acetate. The combined organic layers were dried over Na₂SO₄ and evaporated. The residue was purified by flash chromatography (0% to 30% EtOAc in hexane) to give the title compound.

Step 2: (4S,5R)-3-(2-(2,3-dimethylphenoxy)acetyl)-4-methyl-5-(3-(trifluoromethyl)phenyl)-oxazolidin-2-one To a solution of (4S,5S)-3-(2-bromoacetyl)-4-methyl-5-(3-(trifluoro-methyl)phenyl)oxazolidin-2-one (50.0 mg, 0.14 mmol) in DMF (1 mL) was added DIPEA (36 μL, 0.20 mmol) and 2,3 dimethylphenol (16.0 mg, 0.14 mmol). The resulting mixture was heated at 60° C. for 12 h. The reaction mixture was allowed to cool to rt and added directly onto Gilson reverse phase, eluting with 40% to 100% MeCN/

H₂O/0.1% TFA to yield the title compound. LC-MS m/z [M+H]⁺ 408.11 (calc'd 408.14).

TABLE 6

Example 91 was prepared according to the procedure of Example 90.

| Example Number | Structure | Name | Calc'd Mass M + H⁺ | Observed Mass M + H⁺ |
|---|---|---|---|---|
| 91 | 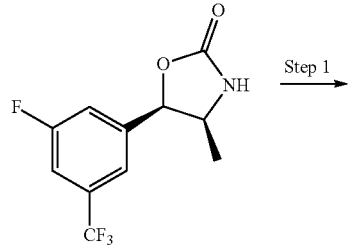 | (4S,5R)-5-[3,5-bis(trifluoromethyl)phenyl]-4-methyl-3-[(naphthalen-1-yloxy)acetyl]-1,3-oxazolidin-2-one | 498.11 | 498.98 |

Example 92

(4S,5R)-5-(3-fluoro-5-(trifluoromethyl)phenyl)-4-methyl-3-(3-(6-methyl-2,3-dihydro-4H-pyrido[3,2-b][1,4]oxazin-4-yl)propanoyl)oxazolidin-2-one

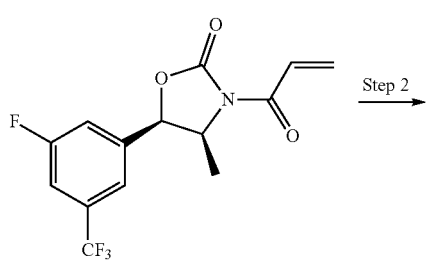

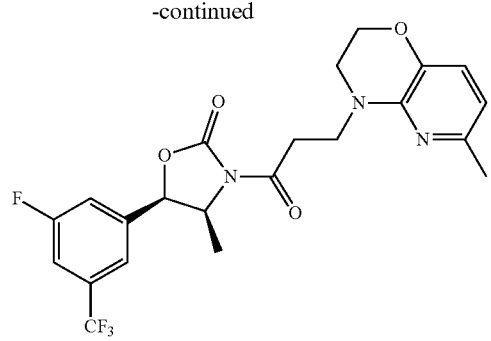

Example 92

Step 1: (4S,5R)-3-acryloyl-5-(3-fluoro-5-(trifluoromethyl)phenyl)-4-methyloxazolidin-2-one To a solution of (4S,5R)-5-(3-fluoro-5-(trifluoromethyl)phenyl)-4-methyl-oxazolidin-2-one (0.5 g, 1.90 mmol, synthesized according to the procedure of steps 1-2 of Example 1) in THF (10 mL) was added lithium chloride (0.10 g, 2.38 mmol) followed by triethylamine (0.33 mL, 2.375 mmol) at 0° C. A solution of acrylic anhydride (0.30 g, 2.38 mmol) in 1 mL THF was added into the above mixture. The mixture was slowly warmed to rt and stirred at rt for 2 h. LCMS indicated that the reaction was completed. The reaction mixture was concentrated to dryness and added 10 mL 1 N HCl. The resulting solution was extracted with DCM (20 mL), then the DCM layer was washed with 1:1 water and saturated NaHCO₃(10 mL). The DCM layer was evaporated and purified by flash chromatography (0% to 15% EtOAc in hexane) to yield the title compound.

Step 2: (4S,5R)-5-(3-fluoro-5-(trifluoromethyl)phenyl)-4-methyl-3-(3-(6-methyl-2,3-dihydro-4H-pyrido[3,2-b][1,4]oxazin-4-yl)propanoyl)oxazolidin-2-one (4S,5R)-3-acryloyl-5-(3-fluoro-5-(trifluoromethyl)phenyl)-4-methyloxazolidin-2-one (63.0 mg, 0.14 mmol) was dissolved in DMSO (2 mL) in a microwave tube and 6-methyl-3,4-dihydro-2H-pyrido[3,2-b][1,4]oxazine (450.0 mg, 3.00 mmol) was added. The reaction vessel was capped, purged with nitrogen and stirred at 50° C. overnight. The mixture was loaded directly onto a silica gel column for flash chromatography (0% to 40% EtOAc in hexane). The crude product was further purified on Gilson reverse phase HPLC (20% to 100% MeCN/H$_2$O/TFA 0.1%) to afford the title compound. LC-MS m/z [M+H]$^+$ 468.64 (calc'd 468.15).

Example 93

(5R,6S)-6-(3,5-bis(trifluoromethyl)phenyl)-N-(isoquinolin-4-ylmethyl)-5-methyl-2-oxo-1,3-oxazinane-3-carboxamide

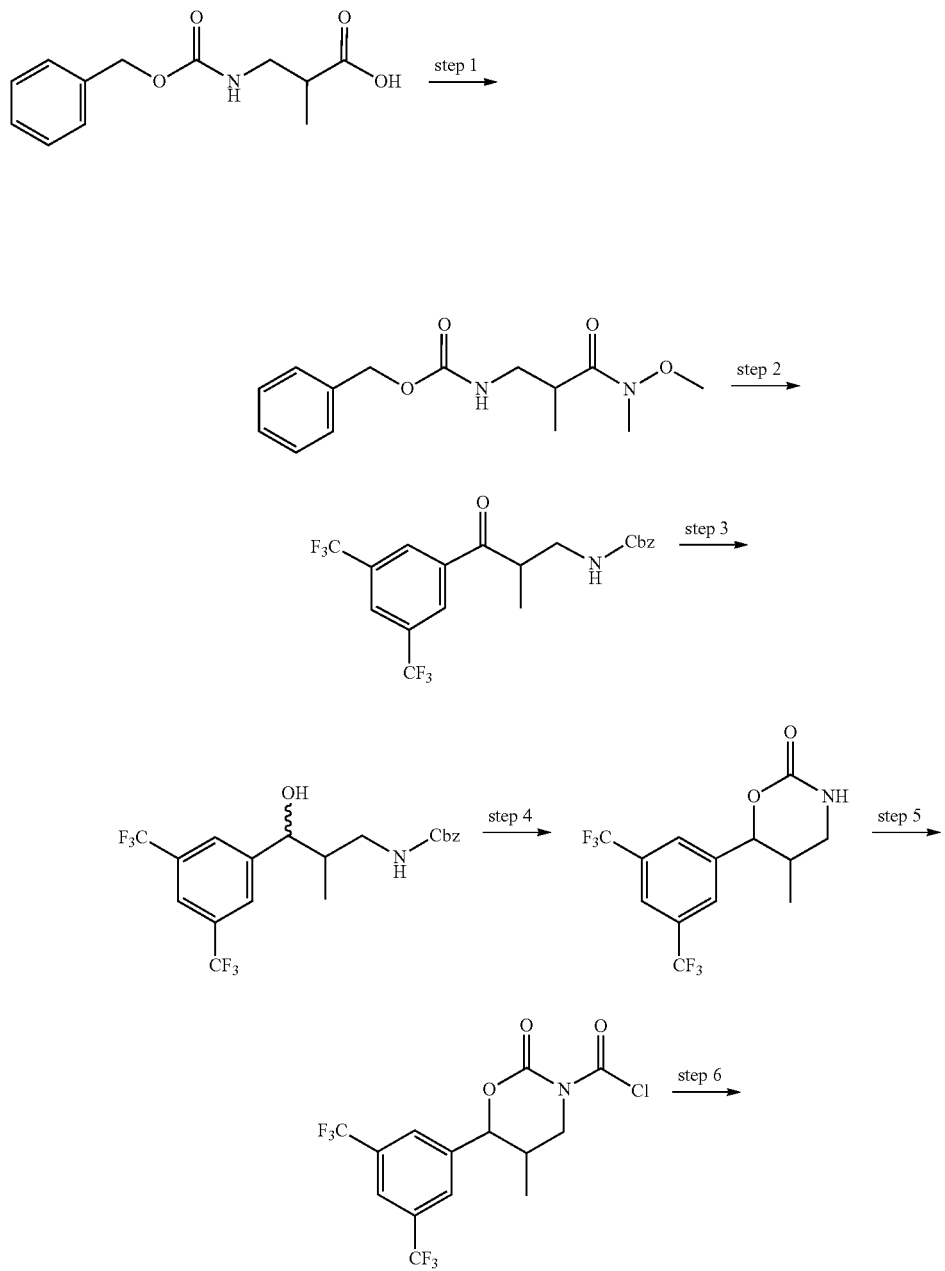

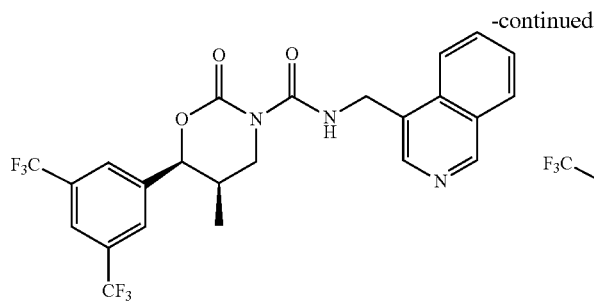

93

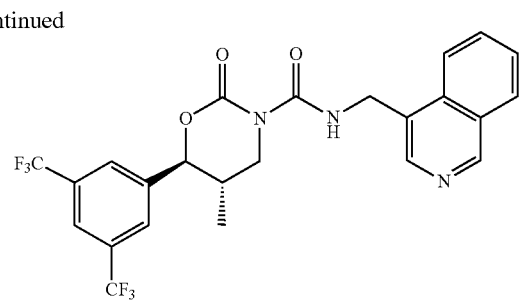

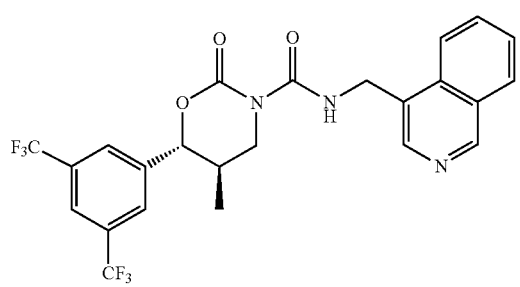

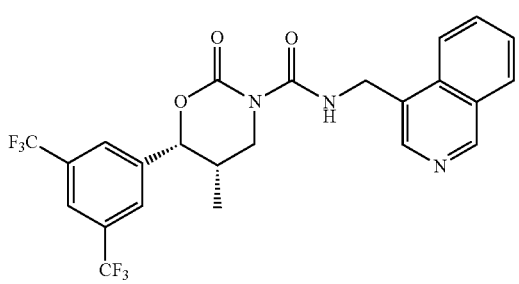

Example 93

Step 1: benzyl (3-(methoxy(methyl)amino)-2-methyl-3-oxopropyl)carbamate The title compound was prepared according to the procedure of Step 1 of Example 50.

Step 2: benzyl (3-(3,5-bis(trifluoromethyl)phenyl)-2-methyl-3-oxopropyl)carbamate The title compound was prepared according to the procedure of Step 1 of Example 1.

Step 3: benzyl (3-(3,5-bis(trifluoromethyl)phenyl)-3-hydroxy-2-methylpropyl)carbamate To a solution of benzyl (3-(3,5-bis(trifluoromethyl)phenyl)-2-methyl-3-oxopropyl) carbamate (622.0 mg, 1.44 mmol) in ethanol (15 mL) was added lithium tri-tert-butoxyaluminum hydride (1.0 M in THF, 7.18 mL, 7.18 mmol) at −78° C. The resulting solution was stirred for 1 h, then quenched with 1 M HCl (25 mL), diluted with water, and extracted with ethyl acetate. The combined organic layers were washed with brine, dried with MgSO$_4$, filtered, and the solvent was evaporated under reduced pressure. The resulting residue was taken directly to the next step without further purification.

Step 4: 6-(3,5-bis(trifluoromethyl)phenyl)-5-methyl-1,3-oxazinan-2-one To a solution of benzyl (3-(3,5-bis(trifluoromethyl)phenyl)-3-hydroxy-2-methylpropyl)carbamate (625.0 mg, 1.44 mmol) in THF (5 mL) was added NaH (68.9 mg, 1.72 mmol) at −25° C. The resulting mixture was slowly warmed to rt over 12 h, and then heated at 38° C. for 12 h. Then the reaction mixture was cooled to rt, and quenched with 1 N HCl, and extracted with ethyl acetate. The combined organic fractions were washed with brine, dried with MgSO$_4$, filtered, and the solvent was evaporated under reduced pressure. The resulting residue was purified by flash chromatography (0% to 75% EtOAc in hexane) to provide the title compound as a mixture of 7:3 (cis:trans) diastereomers. LC-MS m/z [M+H]$^+$ 328.39 (calc'd 328.07).

Step 5: 6-(3,5-bis(trifluoromethyl)phenyl)-5-methyl-2-oxo-1,3-oxazinane-3-carbonyl chloride The title compound was prepared according to the procedure of Step 6 of Example 50.

Step 6: 6-(3,5-bis(trifluoromethyl)phenyl)-N-(isoquinolin-4-ylmethyl)-5-methyl-2-oxo-1,3-oxazinane-3-carboxamide 6-(3,5-bis(trifluoromethyl)phenyl)-5-methyl-2-oxo-1,3-oxazinane-3-carbonyl chloride (119.0 mg, 0.30 mmol) was added to a stirred mixture of isoquinolin-4-ylmethanamine (97.0 mg, 0.61 mmol) in dichloromethane and water (2 drops) at 0° C. The resulting mixture was slowly warmed to rt over 12 h and concentrated in vacuo. The resulting residue was separated into cis and trans diastereomers using flash chromatography on silica gel (0% to 100% EtOAc in hexane). The racemic cis diastereomer was further submitted for SFC separation (method: isocratic, 25% of EtOH in CO$_2$; back pressure 120 bar, 40° C.; flow rate: 3 ml/min; column: OJ-H, 4.6×250 mm, 5 μm) to afford the (5R,6S) enantiomer (R$_t$=2.49 min) and the (5S,6R) enantiomer (R$_t$=2.18 min). The two enantiomers of the trans product were obtained using the same conditions.

TABLE 7

Example 94 was prepared according to the procedure of Example 93.

| Example Number | Structure | Name | Calc'd Mass M + H⁺ | Observed Mass M + H⁺ |
|---|---|---|---|---|
| 94 | 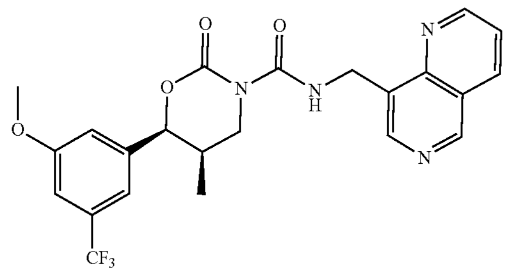 [SMILES: COc1cc([C@H]2OC(=O)N(C(=O)NCc3cncc4cccnc34)C[C@H]2C)cc(C(F)(F)F)c1] | (5R,6S)-6-[3-methoxy-5-(trifluoromethyl)phenyl]-5-methyl-N-(1,6-naphthyridin-8-ylmethyl)-2-oxo-1,3-oxazinane-3-carboxamide | 475.15 | 475.29 |

Example 95

(5R,6S)-6-(3,5-bis(trifluoromethyl)phenyl)-N-(isoquinolin-4-ylmethyl)-5-methyl-2-oxo-1,3-oxazinane-3-carboxamide

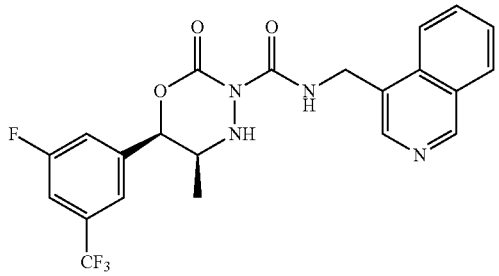 [SMILES: C[C@@H]1NN(C(=O)NCc2cncc3ccccc23)C(=O)O[C@@H]1c1cc(F)cc(C(F)(F)F)c1]

Step 1: benzyl ((1R,2S)-1-(3-fluoro-5-(trifluoromethyl)phenyl)-1-hydroxypropan-2-yl)carbamate To a solution of (S)-benzyl (1-(3-fluoro-5-(trifluoromethyl)phenyl)-1-oxopropan-2-yl)carbamate (3.36 g, 9.10 mmol) in the mixture of toluene (9 mL) and 2-propanol (6 mL) was added aluminum isopropoxide (0.37 g, 1.82 mmol). The reaction mixture was heated at 50° C. for 6 h, then diluted with water, and extracted with EtOAc twice. The combined organic layers were dried over Na₂SO₄, and concentrated to give the title compound. LC-MS m/z [M+H]⁺ 372.26 (calc'd 372.11).

Step 2: (1R,2S)-2-amino-1-(3-fluoro-5-(trifluoromethyl)phenyl)propan-1-ol To a solution of benzyl ((1R,2S)-1-(3-fluoro-5-(trifluoromethyl)phenyl)-1-hydroxypropan-2-yl)carbamate (3.35 g, 9.02 mmol) in MeOH (80 mL) was added 10% Pd/C (0.77 g, 0.72 mmol). The resulting mixture was subjected to hydrogenation at rt via H₂ balloon for 3 h. Then the mixture was filtered through Celite™ under a N₂ atmosphere, and the filtrate was concentrated to give the title compound. LC-MS m/z [M+H]⁺ 238.16 (calc'd 238.11).

Step 3: (1R,2S)-2-(allylamino)-1-(3-fluoro-5-(trifluoromethyl)phenyl)propan-1-ol To a solution of (1R,2S)-2-amino-1-(3-fluoro-5-(trifluoromethyl)phenyl)propan-1-ol (2.13 g, 8.98 mmol) and DBU (1.35 mL, 8.98 mmol) was added dropwise allyl bromide (0.78 mL, 8.98 mmol). The resulting solution was stirred at rt over the weekend, then concentrated. The resulting residue was purified by flash chromatography (0% to 15% MeOH in DCM) to give the title compound. LC-MS m/z [M+H]⁺ 278.17 (calc'd 278.11).

Step 4: N-allyl-N-((1R,2S)-1-(3-fluoro-5-(trifluoromethyl)phenyl)-1-hydroxypropan-2-yl)nitrous amide To the mixture of (1R,2S)-2-(allylamino)-1-(3-fluoro-5-(trifluoromethyl)phenyl)propan-1-ol (1.68 g, 6.06 mmol) in THF (30 mL) was added HCl (3.32 mL, 2.74 M, 9.09 mmol). The mixture was cooled to 0° C., and sodium nitrite (0.54 g, 7.88 mmol) was added. The resulting mixture was allowed to warm from 0° C. to rt overnight. Then the mixture was basified by the addition of saturated NaHCO₃, and extracted with EtOAc three times. The combined organic layers were washed with brine twice, dried over Na₂SO₄, and concentrated to give the title compound. LC-MS m/z [M+H+MeCN]⁺ 348.25 (calc'd 348.13).

Step 5: (1R,2S)-2-(1-allylhydrazinyl)-1-(3-fluoro-5-(trifluoromethyl)phenyl)propan-1-ol To THF (20 mL) was added LiAlH₄ (2M in THF, 6.14 mL, 12.28 mmol) at reflux. Then a solution of N-allyl-N-((1R,2S)-1-(3-fluoro-5-(trifluoromethyl)phenyl)-1-hydroxypropan-2-yl)nitrous amide (1.88 g, 6.14 mmol) in THF (20 mL) was added dropwise while keeping the solution at reflux for 10 min. The reaction was heated at reflux for 2 h, then cooled to rt and quenched by the dropwise addition of 6 N NaOH. Then saturated sodium potassium tartrate solution (100 mL) was added. The resulting mixture was stirred at rt for 2 h, and then extracted with EtOAc three times. The combined organic layers were dried over Na₂SO₄, and concentrated to give the title compound. LC-MS m/z [M+H]⁺ 293.21 (calc'd 293.12).

Step 6: (5S,6R)-4-allyl-6-(3-fluoro-5-(trifluoromethyl)phenyl)-5-methyl-1,3,4-oxadiazinan-2-one A solution of diethyl carbonate (728.0 mg, 6.16 mmol) and (1R,2S)-2-(1-allylhydrazinyl)-1-(3-fluoro-5-(trifluoromethyl)phenyl)propan-1-ol (1.80 g, 6.16 mmol) in hexane (100 mL) was heated at reflux. To the refluxing solution was added NaH (246.0 mg, 6.16 mmol) and the resulting reaction mixture was heated at reflux for 4 h. After cooling to rt, the mixture was concentrated and the resulting residue was dissolved in EtOAc, then washed with 1 N HCl, saturated NaHCO₃, and brine, then dried over Na₂SO₄ and concentrated. The resulting residue was purified by flash chromatography (silica gel column), 0% to 100% EtOAc in hexane) to give the title compound. LC-MS m/z [M+H]⁺ 319.23 (calc'd 319.11).

Step 7: (5S,6R)-4-allyl-6-(3-fluoro-5-(trifluoromethyl)phenyl)-5-methyl-2-oxo-1,3,4-oxadiazinane-3-carbonyl chloride To the solution of (5S,6R)-4-allyl-6-(3-fluoromethyl)phenyl)-5-methyl-1,3,4-oxadiazinan-2-one (16.0 mg, 0.05 mmol) in THF (4 mL) at −78° C. was added n-butyllithium (35 μL, 0.06 mmol). The resulting solution was stirred at −78° C. for 5 min before the addition of diphosgene (7 μL, 0.06 mmol). The reaction was stirred at −78° C. for 30 min, then warmed to rt and concentrated to give the title compound. LC-MS m/z [M+H−Cl+MeOH]⁺ 377.25 (calc'd 377.10).

Step 8: (5S,6R)-4-allyl-6-(3-fluoro-5-(trifluoromethyl) phenyl)-N-(isoquinolin-4-ylmethyl)-5-methyl-2-oxo-1,3,4-oxadiazinane-3-carboxamide To a solution of (5S,6R)-4-allyl-6-(3-fluoro-5-(trifluoromethyl)phenyl)-5-methyl-2-oxo-1,3,4-oxadiazinane-3-carbonyl chloride (19.0 mg, 0.05 mmol) in DCM (3 mL) was added isoquinolin-4-ylmethanamine dihydrochloride (11.6 mg, 0.05 mmol) and TEA (0.042 mL, 0.30 mmol). The resulting mixture was stirred at rt for 10 min, and then concentrated in vacuo. The resulting residue was purified by reverse phase HPLC (MeCN in 0.05% TFA)/water (0.05% TFA)) to give the title compound. LC-MS m/z [M+H]+ 503.34 (calc'd 503.16).

Step 9: (5R,6S)-6-(3,5-bis(trifluoromethyl)phenyl)-N-(isoquinolin-4-ylmethyl)-5-methyl-2-oxo-1,3-oxazinane-3-carboxamide The solution of (5S,6R)-4-allyl-6-(3-fluoro-5-(trifluoromethyl)-phenyl)-N-(isoquinolin-4-ylmethyl)-5-methyl-2-oxo-1,3,4-oxadiazinane-3-carboxamide (230.0 mg, 0.46 mmol), and 1,3-dimethylbarbituric acid (214.0 mg, 1.37 mmol) in DCM (10 mL) was bubbled with $N_2$ for 15 min. Then tetrakis(triphenylphosphine)palladium(0) (26.4 mg, 0.02 mmol) was added. The resulting mixture was heated at 35° C. for three days, then partitioned between saturated $NaHCO_3$ and DCM. The aqueous layer was separated and extracted with DCM (3×). The combined organic layers were dried over $Na_2SO_4$, and concentrated in vacuo. The resulting residue was purified by flash chromatography (0% to 100% EtOAc in hexane) to give a residue, which was further purified by reverse phase HPLC (MeCN (0.05% TFA)/water(0.05% TFA)) to give the title compound. LC-MS m/z [M+H]⁺ 463.29 (calc'd 463.13).

Example 96

(4S,5R)—N-(isoquinolin-4-ylmethyl)-5-(4-methoxy-6-(trifluoromethyl)pyrimidin-2-yl)-4-methyl-2-oxooxazolidine-3-carboxamide

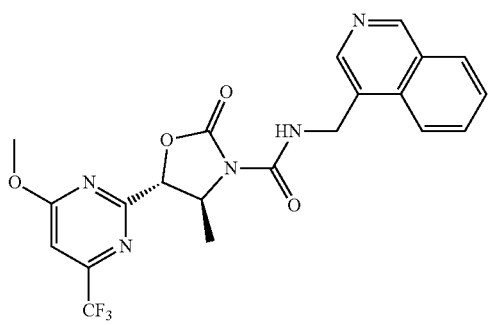 [SMILES: COc1cc(C(F)(F)F)nc([C@@H]2OC(=O)N(C(=O)NCc3cncc4ccccc34)[C@H]2C)n1]

Step 1: (4S,5R)-3-(4-methoxybenzyl)-4-methyl-5-vinyloxazolidin-2-one To a solution of (4S,5R)-4-methyl-5-vinyl oxazolidin-2-one (4.08 g, 32.1 mmol) in DMF (60 mL) at 0° C. was added NaH (1.54 g, 38.5 mmol). The resulting mixture was stirred at 0° C. for 30 min, then DMF (15 mL) was added, followed by the addition of 4-methoxybenzyl chloride (4.6 mL, 33.7 mmol). The resulting mixture was heated at 90° C. for 2 h. The resulting solid was filtered off and the filtrate was quenched with water, and concentrated. The resulting residue was dissolved in EtOAc (300 mL) and washed with water (3×), then dried over $Na_2SO_4$, and concentrated. The resulting residue was purified by flash chromatography (0% to 100% EtOAc in hexane) to give the title compound. LC-MS m/z [M+H]⁺ 248.11 (calc'd 248.12).

Step 2: (4S,5S)-3-(4-methoxybenzyl)-4-methyl-2-oxooxazolidine-5-carbaldehyde To a solution of (4 S, 5R)-3-(4-methoxybenzyl)-4-methyl-5-vinyloxazolidin-2-one (7.54 g, 30.5 mmol) in dioxane (200 mL) and water (100 ml) was added sodium periodate (26.10 g, 122.0 mmol) and osmium tetroxide (2.5% in tert-butanol, 12.40 g, 1.2 mmol). The resulting mixture was stirred at rt over the weekend. After filtration, the filtrate was concentrated and the resulting residue was partitioned between water and DCM. The aqueous phase was separated and extracted with 30% IPA/DCM three times. The combined organic layers were dried over $Na_2SO_4$, and concentrated to give the title compound. LC-MS m/z [M+H+MeOH]⁺ 282.14 (calc'd 282.13).

Step 3: (4S,5S)-3-(4-methoxybenzyl)-4-methyl-2-oxooxazolidine-5-carboxylic acid To a solution of (4S,5S)-3-(4-methoxybenzyl)-4-methyl-2-oxooxazolidine-5-carbaldehyde (7.60 g, 30.5 mmol) in tert-Butanol (40 mL) was added potassium dihydrogen phosphate (4.98 g, 36.6 mmol) in water (40 mL), followed by 2-methyl-2-butene (32.3 mL, 305.0 mmol), and sodium chlorite (5.52 g, 61.0 mmol). The reaction mixture was stirred from 0° C. to rt overnight, then acidified to pH 2 by 1 N HCl. The resulting mixture was extracted with EtOAc, followed by extraction with 30% IPA/DCM (3×150 mL). The combined organic layers were dried over $Na_2SO_4$, and concentrated to give the crude product, which was partitioned between DCM and 0.5N NaOH (120 mL). The alkaline layer was extracted with DCM (3×), then acidified to pH 3 by adding 4 N HCl at 0° C. The resulting precipitate was extracted with DCM (3×). The combined DCM layers were dried over $Na_2SO_4$, and concentrated to give the title compound.

LC-MS m/z [M+H]⁺ 266.11 (calc'd 266.10).

Step 4: (4S,5S)-2,5-dioxopyrrolidin-1-vl 3-(4-methoxybenzyl)-4-methyl-2-oxooxazolidine-5-carboxylate To a solution of (4S,5S)-3-(4-methoxybenzyl)-4-methyl-2-oxooxazolidine-5-carboxylic acid (7.17 g, 27.0 mmol), and 1-hydroxypyrrolidine-2,5-dione (3.78 g, 28.4 mmol) in DCM (100 mL) at 0° C. was added EDC (6.22 g, 32.4 mmol). The reaction was stirred from 0° C. to rt overnight, then washed with water three times, dried over $Na_2SO_4$, concentrated to give the title compound. LC-MS m/z [M+H]⁺ 363.18 (calc'd 363.11).

Step 5: (4S,5S)-3-(4-methoxybenzyl)-4-methyl-2-oxooxazolidine-5-carboxamide To a solution of (4S,5S)-2,5-dioxopyrrolidin-1-yl 3-(4-methoxybenzyl)-4-methyl-2-oxooxazolidine-5-carboxylate (9.61 g, 26.5 mmol) in a mixture of dioxane (120 mL)/DCM (50 mL)/THF (100 mL)/water (50 mL) at 0° C. was added dropwise ammonium hydroxide (18.44 mL, 133.0 mmol). The reaction mixture was stirred at 0° C. for 10 min, then concentrated. The resulting residue was partitioned between DCM and saturated $NaHCO_3$. The aqueous phase was separated and extracted with DCM (3×). The combined organic layers were dried over $Na_2SO_4$, and concentrated to give the title compound. LC-MS m/z [M+H]⁺ 265.12 (calc'd 265.11).

Step 6: (4S,5S)-3-(4-methoxybenzyl)-4-methyl-2-oxooxazolidine-5-carbonitrile To the solution of (4S,5S)-3-(4-methoxybenzyl)-4-methyl-2-oxooxazolidine-5-carboxamide (5.77 g, 21.83 mmol) in DMF (40 mL) at 0° C. was added cyanuric chloride (4.83 g, 26.2 mmol). The reaction was stirred from 0° C. for 1 h, then quenched by the addition of saturated NaHC03. The mixture was then partitioned between EtOAc (300 mL) and saturated NaHCO$_3$(20 mL). The water layer was extracted once with EtOAc, and the combined organic layers were washed with saturated NaHCO$_3$(3×), dried over Na$_2$SO$_4$, and concentrated. The resulting residue was purified by flash chromatography (0% to 100% EtOAc in hexane) to give the title compound. LC-MS m/z [M+H]$^+$ 247.16 (calc'd 247.10).

Step 7: (4S,5S)-3-(4-methoxybenzyl)-4-methyl-2-oxooxazolidine-5-carboximidamide hydrochloride To a solution of (4S,5S)-3-(4-methoxybenzyl)-4-methyl-2-oxooxazolidine-5-carbonitrile (0.60 g, 2.4 mmol) and MeOH (0.12 mL, 2.9 mmol) in diethyl ether (20 mL) at 0° C. was bubbled HCl gas and the reaction was stirred for 2 h. Then the reaction mixture was concentrated. The resulting residue was dissolved in MeOH (20 mL) and added to ammonia (7 N in MeOH, 20 mL, 140.0 mmol) at 0° C. The reaction mixture was stirred at 0° C. for 1 h. Then additional ammonia (7 N in MeOH, 40 mL) was added and the resulting reaction mixture was stirred at rt over the weekend, then concentrated to give the title compound. LC-MS m/z [M+H]$^+$ 264.14 (calc'd 264.13).

Step 8: (4S,5R)-5-(4-hydroxy-6-(trifluoromethyl)pyrimidin-2-yl)-3-(4-methoxybenzyl)-4-methyloxazolidin-2-one The mixture of methyl 4,4,4-trifluoro-3-oxobutanoate (240.0 mg, 1.41 mmol), DIEA (0.45 mL, 2.57 mmol) and (4S,5S)-3-(4-methoxybenzyl)-4-methyl-2-oxooxazolidine-5-carboximidamide hydrochloride (385.0 mg, 1.28 mmol) in dioxane (12 mL) was heated at 120° C. overnight, then concentrated. The resulting residue was partitioned between DCM and saturated NH$_4$Cl, and the water layer was extracted with DCM (2×). The combined organic layers dried over Na$_2$SO$_4$, and concentrated. The resulting residue purified on silica gel column using EtOAc in hexane (0% to 100%) as eluting solvents to give the title compound. LC-MS m/z [M+H]$^+$ 384.14 (calc'd 384.11).

Step 9: (4S,5R)-5-(4-hydroxy-6-(trifluoromethyl)pyrimidin-2-yl)-3-(4-methoxybenzyl)-4-methyloxazolidin-2-one and (4S,5R)-3-(4-methoxybenzyl)-4-methyl-5-(1-methyl-6-oxo-4-(trifluoromethyl)-1,6-dihydropyrimidin-2-yl)oxazolidin-2-one To a solution of (4S,5R)-5-(4-hydroxy-6-(trifluoromethyl)pyrimidin-2-yl)-3-(4-methoxybenzyl)-4-methyloxazolidin-2-one (230.0 mg, 0.60 mmol) in DMF (6 mL) was added CsF (273.0 mg, 1.80 mmol) and MeI (0.11 mL, 1.80 mmol). The reaction mixture was stirred at rt for 4 h. Then the reaction mixture was partitioned between brine and EtOAc. The organic layer was separated and washed with brine (3×), then dried over Na$_2$SO$_4$, and concentrated. The resulting residue was purified on silica gel column using EtOAc/hexane (0% to 50%) as eluting solvents to give (4S,5R)-5-(4-methoxy-6-(trifluoromethyl)pyrimidin-2-yl)-3-(4-methoxybenzyl)-4-methyloxazolidin-2-one (LC-MS m/z [M+H]$^+$ 398.22 (calc'd 398.12), and (4S,5R)-3-(4-methoxybenzyl)-4-methyl-5-(1-methyl-6-oxo-4-(trifluoromethyl)-1,6-dihydropyrimidin-2-yl)oxazolidin-2-one (LC-MS m/z [M+H]$^+$ 398.21 (calc'd 398.12).

Step 10: (4S,5R)-5-(4-methoxy-6-(trifluoromethyl)pyrimidin-2-yl)-4-methyloxazolidin-2-one A solution of (4S,5R)-5-(4-methoxy-6-(trifluoromethyl)pyrimidin-2-yl)-3-(4-methoxybenzyl)-4-methyloxazolidin-2-one (65.0 mg, 0.16 mmol) in TFA (4 mL, 51.9 mmol) was heated at 60° C. over the weekend. The reaction mixture was concentrated, and the resulting residue was purified on silica gel column using EtOAc/hexane (0% to 100%) as eluting solvents to give the title compound. LC-MS m/z [M+H]$^+$ 278.10 (calc'd 278.07).

Step 11: (4S,5R)—N-(isoquinolin-4-ylmethyl)-5-(4-methoxy-6-(trifluoromethyl)pyrimidin-2-yl)-4-methyl-2-oxooxazolidine-3-carboxamide To a solution of (4S,5R)-5-(4-methoxy-6-(trifluoromethyl)pyrimidin-2-yl)-4-methyloxazolidin-2-one from step 10 (33.0 mg, 0.12 mmol) in THF (4 mL) at −78° C. was added n-butyllithium (0.07 mL, 0.12 mmol). The reaction mixture was stirred at −78° C. for 5 min, then diphosgene (0.01 mL, 0.12 mmol) was added. The resulting reaction mixture was stirred at −78° C. for 30 min, then warmed to rt. The reaction mixture was concentrated, and the resulting residue was treated with DCM (4 mL), isoquinolin-4-ylmethanamine dihydrochloride (41.3 mg, 0.178 mmol) and TEA (0.10 mL, 0.71 mmol). The resulting mixture was stirred at rt for 1 h, then concentrated. The resulting residue was purified on reverse phase HPLC using acetonitrile (0.05% TFA)/water(0.05% TFA) as mobile phase to give the title compound. LC-MS m/z [M+H]$^+$ 462.19 (calc'd 462.13).

Example 97

(4S,5R)-5-(3-(3,3-difluoropyrrolidin-1-yl)-5-(trifluoromethyl)phenyl)-4-methyl-2-oxo-N-(quinazolin-8-ylmethyl)oxazolidine-3-carboxamide

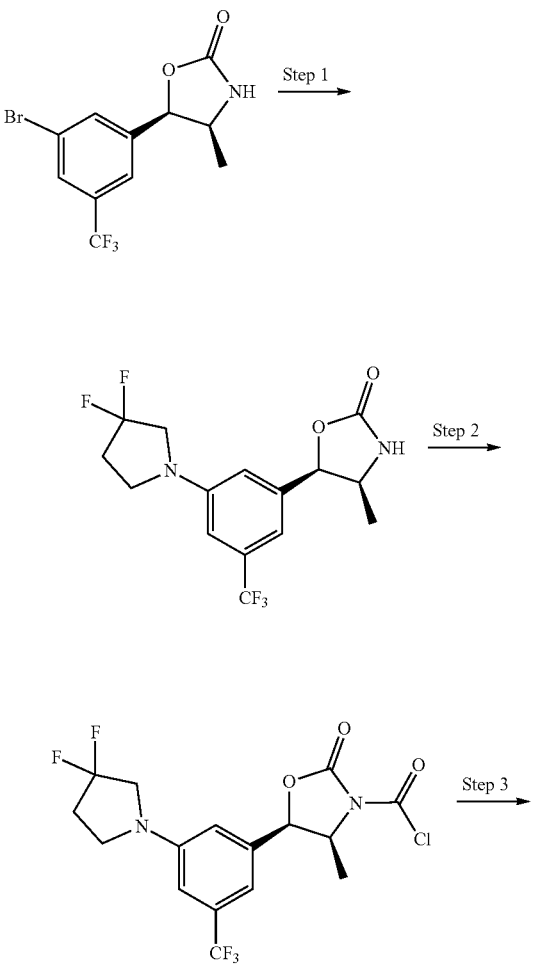

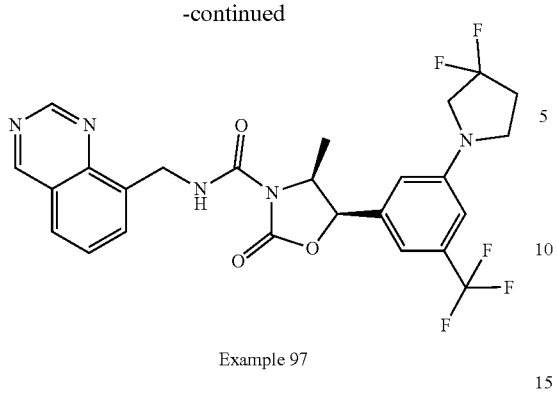

Example 97

Step 1: (4S,5R)-5-(3-(3,3-difluoropyrrolidin-1-yl)-5-(trifluoromethyl)phenyl)-4-methyloxazolidin-2-one To a solution of (4S,5R)-5-(3-bromo-5-(trifluoromethyl)phenyl)-4-methyloxazolidin-2-one (200.0 mg, 0.62 mmol, synthesized via steps 1-2 of Example 1) and 3,3-difluoropyrrolidine HCl (89.0 mg, 0.62 mmol) in dioxane (2 mL) in a microwave tube were added Pd$_2$(dba)$_3$ (11.3 mg, 0.01 mmol), sodium tert-butoxide (65.2 mg, 0.68 mmol) and (9,9-dimethyl-9H-xanthene-4,5-diyl)bis(diphenylphosphine) (Xantphos, 28.6 mg, 0.05 mmol). The tube was capped, degassed and filled with nitrogen. Reaction was heated at 80° C. for 12 h. The reaction mixture was cooled to rt and diluted with ethyl acetate (50 mL), washed with brine, dried with Na$_2$SO$_4$, filtered and concentrated. Purification by flash chromatography (0% to 50% EtOAc in hexane) provided the title compound. LC-MS m/z [M+H]$^+$ 351.13 (calc'd 351.11).

Steps 2 and 3: (4S,5R)-5-(3-(3,3-difluoropyrrolidin-1-yl)-5-(trifluoromethyl)phenyl)-4-methyl-2-oxo-N-(quinazolin-8-ylmethyl)oxazolidine-3-carboxamide was synthesized from the product of Step 1 following the procedures of Steps 3 and 4 of Example 1. LC-MS m/z [M+H]$^+$ 536.33 (calc'd 536.17).

Example 99

(4S,5R)-5-(3-fluoro-5-(trifluoromethyl)phenyl)-4-(2-hydroxyethyl)-N-(isoquinolin-4-ylmethyl)-2-oxooxazolidine-3-carboxamide

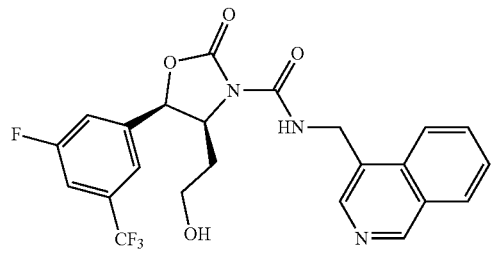 [SMILES: O=C(NCc1cncc2ccccc12)N1C(=O)O[C@H](c2cc(F)cc(C(F)(F)F)c2)[C@@H]1CCO]

Step 1: tert-Butyl (S)-(4-(benzyloxy)-1-(methoxy(methyl)amino)-1-oxobutan-2-yl)carbamate (S)-4-(benzyloxy)-2-((tert-butoxycarbonyl)amino)butanoic acid (4.48 g, 14.48 mmol) in THF (30 mL) was cooled to 0° C., then 1-hydroxybenzotriazole hydrate (2.40 g, 15.64 mmol), N,O-dimethylhydroxylamine hydrochloride (1.70 g, 17.38 mmol), DIPEA (6.2 mL, 35.3 mmol) and EDC (3.47 g, 18.10 mmol) were added. The reaction was stirred at rt overnight, then diluted with EtOAc and washed with 1 N HCl (1×), brine (1×), dried (Na$_2$SO$_4$), filtered and concentrated to give the title compound. LC-MS m/z [M+Na]$^+$ 375.27 (calc'd 375.29)

Step 2: tert-butyl (S)-(4-(benzyloxy)-1-(3-fluoro-5-(trifluoromethyl)phenyl)-1-oxobutan-2-yl)carbamate The title compound was prepared according to the procedure of Step 1 of Example 1. LC-MS m/z [M+H]$^+$ 456.20 (calc'd 456.17)

Step 3: (4S,5R)-4-(2-(benzyloxy)ethyl)-5-(3-fluoro-5-(trifluoromethyl)phenyl)-N-(isoquinolin-4-ylmethyl)-2-oxooxazolidine-3-carboxamide The title compound was prepared according to the procedure of Steps 3 and 4 of Example 1.

Step 4: (4S,5R)-5-(3-fluoro-5-(trifluoromethyl)phenyl)-4-(2-hydroxyethyl)-N-(isoquinolin-4-ylmethyl)-2-oxooxazolidine-3-carboxamide (4S,5R)-4-(2-(benzyloxy)ethyl)-5-(3-fluoro-5-(trifluoromethyl)phenyl)-N-(isoquinolin-4-ylmethyl)-2-oxooxazolidine-3-carboxamide (64.4 mg, 0.11 mmol) was dissolved in DCM (5 mL) and the solution was cooled to −78° C. Then pentamethylbenzene (84.0 mg, 0.57

TABLE 8

Example 98 was prepared according to the procedure of Example 97.

| Example Number | Structure | Name | Calc'd Mass M + H$^+$ | Observed Mass M + H$^+$ |
|---|---|---|---|---|
| 98 | | (4S,5R)-5-[3-(dimethylamino)-5-(trifluoromethyl)phenyl]-N-(isoquinolin-4-ylmethyl)-4-methyl-2-oxo-1,3-oxazolidine-3-carboxamide | 473.18 | 473.03 | mmol) was added, followed by boron trichloride in DCM (0.11 mL, 1 M, 0.11 mmol). The reaction mixture was warmed to 0° C. for 1 h, then cooled to −78° C. Then BCl₃ (0.11 mL, 1 M, 0.11 mmol) was added to the reaction, which was kept at −78° C. for another hour. The reaction mixture was diluted with EtOAc and washed with saturated NaHCO₃ solution (1×), brine (1×), then dried (Na₂SO₄), filtered and concentrated. The resulting residue was purified by flash chromatography (0% to 100% EtOAc in hexane) to give the title compound. LC-MS m/z [M+H]⁺ 478.77 (calc'd 478.13).

Biological Assays

TarO Biochemical Enzymatic Assay

Assay Background The pathway for the biosynthesis of wall teichoic acid (WTA) in Staphylococci involves a series of biochemical enzymatic reactions by proteins encoded by the tar genes (teichoic acid ribitol). The first enzymatic step in the synthesis of WTA is initiated by TarO, N-acetylglucosaminyl-1-P transferase, which catalyzes the transfer of N-acetyl-glucosamine-phosphate (GlcNAc-P) to an undecaprenyl phosphate (C55-P), also known as bactoprenyl phos-

TABLE 9

Example 100 was prepared according to the procedure of Example 65.

| Example Number | Structure | Name | Calc'd Mass M + H⁺ | Observed Mass M + H⁺ |
|---|---|---|---|---|
| 100 | 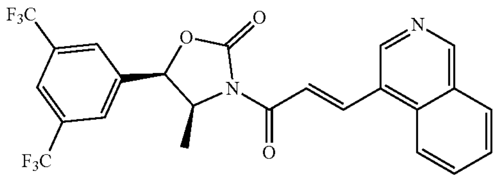 [SMILES: C[C@H]1[C@@H](c2cc(C(F)(F)F)cc(C(F)(F)F)c2)OC(=O)N1C(=O)/C=C/c1cncc2ccccc12] | (4S,5R)-5-(3,5-bis(trifluoromethyl)phenyl)-3-((E)-3-(isoquinolin-4-yl)acryloyl)-4-methyloxazolidin-2-one | 495.11 | 495.07 |

Example 101

(R)-7-(3,5-bis(trifluoromethyl)phenyl)-4-(3-(isoquinolin-4-yl)propanoyl)-6-oxa-4-azaspiro[2.4]heptan-5-one

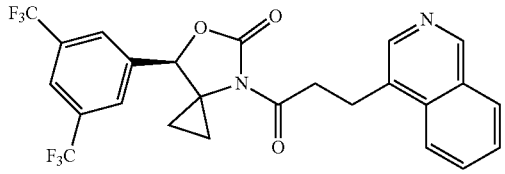 [SMILES: O=C(CCc1cncc2ccccc12)N1C(=O)O[C@H](c2cc(C(F)(F)F)cc(C(F)(F)F)c2)C12CC2]

Step 1: (R)-7-(3,5-bis(trifluoromethyl)phenyl)-6-oxa-4-azaspiro[2.4]heptan-5-one Racemic 7-(3,5-bis(trifluoromethyl)phenyl)-6-oxa-4-azaspiro[2.4]heptan-5-one was prepared according to the procedures in Steps 1-3 of Example 1. LC-MS m/z [M+H]⁺ 326.20 (calc'd 326.05). The racemic material was resolved by AS chiral column using 10% IPA/CO₂ to give the (R)-isomer and the (S)-isomer.

Step 2: (R)-7-(3,5-bis(trifluoromethyl)phenyl)-4-(3-(isoquinolin-4-yl)propanoyl)-6-oxa-4-azaspiro[2.4]heptan-5-one The title compound was prepared according to the procedure of Step 3 of Example 65. LC-MS m/z [M+H]⁺ 509.18 (calc'd 509.12).

Example of a Pharmaceutical Composition

As a specific embodiment of an oral pharmaceutical composition, a 100 mg potency tablet is composed of 100 mg of any one of the Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

phate, to generate C55-PP-GlcNAc (LIPID III). This assays measure the ability of a TarO inhibitor to specifically inhibit the formation of C55-PP-GlcNAc (LIPID III) product thereby blocking the synthesis of the WTA polymer.

TarO Biochemical Enzymatic Assay Protocol The TarO biochemical enzymatic assay is a liquid chromatography-mass spectroscopy (LC-MS) based end point assay that measures C55-P-P-GlcNAc (LIPID III) production. The TarO biochemical enzymatic assay was performed in a 384-well microtiter plate (Labcyte) with a reaction volume of 20 μl. The reaction mix contained 0.1 μgs/μl of TarO membrane preparation derived from MRSA COL (lysostaphin/lysozyme treated, centrifuged at 40K rpm, and resuspended in 50 mM Tris pH 7.5, 10 mM MgCl₂), 1500 M UDP-GlcNAc,×75 μM C55-P substrates in 83 mM Tris pH 8.0, 6.7 mM MgCl₂, 6 mM CHAPS, and 8.3% DMSO buffer. The enzyme reactions were quenched by extraction in 40 l of 1-pentanol containing 0.04 μM 15 C C55-PP-GlcNAc, which was used as an internal standard. A 10 μl volume of the quenched reaction mixture (pH≈3) from each well was injected onto a reversed-phase column (C4, 5 μm, 2.1×50 mm, Thermo Scientific Biobacis-4) and eluted using a NH₄Ac/H₂O/MeOH gradient (solvent A: 10 mM NH₄Ac in water, pH 5.6; solvent B: NH₄Ac (1 M)-Isopropanol (1:90, v/v, pH 5.6). The HPLC conditions were as follows: 15% solvent B for 15 seconds followed by a gradient to 90% solvent B in 90 seconds; then solvent B was kept at 95% for 10 seconds followed by a gradient to 8% solvent B in 0.1 minute. The column was then equilibrated at 15% B for 1 minute before the next injection. The flow rate was kept constant at 600 μl/minute. Mass spectrometric detection was carried out in the negative-ion mode using selected reaction monitoring (SRM). Typical mass spectrometric conditions were as follows: heated capillary temperature, 210° C.; spray voltage, 2500 V; desolvation gas (N₂), 40 l/h; auxiliary gas (N₂), 35 l/h. Selected ion current (SIC) chromatograms of C55-PP-GlcNAc and internal standard 15 C C55-PP-GlcNAc were plotted and integrated using LCQuan incorporated in Xcalibur software (ThermoFinnigan). The linearity of C55-PP-GlcNAc concentration versus mass spectrometric signal (AC55-PP-GlcNAc/A15C-C55-PP-GlcNAc) was determined with purified C55-PP-GlcNAc. The $IC_{50}$ values were calculated using the nonlinear regression analysis (sigmoidal dose response fit allowing for a variable slope) of percent inhibition data with minimum and maximum values set to 0 and 100 percent.

The compounds of the present invention, including the compounds in Examples 1-101, have $IC_{50}$ values less than 100 micromolar (µM) in the TarO Biochemical Enzymatic Assay described above. Preferred compounds of the present invention have $IC_{50}$ values less than 100 nanomolar (nM) in the TarO Biochemical Enzymatic Assay described above. TarO Biochemical Enzymatic Assay $IC_{50}$ values for specific compounds are listed in Table I.

TarO Inhibitor/β-Lactam Synergy Assay

Assay Background The TarO inhibitor/β-lactam synergy assay was performed to measure the re-sensitization of methicillin-resistant Staphylococci bacteria (MB5393: MRSA COL) to β-lactam antibiotics by TarO inhibitors. MRSA COL is a hospital-acquired penicillinase-negative clinically isolated strain commonly used in *Staphylococcus aureus* studies and is fully resistant to the antimicrobial bioactivity of β-lactam antibiotics, including but not limited to imipenem and dicloxacillin. The breakpoint concentrations (measure of susceptibility or resistance to a particular antibiotic) of β-lactam antibiotics have been established by the Clinical and Laboratory Standard Institute (CLSI); the clinical breakpoint for imipenem (IPM) is currently 4 µg/ml, and dicloxacillin (DCX) is currently 8 µg/ml. MRSA COL is fully refractory to β-lactam antibiotic effect at the current clinical breakpoint concentrations and as such MRSA COL is fully viable at these concentrations. When administered to treat MRSA as single therapeutic agents, the breakpoint concentrations of imipenem and dicloxacillin are significantly higher than the current clinical therapeutic threshold.

TarO Inhibitor/β-lactam Synergy Assay Protocol The β-lactam antibiotic concentration was fixed at the clinical breakpoint (imipenem 4 µg/ml or dicloxacillin 8 µg/ml) and the TarO inhibitors were titrated by 2 fold starting from the highest concentration of 200 µM with final DMSO concentration of 2% in the assay. $5 \times 10^5$ colony forming unit of MRSA COL in cation-adjusted Mueller Hinton broth (CANMB) was then mixed and the assay plate was incubated for 20 hours at 37° C. without shaking. After 20 hours, the optical density at 600 nm (OD600) was read for all wells to determine relative growth of MRSA COL. The $MITC_{95}$ concentration for imipenem alone was determined to be 32 µg/ml; the $MITC_{95}$ concentration of dicloxacillin alone was determined to be 128 µg/ml. The $MITC_{95}$ values determined for: 1) the TarO inhibitors alone; 2) the combination of a TarO inhibitor+4 µg/mL of imipenem (IPM); and 3) the combination of a TarO inhibitor+8 µg/mL of dicloxacillin (DCX) are shown in Table I.

The present invention shows that treatment of MRSA bacteria with a TarO inhibitor in combination with a β-lactam antibiotic (imipenem or dicloxacillin) reduces the concentration of β-lactam antibiotic required to render MRSA COL susceptible to β-lactam antibiotic treatment below the current clinical breakpoint concentration. When MRSA COL was treated with imipenem alone in the TarO inhibitor/β-lactam synergy assay described above, the inhibition of MRSA COL viability was not achieved until the imipenem concentration was greater than 32 µg/ml (8 fold higher than breakpoint). Further, when MRSA COL was treated with dicloxacillin alone in the TarO inhibitor/β-lactam synergy assay described above, the inhibition of MRSA COL viability was not achieved until the dicloxacillin concentration was greater than 128 µg/ml (16 fold higher than breakpoint). However, the TarO inhibitors tested in combination with the β-lactam antibiotics imipenem and dicloxacillin showed a synergistic bactericidal effect resulting in the inhibition of MRSA COL at the current breakpoint values of imipenem (4 ug/mL) and dicloxacillin (8 ug/mL). As shown in Table I, the combination of a TarO inhibitor and imipenem showed a synergistic bactericidal effect when administered to treat MRSA COL because a concentration of 4 µg/mL of imipenem was sufficient to inhibit MRSA COL viability when administered in the combination with a TarO inhibitor, whereas as a concentration of 32 µg/mL of imipenem was required to inhibit MRSA COL when administered alone. Additionally, as shown in Table I, the combination of a TarO inhibitor and dicloxacillin also showed a synergistic bactericidal effect when administered to treat MRSA COL because a concentration of 8 µg/mL of dicloxacillin was required to inhibit MRSA COL viability in the combination whereas a concentration of 128 µg/mL of dicloxacillin required to inhibit MRSA COL when administered alone.

TABLE I

Inhibition of TarO and Treatment of MRSA COL with a TarO Inhibitor, alone and in combination with Imipenem (IPM, concentration 4 µg/mL) or Dicloxacillin (DCX, concentration 8 µg/mL)

| Example number TarO inhibitor | TARO inhibitor $IC_{50}$ (µM)[1] | $MITC_{95}$ (µM) TarO inhibitor alone[2]; Bacteria: SA_MB5393 | $MITC_{95}$ (µM) TarO inhibitor + 4 µg/mL IPM[3]; Bacteria: SA_MB5393 | $MITC_{95}$ (µM) TarO inhibitor + 8 µg/mL DCX[4]; Bacteria: SA_MB5393 |
|---|---|---|---|---|
| 1 | 0.03 | >200 | 0.03 | 0.39 |
| 2 | 0.01 | >200 | 0.01 | 0.21 |
| 3 | 0.01 | >200 | 0.33 | 2.60 |
| 4 | 0.01 | >200 | 0.13 | 0.39 |
| 5 | 0.02 | >200 | 0.09 | 0.71 |
| 6 | 0.02 | >200 | 0.01 | 0.02 |
| 7 | 0.03 | >200 | 0.05 | 0.33 |
| 8 | 0.03 | >200 | 0.13 | 1.32 |
| 9 | 0.04 | >200 | 0.22 | 1.65 |
| 10 | 0.05 | >200 | 0.06 | 0.37 |
| 11 | 0.05 | >200 | 0.13 | 1.42 |
| 12 | 0.06 | >200 | 0.25 | 1.56 |
| 13 | 0.10 | >200 | 0.06 | 0.35 |
| 14 | 0.12 | >200 | 0.49 | 5.63 |
| 15 | 0.13 | >200 | 0.98 | 4.69 |
| 16 | 0.14 | >200 | 0.38 | 3.52 |
| 17 | 0.15 | >200 | 0.39 | 4.30 |
| 18 | 0.16 | >200 | 0.23 | 1.95 |
| 19 | 0.16 | >200 | 0.15 | 1.45 |
| 20 | 0.16 | >200 | 0.43 | 3.65 |
| 21 | 0.17 | >200 | 0.16 | 1.73 |
| 22 | 0.19 | >200 | 0.49 | 6.25 |
| 23 | 0.20 | >200 | 0.61 | 4.84 |
| 24 | 0.22 | >200 | 0.20 | 7.29 |
| 25 | 0.24 | >200 | 0.22 | 1.38 |
| 26 | 0.24 | >200 | 0.25 | 0.99 |
| 27 | 0.25 | >200 | 0.39 | 3.65 |
| 28 | 0.26 | >200 | 0.70 | 4.69 |
| 29 | 0.28 | >200 | 0.78 | 5.21 |
| 30 | 0.34 | >200 | 0.68 | 4.69 |
| 31 | 0.44 | >200 | 0.43 | 8.33 |
| 32 | 0.45 | >200 | 0.59 | 4.69 |
| 33 | 0.49 | >200 | 1.37 | 9.38 |
| 34 | 0.54 | >200 | 1.95 | 14.06 |
| 35 | 0.61 | >200 | 0.10 | 0.98 |
| 36 | 0.69 | >200 | 6.25 | 25 |
| 37 | 0.85 | >200 | 0.98 | 2.73 |
| 38 | 0.91 | >200 | 1.56 | 25 |

TABLE I-continued

Inhibition of TarO and Treatment of MRSA COL
with a TarO Inhibitor, alone and in
combination with Imipenem (IPM, concentration 4 µg/mL)
or Dicloxacillin (DCX, concentration 8 µg/mL)

| Example number TarO inhibitor | TARO inhibitor $IC_{50}$ (µM)[1] | $MITC_{95}$ (µM) TarO inhibitor alone[2]; Bacteria: SA_MB5393 | $MITC_{95}$ (µM) TarO inhibitor + 4 µg/mL IPM[3]; Bacteria: SA_MB5393 | $MITC_{95}$ (µM) TarO inhibitor + 8 µg/mL DCX[4]; Bacteria: SA_MB5393 |
|---|---|---|---|---|
| 39 | 1.42 | >200 | 0.78 | 25 |
| 40 | 1.69 | >200 | 18.75 | 50 |
| 41 | 1.78 | >200 | 1.56 | 16.67 |
| 42 | 1.87 | >200 | 0.78 | 12.50 |
| 43 | 2.65 | >200 | 5.21 | 42 |
| 44 | 2.97 | >200 | 12.50 | 25 |
| 45 | 3.61 | >200 | 4.69 | 25 |
| 46 | 7.76 | >200 | 6.25 | 50 |
| 47 | 77 | >200 | 62 | 50 |
| 48 | 0.01 | >200 | 0.13 | 0.39 |
| 49 | 0.01 | >200 | 0.02 | 0.13 |
| 50 | 0.17 | >200 | 0.22 | 0.64 |
| 51 | 1.24 | >200 | 1.56 | 8.33 |
| 52 | 0.03 | >200 | 0.03 | 0.06 |
| 53 | 0.14 | >200 | 0.39 | 1.37 |
| 54 | 0.08 | >200 | 0.20 | 0.65 |
| 55 | 0.20 | >200 | 0.30 | 1.18 |
| 56 | 0.20 | >200 | 0.03 | 0.13 |
| 57 | 0.21 | >200 | 0.33 | 1.56 |
| 58 | 0.45 | >200 | 1.56 | 6.25 |
| 59 | 0.87 | >200 | 1.95 | 10.42 |
| 60 | 0.26 | >200 | 0.33 | 1.45 |
| 61 | 0.06 | >200 | 0.20 | 0.20 |
| 62 | 0.01 | >200 | 0.19 | 0.72 |
| 63 | 0.15 | >200 | 0.37 | 1.13 |
| 64 | 0.88 | >200 | 0.94 | 4.38 |
| 65 | 0.01 | >200 | 0.06 | 0.20 |
| 66 | 0.00 | >200 | 0.03 | 0.20 |
| 67 | 0.01 | >200 | 0.01 | ND |
| 68 | 0.01 | >200 | 0.01 | 0.20 |
| 69 | 0.04 | >200 | 0.11 | 0.39 |
| 70 | 0.08 | >200 | 0.19 | 0.91 |
| 71 | 0.13 | >200 | 0.89 | ND |
| 72 | 0.14 | >200 | 0.21 | 1.56 |
| 73 | 0.25 | >200 | 0.56 | 6.25 |
| 74 | 0.25 | >200 | 0.30 | 6.25 |
| 75 | 0.41 | >200 | 0.13 | 0.78 |
| 76 | 0.42 | >200 | 0.39 | ND |
| 77 | 1.07 | >200 | 0.63 | 5.21 |
| 78 | 1.81 | >200 | 1.17 | ND |
| 79 | 1.88 | >200 | 1.17 | 12.50 |
| 80 | 3.00 | >200 | 4.69 | ND |
| 81 | 3.00 | >200 | 0.75 | 100.00 |
| 82 | 4.64 | >200 | 9.38 | ND |
| 83 | 0.06 | >200 | 0.06 | 0.59 |
| 84 | 0.48 | >200 | 1.56 | 100 |
| 85 | 0.54 | >200 | 0.55 | 25.00 |
| 86 | 1.20 | >200 | 1.41 | 8.33 |
| 87 | 1.20 | >200 | 2.08 | 50 |
| 88 | 1.49 | >200 | 1.30 | 6.25 |
| 89 | 6.98 | >200 | 6.25 | 75 |
| 90 | 0.68 | >200 | 0.39 | 12.50 |
| 91 | 0.04 | >200 | 0.76 | 4.69 |
| 92 | 0.24 | >200 | 0.51 | 7.50 |
| 93 | 0.03 | >200 | 0.13 | 0.50 |
| 94 | 1.26 | >200 | 3.52 | 44 |
| 95 | 0.95 | >200 | 5.21 | 4.17 |
| 96 | 2.17 | >200 | 4.17 | 25 |
| 97 | 0.26 | >200 | 0.42 | 3.32 |
| 98 | 0.03 | >200 | 0.01 | 0.41 |
| 99 | 4.77 | >200 | 18.75 | 100 |
| 100 | ND | >200 | 1.60 | ND |
| 101 | ND | >200 | 0.20 | ND |

ND is not determined.
$MITC_{95}$ (minimum inhibitory threshold concentration) is the minimum concentration required to inhibit MRSA COL growth by 95%.
[1]TarO $IC_{50}$ (50% inhibitory concentration) is a measure of biochemical inhibition of TarO enzymatic activity.
[2]The minimum concentrations of TarO inhibitors alone of >200 µM are designated as not having achieved 95% growth inhibition or having no growth inhibitory effect in the in vitro assay.
[3]The minimum concentrations of the TarO inhibitors of the present invention required to achieve $MITC_{95}$ when administered in combination with 4 µg/mL of imipenem (IPM).
[4]The minimum concentrations of the TarO inhibitors of the present invention required to achieve $MITC_{95}$ when administered in combination with 8 µg/mL of dicloxacillin (DCX).

In Vivo Murine Systemic Infection Model

Background The murine systemic infection model determines the therapeutic efficacy of TarO inhibitor/β-lactam combinations in vivo. Staphylococci bacteria can cause a systemic infection and establish a robust growth in the kidneys of the infected animal. MRSA COL can establish an infection even in the presence of β-lactam antibiotic due MRSA COL resistance to β-lactam antibiotics. In this model, therapeutic efficacy is achieved when bacteria recovered from the TarO inhibitor/β-lactam antibiotic combination is greater than 100 fold lower than the vehicle alone control group.

Protocol Female Balb/C mice were rendered neutropenic (immune suppressed) with a single 250 mg/kg intraperitoneal (ip) dose of cyclophosphamide on Day 4. MRSA COL (MB 5393) was grown for 16 hours in trypticase soy broth (TSB) at 37° C. and 0.5 mL of diluted culture (~1×10$^4$ cfu) was administered intraperitoneal (IP). The TarO inhibitor and β-lactam antibiotic were administered alone or in combination by subcutaneous route at 2, 5 and 8 hr. post challenge (sc, tid). Twenty four hours post challenge mice were euthanized and the kidneys harvested, weighed, homogenized and plated to measure the total number of bacteria recovered as colony forming unit (CFU) remaining in compound treated groups as compared to vehicle (saline) or β-lactam antibiotic alone groups (statistical analyses was determined by one way ANOVA).

As shown in Table II, the TarO inhibitor of Example 18 alone resulted in the number of bacteria recovered in colony forming units/gram of kidney of 6.6×10$^7$ (~0.9 fold lower), and the combination of TarO inhibitor of Example 18 and dicloxacillin reduced the number of bacteria recovered in colony forming units/gram of kidney to 4.1×10$^4$ (1463 fold lower).

TABLE II

Results of In Vivo Murine Systemic Infection Model

| Treatment Groups | Bacteria recovered [cfu/g kidney] | Fold reduction vs. vehicle alone |
|---|---|---|
| Vehicle alone saline control | 6.0 × 10$^7$ | Not Applicable |
| Imipenem alone (5 mg/kg) | 1.3 × 10$^7$ | 4.6 |

TABLE II-continued

Results of In Vivo Murine Systemic Infection Model

| Treatment Groups | Bacteria recovered [cfu/g kidney] | Fold reduction vs. vehicle alone |
|---|---|---|
| Example 18 alone (50 mg/kg) | $6.6 \times 10^7$ | −0.9 |
| Example 18 (50 mg/kg) + Imipenem (5 mg/kg) | $4.1 \times 10^4$ | 1463.4 |

Data is an average of 5 mice for each treatment group

The scope of the claims should not be limited by the preferred embodiments set forth in the examples, but should be given the broadest interpretation consistent with the description as a whole.

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention.

What is claimed is:

1. A method of treating a methicillin-resistant *S. aureus* infection or a methicillin-resistant *S. epidermidis* infection in a patient by administering to a patient in need thereof a synergistic combination of a beta-lactam antibiotic, wherein the beta-lactam antibiotic is cephalexin, imipenem, or dicloxacillin; a pharmaceutically acceptable carrier; and a compound of structural formula I:

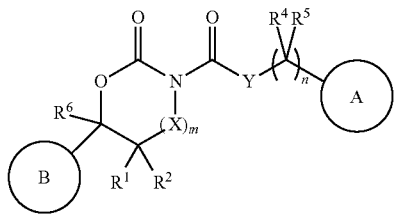

I or a pharmaceutically acceptable salt thereof; wherein
A is selected from the group consisting of:
  (1) aryl,
  (2) heteroaryl,
  (3) —O-aryl, and
  (4) —O-heteroaryl,
wherein aryl and heteroaryl are unsubstituted or substituted with 1-5 substituents selected from $R^a$;
B is selected from the group consisting of:
  (1) aryl, and
  (2) heteroaryl,
wherein aryl and heteroaryl are substituted, and wherein aryl and heteroaryl are substituted with 0-4 substituents selected from $R^{b1}$ and 0-1 substituents selected from $R^{b2}$;
X is —$CR^8R^9$;
Y is selected from the group consisting of:
  (1) $NR^3$, and
  (2) —$CR^{10}R^{11}$;
$R^1$ is selected from the group consisting of:
  (1) —$C_{1-6}$alkyl, and
  (2) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;
$R^2$ is selected from the group consisting of:
  (1) hydrogen, and
  (2) —$C_{1-6}$alkyl,
wherein alkyl is unsubstituted or substituted with 1-2 substituents selected from: halogen, —$C_{1-6}$alkyl, and —$OC_{1-6}$alkyl, or $R^1$ and $R^2$ together with the carbon atom they are attached to form a $C_{3-6}$cycloalkyl ring, wherein the cycloalkyl ring is unsubstituted or substituted with 1-2 substituents selected from: halogen, —$C_{1-6}$alkyl, and —$OC_{1-6}$alkyl;
$R^3$ is selected from the group consisting of:
  (1) hydrogen, and
  (2) —$C_{1-6}$alkyl,
wherein alkyl is unsubstituted or substituted with one to five substituents selected from —$C_{1-6}$alkyl;
each $R^4$ is independently selected from the group consisting of:
  (1) hydrogen,
  (2) halogen,
  (3) —$C_{1-6}$alkyl, and
  (4) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;
each $R^5$ is independently selected from the group consisting of:
  (1) hydrogen,
  (2) halogen,
  (3) —$C_{1-6}$alkyl, and
  (4) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;
$R^6$ is selected from the group consisting of:
  (1) hydrogen,
  (2) —$C_{1-6}$alkyl, and
  (3) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;
$R^8$ is selected from the group consisting of:
  (1) hydrogen, and
  (2) —$C_{1-6}$alkyl,
wherein alkyl is unsubstituted or substituted with 1-2 substituents selected from: halogen, $C_{1-6}$alkyl, and —$OC_{1-6}$alkyl;
$R^9$ is selected from the group consisting of:
  (1) hydrogen, and
  (2) —$C_{1-6}$alkyl,
wherein alkyl is unsubstituted or substituted with 1-2 substituents selected from: halogen, —$C_{1-6}$alkyl, and —$OC_{1-6}$alkyl;

$R^{10}$ is selected from the group consisting of:
(1) hydrogen,
(2) —$C_{1-6}$alkyl, and
(3) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;

$R^{11}$ is selected from the group consisting of:
(1) hydrogen,
(2) —$C_{1-6}$alkyl, and
(3) —$(CH_2)_p$—OH,
wherein $CH_2$ and alkyl are unsubstituted or substituted with 1-2 substituents selected from: halogen, —$C_{1-6}$alkyl, and —$OC_{1-6}$alkyl;

each $R^a$ is independently selected from the group consisting of:
(1) halogen,
(2) —$C_{1-6}$alkyl,
(3) —$OC_{1-6}$alkyl,
(4) —$OC_{2-6}$alkenyl,
(5) —OH,
(6) oxo,
(7) —CN,
(8) —$NO_2$,
(9) —$NR^cR^d$,
(10) —$CH_2NR^cR^d$,
(11) —$SO_2C_{1-6}$alkyl,
(12) —$C_{3-6}$cycloalkyl,
(13) —$C_{2-6}$cycloheteroalkyl,
(14) aryl, and
(15) heteroaryl,
wherein —$CH_2$, alkyl, alkenyl, cycloalkyl, cycloheteroalkyl, aryl and heteroaryl are unsubstituted or substituted with 1-4 substituents selected from: halogen, —$C_{1-6}$alkyl, —$OC_{1-6}$alkyl, and —$CO_2C_{1-6}$alkyl;

each $R^{b1}$ is independently selected from the group consisting of:
(1) halogen,
(2) —$C_{1-6}$alkyl,
(3) —$C_{2-6}$alkenyl,
(4) —CN,
(5) —$NO_2$,
(6) —$NR^cR^d$,
(7) —$SO_2C_{1-6}$alkyl,
(8) —$C_{3-6}$cycloalkyl,
(9) —$C_{2-6}$cycloheteroalkyl,
(10) aryl, and
(11) heteroaryl,
wherein alkyl, alkenyl, cycloalkyl, cycloheteroalkyl, aryl and heteroaryl are unsubstituted or substituted with 1-4 substituents selected from: halogen, —$C_{1-6}$alkyl, —$OC_{1-6}$alkyl, and —$CO_2C_{1-6}$alkyl;

each $R^{b2}$ is independently selected from the group consisting of:
(1) —$OC_{1-6}$alkyl,
(2) —$OC_{2-6}$alkenyl,
(3) —OH,
(4) oxo,
wherein alkyl, alkenyl are unsubstituted or substituted with 1-4 substituents selected from: halogen, —$C_{1-6}$alkyl, —$OC_{1-6}$alkyl, and —$CO_2C_{1-6}$alkyl;

each $R^c$ is independently selected from the group consisting of:
(1) hydrogen,
(2) $C_{1-6}$alkyl,
(3) $C_{2-6}$alkenyl,
(4) $C_{1-6}$alkyl-OH,
(5) $C_{3-6}$cycloalkyl,
(6) $C(O)C_{1-6}$alkyl, and
(7) $SO_2C_{1-6}$alkyl,
wherein alkyl, alkenyl and cycloalkyl are unsubstituted or substituted with one to three substituents selected from halogen, —$C_{1-6}$alkyl, —$OC_{1-6}$alkyl, and —$CO_2C_{1-6}$alkyl;

each $R^d$ is independently selected from the group consisting of:
(1) hydrogen,
(2) $C_{1-6}$alkyl,
(3) $C_{2-6}$alkenyl,
(4) $C_{1-6}$alkyl-OH,
(5) $C_{3-6}$cycloalkyl,
(6) $C(O)C_{1-6}$alkyl, and
(7) $SO_2C_{1-6}$alkyl,
wherein alkyl, alkenyl and cycloalkyl are unsubstituted or substituted with one to three substituents selected from halogen, —$C_{1-6}$alkyl, —$OC_{1-6}$alkyl, and —$CO_2C_{1-6}$alkyl, or $R^c$ and $R^d$ together with the nitrogen atom they are attached to form a $C_{4-8}$cycloheteroalkyl ring, wherein the $C_{4-8}$cycloheteroalkyl ring is unsubstituted or substituted with 1-4 substituents selected from halogen, —$C_{1-6}$alkyl, —$OC_{1-6}$alkyl, and —$CO_2C_{1-6}$alkyl;

m is 0 or 1;

n is 0, 1, 2 or 3; and p is 0, 1, 2, 3, 4, 5 or 6.

2. The method according to claim 1, wherein the compound of structural formula I is

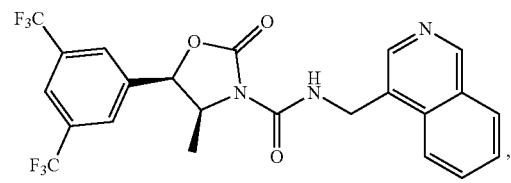

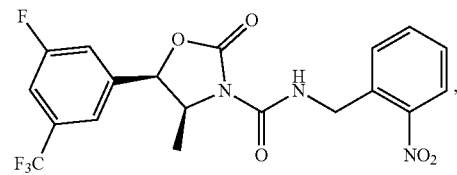

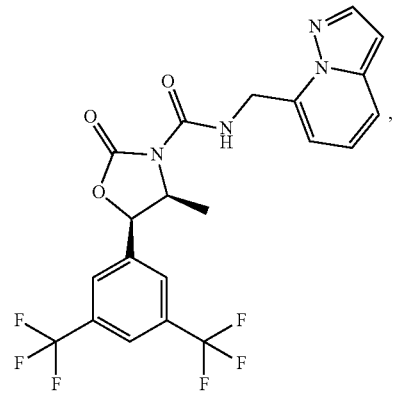

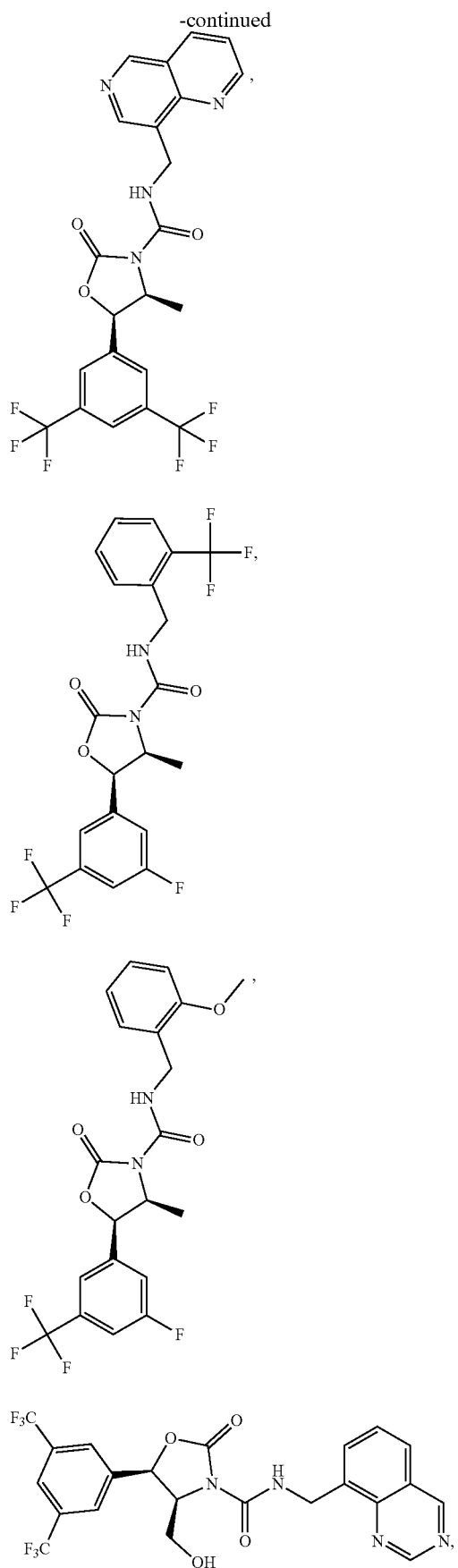
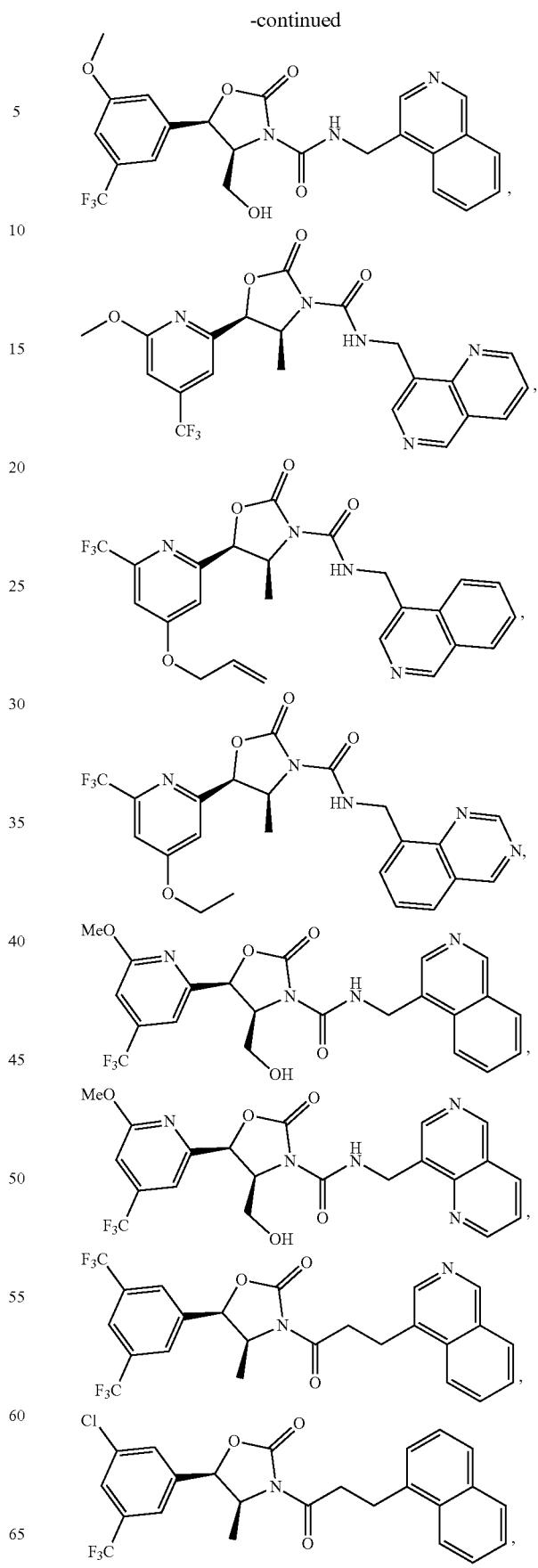

-continued

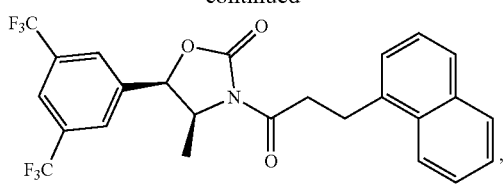

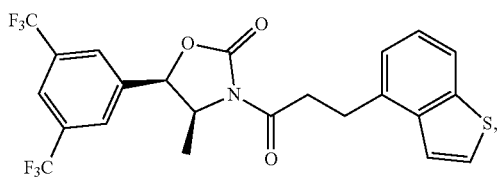

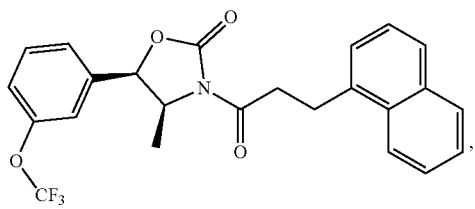

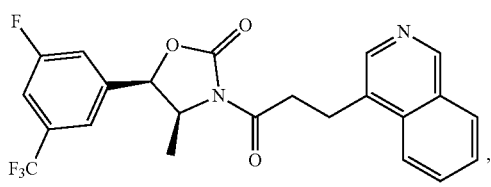

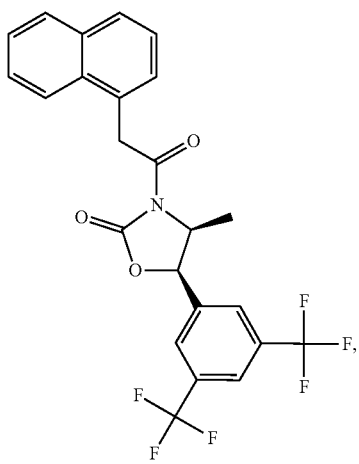

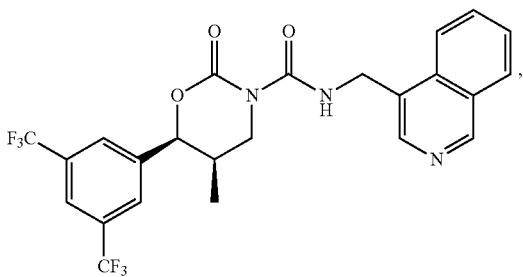

-continued

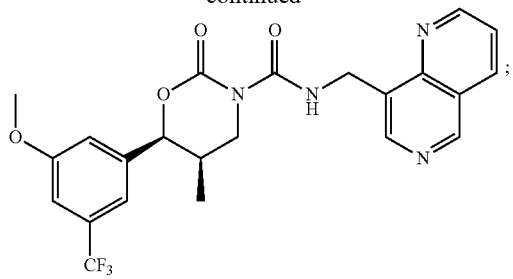

or pharmaceutically acceptable salts thereof.

3. The method according to claim 1, wherein A is selected from the group consisting of:
(1) aryl,
(2) heteroaryl, and
(3) —O-aryl,
wherein aryl and heteroaryl are unsubstituted or substituted with 1-5 substituents selected from $R^a$; or a pharmaceutically acceptable salt thereof.

4. The method according to claim 1, wherein A is selected from the group consisting of:
(1) aryl, and
(2) heteroaryl,
wherein aryl and heteroaryl are unsubstituted or substituted with 1-5 substituents selected from $R^a$; or a pharmaceutically acceptable salt thereof.

5. The method according to claim 1, wherein B is aryl, wherein aryl is unsubstituted or substituted with 1-4 substituents selected from $R^b$; or a pharmaceutically acceptable salt thereof.

6. The method according to claim 1, wherein B is heteroaryl, wherein heteroaryl is unsubstituted or substituted with 1-4 substituents selected from $R^b$; or a pharmaceutically acceptable salt thereof.

7. The method according to claim 1, wherein Y is —$CR^{10}R^{11}$ or a pharmaceutically acceptable salt thereof.

8. The method according to claim 1, wherein Y is $NR^3$; or a pharmaceutically acceptable salt thereof.

9. The method according to claim 1, wherein $R^1$ is selected from the group consisting of:
(1) hydrogen,
(2) —$C_{1-6}$alkyl, and
(3) —$(CH_2)_p$—OH,
wherein $CH_2$ and alkyl are unsubstituted or substituted with 1-2 substituents selected from:
halogen, —$C_{1-6}$alkyl, and —$OC_{1-6}$alkyl; or a pharmaceutically acceptable salt thereof.

10. The method according to claim 1, wherein $R^1$ is selected from the group consisting of:
(1) hydrogen, and
(2) —$C_{1-6}$alkyl,
wherein alkyl is unsubstituted or substituted with 1-2 substituents selected from: halogen, —$C_{1-6}$alkyl, and —$OC_{1-6}$alkyl; or a pharmaceutically acceptable salt thereof.

11. The method according to claim 1, wherein $R^2$ is selected from the group consisting of:
(1) hydrogen,
(2) —$C_{1-6}$alkyl, and
(3) —$(CH_2)_p$—OH, wherein $CH_2$ and alkyl are unsubstituted or substituted with 1-2 substituents selected from:

halogen, —$C_{1-6}$alkyl, and —$OC_{1-6}$alkyl, or $R^1$ and $R^2$ together with the carbon atom they are attached to form a $C_{3-6}$cycloalkyl ring, wherein the cycloalkyl ring is unsubstituted or substituted with 1-2 substituents selected from:

halogen, —$C_{1-6}$alkyl, and —$OC_{1-6}$alkyl; or a pharmaceutically acceptable salt thereof.

12. The method according to claim 1, wherein $R^2$ is selected from the group consisting of:
   (1) hydrogen,
   (2) —$C_{1-6}$alkyl, and
   (3) —$(CH_2)_p$—OH, wherein $CH_2$ and alkyl are unsubstituted or substituted with 1-2 substituents selected from:

halogen, —$C_{1-6}$alkyl, and —$OC_{1-6}$alkyl; or a pharmaceutically acceptable salt thereof.

13. The method according to claim 1, wherein $R^3$ is selected from the group consisting of:
   (1) hydrogen, and
   (2) OH;

or a pharmaceutically acceptable salt thereof.

14. The method according to claim 1, wherein $R^3$ is hydrogen; or a pharmaceutically acceptable salt thereof.

* * * * *